US008211440B2

(12) United States Patent
Chang et al.

(10) Patent No.: US 8,211,440 B2
(45) Date of Patent: Jul. 3, 2012

(54) MULTIVALENT IMMUNOGLOBULIN-BASED BIOACTIVE ASSEMBLIES

(75) Inventors: Chien-Hsing Chang, Downingtown, PA (US); David M. Goldenberg, Mendham, NJ (US); Edmund A. Rossi, Woodland Park, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 0 days.

(21) Appl. No.: 12/949,536

(22) Filed: Nov. 18, 2010

(65) Prior Publication Data

US 2011/0110851 A1 May 12, 2011

Related U.S. Application Data

(60) Division of application No. 12/396,605, filed on Mar. 3, 2009, now Pat. No. 7,858,070, which is a division of application No. 11/633,729, filed on Dec. 5, 2006, now Pat. No. 7,527,787, which is a continuation-in-part of application No. PCT/US2006/025499, filed on Jun. 29, 2006, and a continuation-in-part of application No. PCT/US2006/012084, filed on Mar. 29, 2006, and a continuation-in-part of application No. PCT/US2006/010762, filed on Mar. 24, 2006, and a continuation-in-part of application No. 11/389,358, filed on Mar. 24, 2006, now Pat. No. 7,550,143, and a continuation-in-part of application No. 11/391,584, filed on Mar. 28, 2006, now Pat. No. 7,521,056, and a continuation-in-part of application No. 11/478,021, filed on Jun. 29, 2006, now Pat. No. 7,534,866.

(60) Provisional application No. 60/782,332, filed on Mar. 14, 2006, provisional application No. 60/728,292, filed on Oct. 19, 2005, provisional application No. 60/751,196, filed on Dec. 16, 2005, provisional application No. 60/864,530, filed on Nov. 6, 2006.

(51) Int. Cl.
*A61K 39/395* (2006.01)
*A61K 39/00* (2006.01)

(52) U.S. Cl. ............... 424/193.1; 424/178.1; 424/130.1; 424/134.1; 424/136.1; 424/141.1; 424/142.1; 424/143.1; 424/181.1; 424/182.1; 424/183.1

(58) Field of Classification Search .................. None
See application file for complete search history.

(56) References Cited

U.S. PATENT DOCUMENTS

| | | | |
|---|---|---|---|
| 4,046,722 A | 9/1977 | Rowland | |
| 4,699,784 A | 10/1987 | Shih et al. | |
| 4,868,109 A | 9/1989 | Lansdorp et al. | |
| 5,770,198 A | 6/1998 | Coller et al. | |
| 6,261,537 B1 | 7/2001 | Klaveness | |
| 6,306,393 B1 | 10/2001 | Goldenberg et al. | |
| 6,524,854 B1 | 2/2003 | Mania et al. | |
| 7,060,506 B2 | 6/2006 | Craig | |
| 7,151,164 B2 | 12/2006 | Hansen et al. | |
| 7,432,342 B2 | 10/2008 | Braun et al. | |
| 7,521,056 B2 * | 4/2009 | Chang et al. | 424/192.1 |
| 7,527,787 B2 * | 5/2009 | Chang et al. | 424/133.1 |
| 7,534,866 B2 | 5/2009 | Chang et al. | |
| 7,550,143 B2 | 6/2009 | Chang et al. | |
| 7,591,994 B2 | 9/2009 | Govindan et al. | |
| 7,858,070 B2 * | 12/2010 | Chang et al. | 424/1.41 |
| 7,871,622 B2 * | 1/2011 | Chang et al. | 424/178.1 |
| 7,901,680 B2 * | 3/2011 | Chang et al. | 424/134.1 |
| 7,906,118 B2 * | 3/2011 | Chang et al. | 424/134.1 |
| 2003/0198956 A1 | 10/2003 | Makowski et al. | |
| 2004/0018587 A1 | 1/2004 | Makowski et al. | |
| 2005/0003403 A1 | 1/2005 | Rossi et al. | |
| 2006/0228300 A1 | 10/2006 | Chang et al. | |
| 2006/0228357 A1 | 10/2006 | Chang et al. | |
| 2007/0086942 A1 | 4/2007 | Chang et al. | |
| 2009/0202433 A1 | 8/2009 | Chang et al. | |
| 2009/0202487 A1 | 8/2009 | Chang et al. | |
| 2009/0304580 A1 | 12/2009 | Goldenberg et al. | |
| 2010/0068137 A1 | 3/2010 | Chang et al. | |
| 2010/0189641 A1 | 7/2010 | Chang et al. | |
| 2010/0189689 A1 | 7/2010 | Chang et al. | |
| 2010/0196266 A1 | 8/2010 | Goldenberg et al. | |

FOREIGN PATENT DOCUMENTS

| WO | WO0068248 | 11/2000 |
|---|---|---|
| WO | WO2007075270 | 7/2007 |

OTHER PUBLICATIONS

Henry et al, Cancer Res. 64: 7995-8001, Nov. 1, 2004.*
Stancovski et al, Proceedings of the National Academy of Science USA 88: 8691-8695, 1991.*
Riemer et al, Mol. Immunol. 42: 1121-1124, 2005.*
Tol et al, N. Engl J Med. 360(6):563-72, Feb. 5, 2009.*
Abbas et al., Cellular and Molecular Immunology, W.B. Saunders Company, 1991, p. 43.
Alto et al., "Bioinformatic design of A-kinase anchoring protein-in silico: A potent and selective peptide antagonist of type II protein kinase A anchoring", PNAS USA 100:4445-50, 2003.
Backer et al., "Self-Assembled "Dock and Lock" System for Linking Payloads to Targeting Proteins", Bioconjugate Chem., 17 (4), pp. 912-919, 2006.

(Continued)

*Primary Examiner* — Phuong Huynh
(74) *Attorney, Agent, or Firm* — Richard A. Nakashima

(57) ABSTRACT

The present invention concerns methods and compositions for stably tethered structures of defined compositions, which may have multiple functionalities and/or binding specificities. Preferred embodiments concern hexameric stably tethered structures comprising one or more IgG antibody fragments and which may be monospecific or bispecific. The disclosed methods and compositions provide a facile and general way to obtain stably tethered structures of virtually any functionality and/or binding specificity. The stably tethered structures may be administered to subjects for diagnostic and/or therapeutic use, for example for treatment of cancer or autoimmune disease. The stably tethered structures may bind to and/or be conjugated to a variety of known effectors, such as drugs, enzymes, radionuclides, therapeutic agents and/or diagnostic agents.

25 Claims, 35 Drawing Sheets

OTHER PUBLICATIONS

Banky et al., "Dimerization/Docking Domain of the Type Iα Regulatory Subunit of cAMP-dependent Protein Kinase", J. Biol. Chem. 273:35048-55, 1998.

Burns-Hamuro et al., "Distinct interaction modes of an AKAP bound to two regulatory subunit isoforms of protein kinase A revealed by amide hydrogen/deuterium exchange", Protein Science (2005), 14:2982-2992.

Carr et al., "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).

Carr et al., "Identification of Sperm-specific Proteins That Interact with A-kinase Anchoring Proteins in a Manner Similar to the Type II Regulatory Subunit of PKA", J. Biol. Chem. 2001 276:17332-17338.

Chang et al., "The Dock and Lock Method: A Novel Platform Technology for Building Multivalent, Multifunctional Structures of Defined Composition with Retained Bioactivity", Clin. Cancer Res. 13:5586s-5591s, 2007.

Colledge et al., "AKAPs: from structure to function", Trends Cell Biol. 6:216-21 (1999).

Corbin et al., "Regulation of Adenosine 3',5'-Monophosphate-dependent Protein Kinase", J. Biol. Chem. 248:1813-21 (1973).

Gillies et al., "High-level expression of chimeric antibodies using adapted cDNA variable region cassettes", J. Immunol. Methods 125 (1989) 191-202.

Gold et al., "Molecular Basis of AKAP Specificity for PKA Regulatory Subunits", Mol. Cell (2006) 24:383-395.

Gold et al., "A Novel Bispecific, Trivalent Antibody Construct for Targeting Pancreatic Carcinoma", Cancer Res. 68:4819-26, 2008.

Goldenberg et al., "Multifunctional Antibodies by the Dock-and-Lock Method for Improved Cancer Imaging and Therapy by Pretargeting", J. Nucl. Med. 49:158-63, 2008.

Hausken et al., "Mutational Analysis of the A-Kinase Anchoring Protein (AKAP)-binding Site on RII", J. Biol. Chem. 271:29016-22 (1996).

Hodneland et al., "Selective immobilization of proteins to self-assembled monolayers presenting active site-directed capture ligands", Proc. Natl. Acd. Sci. USA 2002; 99:5048-5052.

Hundsrucker et al., "High-affinity AKAP7δ—protein kinase A interaction yields novel protein kinase A-anchoring disruptor peptides", Biochem. J. (2006) 396:297-306.

Kinderman et al., "A Novel and Dynamic Mechanism for AKAP Binding to RII Isoforms of cAMP-dependent Protein Kinase", Mol. Cell (2006) 24(3): 397-408.

Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).

Mason, Anthony J., "Functional Analysis of the Cysteine Residues of Activin A", Mol. Endocrinol. 8:325-32, 1994.

Newlon et al., "A Novel Mechanism of PKA Anchoring Revealed by Solution Structures of Anchoring Complexes", EMBO J. 2001; 20:1651-1662.

Newlon et al., "The molecular basis for protein kinase A anchoring revealed by solution NMR", Nature Struct. Biol. 1999; 3:222-227.

Ngo et al., "Computational Complexity, Protein Structure Prediction, and the Levinthal Paradox", The Protein Folding Problem and Tertiary Structure Prediction, Ch. 14, pp. 491-495, (Mertz & Le Grand, Eds.), Birkhauser Boston, 1994.

Oyen et al., "Human testis cDNA for the regulatory subunit RIIα of cAMP-dependent protein kinase encodes an alternate amino-terminal region", FEBS Letters 246:57-64, 1989.

Rabjohn et al., "Molecular Cloning and Epitope Analysis of the Peanut Allergen Ara h 3", J. Clinical Investigation 103 (4):535-542 (1999).

Rose et al., "Structural basis of dimerization, coactivator recognition and MODY3 mutations in HNF-1α", Nature Struct. Biol. 2000; 7:744-748.

Rossi et al. "Novel Designs of Multivalent Anti-CD20 Humanized Antibodies as Improved Lymphoma Therapeutics", Cancer Res. 68:8384-92, 2008.

Rossi et al., "Stably tethered multifunctional structures of defined composition made by the dock and lock method for use in cancer targeting", Proc. Natl. Acad. Sci. USA 103:6841-46, 2006.

Rustandi et al., "The Ca2+-Dependent Interaction of S100B(ββ) with a Peptide Derived from p53", Biochemistry 1998; 37: 1951-1960.

Scott et al., "Type II Regulatory Subunit Dimerization Determines the Subcellular Localization of the cAMP-dependent Protein Kinase", J. Biol. Chem. 265:21561-66 (1990).

Seffernick et al., "Melamine Deaminase and Atrazine Chlorohydrolase: 98 Percent Identical but Functionally Different", J. Bacteriol. 183(8):2405-2410 (2001).

Sharkey et al., "Improved Therapeutic Results by Pretargeted Radioimmunotherapy of Non—Hodgkin's Lymphoma with a New Recombinant, Trivalent, Anti-CD20, Bispecific Antibody", Cancer Res. 68:5282-90, 2008.

Sharkey et al., "Metastatic Human Colonic Carcinoma: Molecular Imaging with Pretargeted SPECT and PET in a Mouse Model", Radiology 246:497-507, 2008.

Stokka et al., "Characterization of A-kinase-anchoring disruptors using a solution-based assay", Biochem. J. (2006) 400:493-499.

Stryer et al., "Levels of Structure in Protein Architecture", Biochemistry, 3rd Ed., pp. 31-33, W.H. Freeman & Co., New York, 1988.

Winkler et al., "Changing the Antigen Binding Specificity by Single Point Mutations of an Anti-p24 (HIV-1) Antibody", J. Immunol. 165:4505-14, 2000.

Witkowski et al., "Conversion of a β-Ketoacyl Synthase to a Malonyl Decarboxylase by Replacement of the Active-Site Cysteine with Glutamine", Biochemistry 38(36):11643-50 (1999).

Wong et al., "AKAP Signalling Complexes: Focal Points in Space and Time", Nat. Rev. Mol. Cell Biol. 12:959-70 (2004).

Zhu et al., "Inhibition of tumor growth and metastasis by targeting tumor-associated angiogenesis with antagonists to the receptors of vascular endothelial growth factor", Invest. New Drugs 17:195-212, 1999.

* cited by examiner

DDD1:

SHIQIPPGLTELLQGYTVEVLRQQPPDL
VEFAVEYFTRLREARA (SEQ ID NO:1)

DDD2:

CGHIQIPPGLTELLQGYTVEVLRQQPPDLVEFA
VEYFTRLREARA (SEQ ID NO:2)

Figure 1

AD1: QIEYLAKQIVDNAIQQA (SEQ ID NO:3)

AD2: CGQIEYLAKQIVDNAIQQAGC (SEQ ID NO:4)

SE-HPLC analysis of N-K-AD2-hA20 IgG

1. DNL1
2. DNL2
3. Hex-hA20
4. Hex-hLL2
5. DNL1C
6. DNL2C

SE-HPLC Analysis of DNL1 and DNL1C

1. DNL3
2. K-Hex-hA20, prep 1
3. K-Hex-hA20, prep 2
1R. DNL3 reduced
2R. Khex-hA20 reduced
3R. K-Hex-hA20 reduced

MULTIVALENT IMMUNOGLOBULIN-BASED BIOACTIVE ASSEMBLIES

RELATED APPLICATIONS

This application is a divisional of U.S. patent application Ser. No. 12/396,605 (now issued U.S. Pat. No. 7,858,070) filed Mar. 3, 2009, which is a divisional of U.S. patent application Ser. No. 11/633,729 (now issued U.S. Pat. No. 7,527,787), filed Dec. 5, 2006, which is a continuation-in-part of PCT/US2006/010762, filed Mar. 24, 2006; PCT/US2006/012084, filed Mar. 29, 2006; PCT/US2006/025499, filed Jun. 29, 2006; U.S. patent application Ser. No. 11/389,358 (now issued U.S. Pat. No. 7,550,143), filed Mar. 24, 2006; Ser. No. 11/391,584 (now issued U.S. Pat. No. 7,521,056), filed Mar. 28, 2006 and Ser. No. 11/478,021 (now issued U.S. Pat. No. 7,534,866), filed Jun. 29, 2006; which claimed priority to provisional U.S. patent application Nos. 60/782,332, filed Mar. 14, 2005; 60/728,292, filed Oct. 19, 2005, and 60/751,196, filed Dec. 16, 2005. This application claims the benefit under 35 U.S.C. §119(e) to provisional U.S. patent application No. 60/751,196, filed Dec. 16, 2005, and No. 60/864,530, filed Nov. 6, 2006. The text of each of the applications cited above is incorporated herein by reference in its entirety.

BACKGROUND OF THE INVENTION

Existing technologies for the production of antibody-based agents having multiple functions or binding specificities suffer a number of limitations. For agents generated by recombinant engineering, such limitations may include high manufacturing cost, low expression yields, instability in serum, instability in solution resulting in formation of aggregates or dissociated subunits, undefined batch composition due to the presence of multiple product forms, contaminating side-products, reduced functional activities or binding affinity/avidity attributed to steric factors or altered conformations, etc. For agents generated by various methods of chemical cross-linking, high manufacturing cost and heterogeneity of the purified product are two major limitations.

In recent years there has been an increased interest in antibodies or other binding moieties that can bind to more than one antigenic determinant (also referred to as epitopes). Generally, naturally occurring antibodies and monoclonal antibodies have two antigen binding sites that recognize the same epitope. In contrast, bifunctional or bispecific antibodies (hereafter, only the term bispecific antibodies will be used throughout) are synthetically or genetically engineered structures that can bind to two distinct epitopes. Thus, the ability to bind to two different antigenic determinants resides in the same molecular construct.

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. Lancet. 1990; 355:368-371). More recently, a new class of bispecific antibodies termed "bispecific T-cell engagers" (BiTEs) was reported to overcome the limitations of most tumor-targeting bispecific antibodies that involve the recruitment of effector cells for biological activities (Kufer, et al. Trends in Biotechnol. 2004; 22: 238-244). BiTEs are recombinant bispecific single-chain antibodies composed of two distinct single-chain Fc fragments (scFvs) directed against a surface antigen on target cells and CD3 on T cells joined in tandem via a flexible polypeptide linker (Mack, et al., Proc Natl Acad Sci U.S.A. 1995; 92: 7021-7025). BiTEs are produced in mammalian cells and in constrast to other CD3-directed bispecific antibodies are capable of efficiently redirecting human peripheral T lymphocytes to kill target cells without any requirement for pre- or costimulation of the effector T cells (Mack, et al. J Immunol. 1997; 158: 3965-3970; Loffler, et al. Blood. 2000; 95: 2098-2103). BiTE concentrations as low as 10-100 pg/mL (~0.1-2 pM) were shown to be sufficient for achieving half-maximal target cell lysis in vitro (Dreier, et al. Int J Cancer. 2002; 100: 690-697) and tumor growth could be prevented with sub-microgram amounts in mouse models (Dreier, et al. J Immunol. 2003; 170: 4397-4404; Schlereth et al. Cancer Res. 2005; 65: 2882-2889).

Numerous methods to produce bispecific antibodies are known. Methods for construction and use of bispecific and multi-specific antibodies are disclosed, for example, in U.S. Patent Application Publication No. 20050002945, filed Feb. 11, 2004, the entire text of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540). The fused hybridomas are capable of synthesizing two different heavy chains and two different light chains, which can associate randomly to give a heterogeneous population of 10 different antibody structures of which only one of them, amounting to ⅛ of the total antibody molecules, will be bispecific, and therefore must be further purified from the other forms, which even if feasible will not be cost effective. Furthermore, fused hybridomas are often less stable cytogenically than the parent hybridomas, making the generation of a production cell line more problematic.

Another method for producing bispecific antibodies uses heterobifunctional cross-linkers to chemically tether two different monoclonal antibodies, so that the resulting hybrid conjugate will bind to two different targets (Staerz, et al. Nature. 1985; 314:628-631; Perez, et al. Nature. 1985; 316: 354-356). Bispecific antibodies generated by this approach are essentially heteroconjugates of two IgG molecules, which diffuse slowly into tissues and are rapidly removed from the circulation. Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). An alternative approach involves chemically cross-linking two or three separately purified Fab' fragments using appropriate linkers. For example, European Patent Application 0453082 disclosed the application of a tri-maleimide compound to the production of bi- or tri-specific antibody-like structures. A method for preparing tri- and tetra-valent monospecific antigen-binding proteins by covalently linking three or four Fab fragments to each other via a connecting structure is provided in U.S. Pat. No. 6,511,663. All these chemical methods are undesirable for commercial development due to high manufacturing cost, laborious production process, extensive purification steps, low yields (<20%), and heterogeneous products.

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody. These methods also face the inevitable purification problems discussed above.

A method to produce a recombinant bispecific antibody composed of Fab fragments from the same or different antibodies that are brought into association by complementary interactive domains inserted into a region of the antibody heavy chain constant region, was disclosed in U.S. Pat. No. 5,582,996. The complementary interactive domains are selected from reciprocal leucine zippers or a pair of peptide segments, one containing a series of positively charged amino acid residues and the other containing a series of negatively charged amino acid residues. One limitation of such a method is that the individual Fab subunits containing the fused complementary interactive domains appear to have much reduced affinity for their target antigens unless both subunits are combined.

Discrete $V_H$ and $V_L$ domains of antibodies produced by recombinant DNA technology may pair with each other to form a dimer (recombinant Fv fragment) with binding capability (U.S. Pat. No. 4,642,334). However, such non-covalently associated molecules are not sufficiently stable under physiological conditions to have any practical use. Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

Monospecific diabodies, triabodies, and tetrabodies with multiple valencies have been obtained using peptide linkers consisting of 5 amino acid residues or less. Bispecific diabodies, which are heterodimers of two different scFvs, each scFv consisting of the $V_H$ domain from one antibody connected by a short peptide linker to the $V_L$ domain of another antibody, have also been made using a dicistronic expression vector that contains in one cistron a recombinant gene construct comprising $V_{H1}$-linker-$V_{L2}$ and in the other cistron a second recombinant gene construct comprising $V_{H2}$-linker-$V_{L1}$ (Holliger, et al. Proc Natl Acad Sci USA. 1993; 90: 6444-6448; Atwell, et al. Mol Immunol. 1996; 33:1301-1302; Holliger, et al. Nature Biotechnol. 1997; 15: 632-631; Helfrich, et al. Int. J Cancer. 1998; 76: 232-239; Kipriyanov, et al. Int J Cancer. 1998; 77: 763-772; Holliger, et al. Cancer Res. 1999; 59: 2909-2916).

More recently, a tetravalent tandem diabody (termed tandab) with dual specificity has also been reported (Cochlovius, et al. Cancer Res. 2000; 60: 4336-4341). The bispecific tandab is a dimer of two identical polypeptides, each containing four variable domains of two different antibodies ($V_{H1}$, $V_{L1}$, $V_{H2}$, $V_{L2}$) linked in an orientation to facilitate the formation of two potential binding sites for each of the two different specificities upon self-association.

To date, the construction of a vector that expresses bispecific or trispecific triabodies has not been achieved. However, polypeptides comprising a collectin neck region are reported to trimerize (Hoppe, et al. FEBS Letters. 1994; 344: 191-195). The production of homotrimers or heterotrimers from fusion proteins containing a neck region of a collectin is disclosed in U.S. Pat. No. 6,190,886.

Methods of manufacturing scFv-based agents of multivalency and multispecificity by varying the linker length were disclosed in U.S. Pat. No. 5,844,094, U.S. Pat. No. 5,837,242, and WO 98/44001. Methods of manufacturing scFv-based agents of multivalency and multispecificity by constructing two polypeptide chains, one comprising of the $V_H$ domains from at least two antibodies and the other the corresponding $V_L$ domains were disclosed in U.S. Pat. No. 5,989,830 and U.S. Pat. No. 6,239,259. Common problems that have been frequently associated with generating scFv-based agents of multivalency and multispecificity by prior art methods are low expression levels, heterogenous product forms, instability in solution leading to aggregates, instability in serum, and impaired affinity.

A recombinantly produced bispecific or trispecific antibody in which the c-termini of CH1 and $C_L$ of a Fab are each fused to a scFv derived from the same or different monoclonal antibodies was disclosed in U.S. Pat. No. 6,809,185. Major deficiencies of this "Tribody" technology include impaired binding affinity of the appended scFvs, heterogeneity of product forms, and instability in solution leading to aggregates.

Thus, there remains a need in the art for a method of making multivalent structures of either monospecificity or multiple specificities or functionalities, which are of defined composition, homogeneous purity, and unaltered affinity, and can be produced in high yields without the requirement of extensive purification steps. Furthermore, such structures must also be sufficiently stable in serum to allow in vivo applications. A need exists for stable, multivalent structures of monospecificity or multiple specificities or functionalities that are easy to construct and/or obtain in relatively purified form.

SUMMARY OF THE INVENTION

The present invention discloses a platform technology for generating stably tethered structures that may be monospecific and/or monofunctional, or may have multiple functions or binding specificities, and are suitable for in vitro as well as in vivo applications. In preferred embodiments, such stably tethered structures are produced as complexes of two components, referred herein as A and B, via specific interactions between two distinct peptide sequences, one termed dimerization and docking domain (DDD) and the other anchoring domain (AD). In more preferred embodiments, the DDD sequences (shown for DDD1 and DDD2 in FIG. 1) are derived from the regulatory (R) subunits of a cAMP-dependent protein kinase (PKA), and the AD sequences (shown for AD1 and AD2 in FIG. 2) are derived from a specific region found in various A-kinase anchoring proteins (AKAPs) that mediates association with the R subunits of PKA. However, the skilled artisan will realize that other dimerization and docking domains and anchoring domains are known and any such known domains may be used within the scope of the claimed subject matter. The disclosed methods and compositions enable site-directed covalent or non-covalent association of any two complexes with the DDD/AD coupling system. The X-type four-helix bundle dimerization motif that is a structural characteristic of the DDD (Newlon, et al. EMBO J. 2001; 20: 1651-1662; Newlon, et al. Nature Struct Biol. 1999; 3: 222-227) is found in other classes of proteins, such as the S100 proteins (for example, S100B and calcyclin), and the hepatocyte nuclear factor (HNF) family of transcriptional factors (for example, HNF-1a and HNF-1β). As S100 proteins have biological activities such as tumorigenesis, they may be less desirable for such use.

Over 300 proteins that are involved in either signal transduction or transcriptional activation contain a module of 65-70 amino acids termed the sterile a motif (SAM) domain, which has a variation of the X-type four-helix bundle present on its dimerization interface. For S100B, this X-type four-helix bundle enables the binding of each dimer to two p53 peptides derived from the c-terminal regulatory domain (residues 367-388) with micromolar affinity (Rustandi, et al. Biochemistry. 1998; 37: 1951-1960). Similarly, the N-terminal dimerization domain of HNF-1α (HNF-p1) was shown to associate with a dimer of DCoH (dimerization cofactor for HNF-1) via a dimer of HNF-p1 (Rose, et al. Nature Struct Biol. 2000; 7: 744-748). In alternative embodiments, these naturally occurring systems also may be utilized within the claimed methods and compositions to provide stable multimeric structures with multiple functions or binding specificities. Other binding events such as those between an enzyme and its substrate/inhibitor, for example, cutinase and phosphonates (Hodneland, et al. Proc Natl Acd Sci USA. 2002; 99: 5048-5052), may also be utilized to generate the two associating components (the "docking" step), which are subsequently stabilized covalently (the "lock" step).

Other AD sequences of potential use may be found in Patent Application Serial No. US20003/0232420A1, the entire text of which is incorporated herein by reference.

In exemplary embodiments, one component of a binary complex, A, is produced by linking a DDD sequence to the precursor of A, referred to as A, by recombinant engineering or chemical conjugation via a spacer group, resulting in a structure of A/DDD, hereafter referred to as a. As the DDD sequence in a effects the spontaneous formation of a dimer, A is thus composed of $a_2$. The other component of a binary complex, B, is produced by linking an AD sequence to the precursor of B, referred to as B, by recombinant engineering or chemical conjugation via a spacer group, resulting in a structure of B/AD, hereafter referred to as b. The fact that the dimeric structure contained in $a_2$ creates a docking site for binding to the AD sequence contained in b results in a ready association of $a_2$ and b to form a binary complex composed of $a_2b$. In various embodiments, this binding event is further stabilized with a subsequent reaction to covalently secure the two components of the assembly, for example via disulfide bridges, which occurs very efficiently as the initial binding interactions orient the reactive thiol groups to ligate site-specifically.

By placing cysteine residues at strategic locations in both the DDD and AD sequences (as shown for DDD2 and AD2), the binding interaction between $a_2$ and b can be made covalent via disulfide bridges, thereby forming a stably tethered structure that renders in vivo applications more feasible. The stably tethered structure also retains the full functional properties of the two precursors A and B. The inventors are unaware of any prior art bispecific composition with this unique combination of features. The design disclosed above is modular in nature, as each of the two precursors selected can be linked to either DDD or AD and combined afterwards. The two precursors can also be the same (A=B) or different (A≠B). When A=B, the resulting $a_2b$ complex is composed of a stably tethered assembly of three subunits, referred to hereafter as $a_3$. Materials that are amenable as precursors include proteins, peptides, peptide mimetics, polynucleotides, RNAi, oligosaccharides, natural or synthetic polymeric substances, nanoparticles, quantum dots, and organic or inorganic compounds. Other non-limiting examples of precursors of potential use are listed in Tables 6-10 below.

In addition to the use of disulfide linkages for preventing the dissociation of the constituent subunits, other methods for enhancing the overall stability of the stably tethered structure may be practiced. For example, various crosslinking agents or methods that are commercially available or used in research may be selected for such purposes. A potentially useful agent is glutaraldehyde, which has been widely used for probing the structures of non-covalently associated multimeric proteins by cross-linking the constituent subunits to form stable conjugates (Silva, et al. Food Technol Biotechnol. 2004; 42:51-56). Also of interest are two chemical methods involving oxidative crosslinking of protein subunits. One is a proximity labeling technique that employs either hexahistidine-tagged proteins (Fancy, et al. Chem Biol. 1996; 3:551-559) or N-terminal glycine-glycine-histidine-tagged proteins (Brown, et al. Biochemistry. 1998; 37:4397-4406). These tags bind Ni(II) tightly and, when oxidized with a peracid, a Ni(III) species is produced that is capable of mediating a variety of oxidative reactions, including protein-protein crosslinking. Another technique, termed PICUP (photo-induced crosslinking of unmodified proteins) uses $[Ru(II)(bipy)_3]^{2+}$, ammonium persulfate, and visible light to induce protein-protein crosslinking (Fancy and Kodadek. Proc Natl Acad Sci USA. 1999; 96:6020-6024). However, as discussed below, numerous methods for chemically cross-linking peptide, polypeptide, protein or other macromolecular species are known in the art and any such known method may be used to covalently stabilize the binary $a_2b$ complex.

In more preferred embodiments, disclosed in more detail in Examples 23-35 below, hexameric complexes may be formed that are either monospecific or bispecific. Such complexes may be formed, for example, as disclosed in FIG. 10, FIG. 11, and FIG. 13 by attaching one AD2 to each of the C- or N-terminal ends of IgG moieties, which may then bind to DDD2-conjugated Fab fragments or other DDD2-conjugated antibodies or antibody fragments, to form a hexameric complex. As discussed in Examples 23-35, such monospecific or bispecific hexameric complexes show higher binding affinity and increased efficacy compared to the parent antibodies or fragments. Numerous monospecific or bispecific hexameric stably tethered structures are disclosed in Examples 23-35. However, the skilled artisan will realize that the examples are not limiting and a variety of antigen-binding or other functional moieties may be incorporated into the disclosed hexameric structures, discussed in part in Tables 6-10.

The skilled artisan will realize that where the above discussion refers to IgG or Fab fragments, other types of antibodies, antibody fragments, or non-antibody proteins as discussed in more detail below may be substituted. The stably tethered structures may comprise various combinations of antigen-binding components and/or effector components. For example, a bispecific antibody reacting with both activated platelet and tissue plasminogen activator (tPA) would not only prevent further clot formation by inhibiting platelet aggregation but also could dissolve existing clot by recruiting endogenous tPA to the platelet surface (Neblock et al., Bioconjugate Chem. 1991, 3:126-31). A stably tethered structure comprising a multivalent antibody binding component against an internalizing tumor associated antigen (such as CD74) linked to a toxin (such as a ribonuclease) would be valuable for selective delivery of the toxin to destroy the target tumor cell. A stably tethered structure comprising a soluble component of the receptor for IL-4R (sIL-4R) and a soluble component of the receptor for IL-13 (sIL-13R) would be a potential therapeutic agent for treating asthma or allergy.

A hexameric, monospecific stably tethered structure composed of anti-GPIIb/IIIa Fab fragments should be more effective in preventing clot reformation than either the monovalent (ReoPro, Centocor) or bivalent analogs due to higher binding avidity. A stably tethered structure comprising multiple copies of a soluble component of TNFα-R should be more efficacious for arresting TNF than Enbrel (Amgen) in the treatment of rheumatoid arthritis and certain other autoimmune diseases (AID).

The claimed methods and compositions also include conjugates composed of one or more effectors or carriers linked to a stably tethered structure. The effectors or carriers may be linked to the stably tethered structure either non-covalently or covalently, for example by chemical cross-linking or by binding to a bispecific or multispecific stably tethered structure, with a first specificity for a disease-associated target and a second specificity for an effector and/or hapten linked to the effector(s), as discussed further below. Depending on the intended applications, the effector may be selected from a diagnostic agent, a therapeutic agent, a chemotherapeutic agent, a radioisotope, an imaging agent, an anti-angiogenic agent, a cytokine, a chemokine, a growth factor, a drug, a prodrug, an enzyme, a binding molecule, a ligand for a cell surface receptor, a chelator, an immunomodulator, an oligonucleotide, a hormone, a photodetectable label, a dye, a peptide, a toxin, a contrast agent, a paramagnetic label, an ultrasound label, a pro-apoptotic agent, a liposome, a nanoparticle or a combination thereof. Moreover, a conjugate may contain more than one effector, which can be the same or different, or more than one carrier, which can be the same or different. Effectors and carriers can also be present in the same conjugate. When the effector is a chelator, the resulting conjugate is usually further complexed with a metal, which can be either radioactive or non-radioactive. Conjugates containing carriers are also further incorporated with agents of diagnostic or therapeutic functions for the intended applications.

In certain embodiments, the effectors or carriers may be administered to a subject after a stably tethered structure, for example in pre-targeting strategies discussed below. The stably tethered structure may be first administered to the subject and allowed to localize in, for example, a diseased tissue such as a tumor. The effectors or carriers may be added subsequently and allowed to bind to the localized stably tethered structure. Where the effector or carrier is conjugated to a toxic moiety, such as a radionuclide, this pretargeting method reduces the systemic exposure of the subject to toxicity, allowing a proportionately greater delivery of toxic agent to the targeted tissue. Optionally, a clearing agent may be administered to clear non-localized stably tethered structures from circulation before administration of the targetable construct. These methods are known in the art and described in detail in U.S. Pat. No. 4,624,846, WO 92/19273, and Sharkey et al., Int. J. Cancer 51: 266 (1992). An exemplary targetable construct may have a structure of X-Phe-Lys(HSG)-D-Tyr-Lys(HSG)-Lys(Y)-$NH_2$, where the compound includes a hard acid cation chelator at X or Y, and a soft acid cation chelator at remaining X or Y; and wherein the compound further comprises at least one diagnostic or therapeutic cation, and/or one or more chelated or chemically bound therapeutic agents, diagnostic agents, or enzymes. The diagnostic agent could be, for example, Gd(III), Eu(III), Dy(III), Pr(III), Pa(IV), Mn(II), Cr(III), Co(III), Fe(III), Cu(II), Ni(II), Ti(III), V(IV) ions or a radical. A second exemplary construct may be of the formula X-Phe-Lys(HSG)-D-Tyr-Lys(HSG)-Lys(Y)-$NH_2$, where the compound includes a hard acid cation chelator or a soft acid chelator at X or Y, and nothing at the remaining X or Y; and wherein the compound further comprises at least one diagnostic or therapeutic cation, and/or one or more chelated or chemically bound therapeutic agents, diagnostic agents, or enzymes. In such embodiments, the A subunit may, for example, contain binding sites for tumor associated antigens while the B subunit may contain a binding site for an effector or carrier or a hapten conjugated to an effector or carrier.

The stably tethered structures of the present invention, including their conjugates, are suitable for use in a wide variety of therapeutic and diagnostic applications. For example, the hexavalent constructs based on antibody binding domains can be used for therapy where such a construct is not conjugated to an additional functional agent, in the same manner as therapy using a naked antibody. Alternatively, these stably tethered structures can be derivatized with one or more functional agents to enable diagnostic or therapeutic applications. The additional agent may be covalently linked to the stably tethered structures using conventional conjugation chemistries.

Methods of use of stably tethered structures may include detection, diagnosis and/or treatment of a disease or other medical condition. Such conditions may include, but are not limited to, cancer, cardiovascular disease, atherosclerosis, stroke, neurodegenerative disease, Alzheimer's disease, metabolic diseases, hyperplasia, diabetic retinopathy, macular degeneration, inflammatory bowel disease, Crohn's disease, ulcerative colitis, rheumatoid arthritis, sarcoidosis, asthma, edema, pulmonary hypertension, psoriasis, corneal graft rejection, neovascular glaucoma, Osler-Webber Syndrome, myocardial angiogenesis, plaque neovascularization, restenosis, neointima formation after vascular trauma, telangiectasia, hemophiliac joints, angiofibroma, fibrosis associated with chronic inflammation, lung fibrosis, amyloidosis, organ transplant rejection, deep venous thrombosis or wound granulation.

In particular embodiments, the disclosed methods and compositions may be of use to treat autoimmune disease, such as acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, juvenile diabetes mellitus, Henoch-Schonlein purpura, post-streptococcalnephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

Various embodiments may concern methods of treating inflammatory and immune-dysregulatory diseases, infectious diseases, pathologic angiogenesis or cancer. In this application the stably tethered structures bind to two different targets selected from the group consisting of (A) proinflammatory effectors of the innate immune system, (B) coagulation factors, (C) complement factors and complement regulatory proteins, and (D) targets specifically associated with an inflammatory or immune-dysregulatory disorder or with a pathologic angiogenesis or cancer, wherein the latter target is not (A), (B), or (C). At least one of the targets is (A), (B) or (C). Suitable combinations of targets are described in U.S.

patent application Ser. No. 11/296,432, filed Dec. 8, 2005, entitled "Methods and Compositions for Immunotherapy and Detection of Inflammatory and Immune-Dysregulatory Disease, Infectious Disease, Pathologic Angiogenesis and Cancer," the contents of which are incorporated herein by reference in their entirety. The proinflammatory effector of the innate immune system to which the binding molecules may bind may be a proinflammatory effector cytokine, a proinflammatory effector chemokine or a proinflammatory effector receptor. Suitable proinflammatory effector cytokines include MIF, HMGB-1 (high mobility group box protein 1), TNF-α, IL-1, IL-4, IL-5, IL-6, IL-8, IL-12, IL-15, and IL-18. Examples of proinflammatory effector chemokines include CCL19, CCL21, IL-8, MCP-1, RANTES, MIP-1A, MIP-1B, ENA-78, MCP-1, IP-10, GROB, and Eotaxin. Proinflammatory effector receptors include IL-4R (interleukin-4 receptor), IL-6R (interleukin-6 receptor), IL-13R (interleukin-13 receptor), IL-15R (interleukin-15 receptor) and IL-18R (interleukin-18 receptor).

The binding molecule also may react specifically with at least one coagulation factor, particularly tissue factor (TF) or thrombin. In other embodiments, the binding molecule reacts specifically with at least one complement factor or complement regulatory protein. In preferred embodiments, the complement factor is selected from the group consisting of C3, C5, C3a, C3b, and C5a. When the binding molecule reacts specifically with a complement regulatory protein, the complement regulatory protein preferably is selected from the group consisting of CD46, CD55, CD59 and mCRP.

In certain embodiments, the stably tethered structures may be of use for therapeutic treatment of cancer. It is anticipated that any type of tumor and any type of tumor antigen may be targeted. Exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer.

Tumor-associated antigens that may be targeted include, but are not limited to, carbonic anhydrase IX, A3, antigen specific for A33 antibody, BrE3-antigen, CD1, CD1a, CD3, CD5, CD15, CD16, CD19, CD20, CD21, CD22, CD23, CD25, CD30, CD45, CD74, CD79a, CD80, HLA-DR, NCA95, NCA90, HCG and its subunits, CEA (CEACAM-5), CEACAM-6, CSAp, EGFR, EGP-1, EGP-2, Ep-CAM, Ba 733, HER2/neu, hypoxia inducible factor (HIF), KC4-antigen, KS-1-antigen, KS1-4, Le-Y, macrophage inhibition factor (MIF), MAGE, MUC1, MUC2, MUC3, MUC4, PAM-4-antigen, PSA, PSMA, RS5, S100, TAG-72, p53, tenascin, IL-6, IL-8, insulin growth factor-1 (IGF-1), Tn antigen, Thomson-Friedenreich antigens, tumor necrosis antigens, VEGF, placenta growth factor (P1GF), 17-1A-antigen, an angiogenesis marker (e.g., ED-B fibronectin), an oncogene marker, an oncogene product, and other tumor-associated antigens. Recent reports on tumor associated antigens include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63), each incorporated herein by reference. Particularly preferred embodiments may concern hexavalent, monospecific constructs with binding sites for CD20 or CD22. Other preferred embodiments may concern a hexavalent bispecific construct with binding sites for both CD20 and CD22.

Other embodiments may concern methods for treating a lymphoma, leukemia, or autoimmune disorder in a subject, by administering to the subject one or more dosages of a stably tethered structure, where the binding site of the second precursor bind to a lymphocyte antigen, and where the binding site of the first precursor binds to the same or a different lymphocyte antigen. The binding site or sites may bind a distinct epitope, or epitopes of an antigen selected from the group consisting of CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, CD154, B7, MUC1, Ia, Ii, HM1.24, HLA-DR, tenascin, VEGF, P1GF, ED-B fibronectin, an oncogene, an oncogene product, NCA 66a-d, necrosis antigens, IL-2, T101, TAG, IL-6, MIF, TRAIL-R1 (DR4) and TRAIL-R2 (DR5). The composition may be parenterally administered in a dosage of 20 to 1500 milligrams protein per dose, 20 to 500 milligrams protein per dose, 20 to 100 milligrams protein per dose, or 20 to 1500 milligrams protein per dose, for example.

In other embodiments, the stably tethered structures may be of use to treat infection with pathogenic organisms, such as bacteria, viruses or fungi. Exemplary fungi that may be treated include *Microsporum, Trichophyton, Epidermophyton, Sporothrix schenckii, Cryptococcus neoformans, Coccidioides immitis, Histoplasma capsulatum, Blastomyces dermatitidis* or *Candida albicans*. Exemplary viruses include human immunodeficiency virus (HIV), herpes virus, cytomegalovirus, rabies virus, influenza virus, human papilloma virus, hepatitis B virus, hepatitis C virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus or blue tongue virus. Exemplary bacteria include *Bacillus anthracis, Streptococcus agalactiae, Legionella pneumophilia, Streptococcus pyogenes, Escherichia coli, Neisseria gonorrhoeae, Neisseria meningitidis, Pneumococcus* spp., *Hemophilis influenzae* B, *Treponema pallidum, Lyme disease spirochetes, Pseudomonas aeruginosa, Mycobacterium leprae, Brucella abortus, Mycobacterium tuberculosis* or a *Mycoplasma*.

Although not limiting, in various embodiments, the precursors incorporated into the stably tethered structures may comprise one or more proteins, such as a bacterial toxin, a plant toxin, ricin, abrin, a ribonuclease (RNase), DNase I, Staphylococcal enterotoxin-A, pokeweed antiviral protein, gelonin, diphtherin toxin, *Pseudomonas* exotoxin, *Pseudomonas* endotoxin, Ranpirnase (Rap), Rap (N69Q), PE38, dgA, DT390, PLC, tPA, a cytokine, a growth factor, a soluble receptor component, surfactant protein D, IL-4, sIL-4R, sIL-13R, VEGF$_{121}$, TPO, EPO (erythropoietin), a clot-dissolving agent, an enzyme, a fluorescent protein, sTNFα-R, an avimer, a scFv, a dsFv or a nanobody.

In other embodiments, an anti-angiogenic agent may form part or all of a precursor or may be attached to a stably tethered structure. Exemplary anti-angiogenic agents of use include angiostatin, baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

In still other embodiments, one or more therapeutic agents, such as aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, 2-pyrrolinodoxorubicine (2P-DOX), cyano-morpholino doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, *Pseudomonas exotoxin, Pseudomonas* endotoxin, an antisense oligonucleotide, an interference RNA, or a combination thereof, may be conjugated to or incorporated into a stably tethered structure.

Various embodiments may concern stably tethered structures and methods of use of same that are of use to induce apoptosis of diseased cells. Further details may be found in U.S. Patent Application Publication No. 20050079184, the entire text of which is incorporated herein by reference. Such structures may comprise precursors with binding affinity for an antigen selected from the group consisting of CD2, CD3, CD8, CD10, CD21, CD23, CD24, CD25, CD30, CD33, CD37, CD38, CD40, CD48, CD52, CD55, CD59, CD70, CD74, CD80, CD86, CD138, CD147, HLA-DR, CEA, CSAp, CA-125, TAG-72, EFGR, HER2, HER3, HER4, IGF-1R, c-Met, PDGFR, MUC1, MUC2, MUC3, MUC4, TNFR1, TNFR2, NGFR, Fas (CD95), DR3, DR4, DR5, DR6, VEGF, P1GF, ED-B fibronectin, tenascin, PSMA, PSA, carbonic anhydrase IX, and IL-6. In more particular embodiments, a stably tethered structure of use to induce apoptosis may comprise monoclonal antibodies, Fab fragments, chimeric, humanized or human antibodies or fragments. In preferred embodiments, the stably tethered structure may comprise combinations of anti-CD74×anti-CD20, anti-CD74×anti-CD22, anti-CD22×anti-CD20, anti-CD20×anti-HLA-DR, anti-CD19×anti-CD20, anti-CD20×anti-CD80, anti-CD2× anti-CD25, anti-CD8 X anti-CD25, anti-CD2×anti-CD147, anti-CEACAM5×anti-CD3, anti-CEACAM6×anti-CD3, anti-EGFR×anti-CD3, anti-HER2/neu×anti-CD3, anti-CD20×anti-CD3, anti-CD74×anti-CD3 and anti-CCD22× anti-CD3. In other preferred embodiments, the stably tethered structure may be a monospecific or multispecific anti-CD20, anti-CD22, anti-HLA-DR and/or anti-CD74. The skilled artisan will realize that a multivalent stably tethered structure may comprise multiple antigen-binding moieties that bind, for example, to different epitopes of the CD20 or CD22 antigens, or alternatively may comprise multiple copies of a single antigen-binding moiety that all bind to the same epitope. In more preferred embodiments, the chimeric, humanized or human antibodies or antibody fragments may be derived from the variable domains of LL2 (anti-CD22), LL1 (anti-CD74), L243 (anti-HLA-DR) and A20 (anti-CD20).

BRIEF DESCRIPTION OF THE DRAWINGS

FIG. 1 shows two exemplary DDD sequences. The underlined sequence in DDD1 (SEQ ID NO:1) corresponds to the first 44 amino-terminal residues found in the RIIα of human PKA. DDD2 (SEQ ID NO:2) differs from DDD1 in the two amino acid residues at the N-terminus.

FIG. 2 shows two exemplary AD sequences. The underlined sequence of AD1 (SEQ ID NO:3) corresponds to AKAP-is, which is an optimized RII-selective peptide reported with a Kd of 0.4 nM. Also shown is AD2 (SEQ ID NO:4).

DESCRIPTION OF ILLUSTRATIVE EMBODIMENTS

Figure 3:
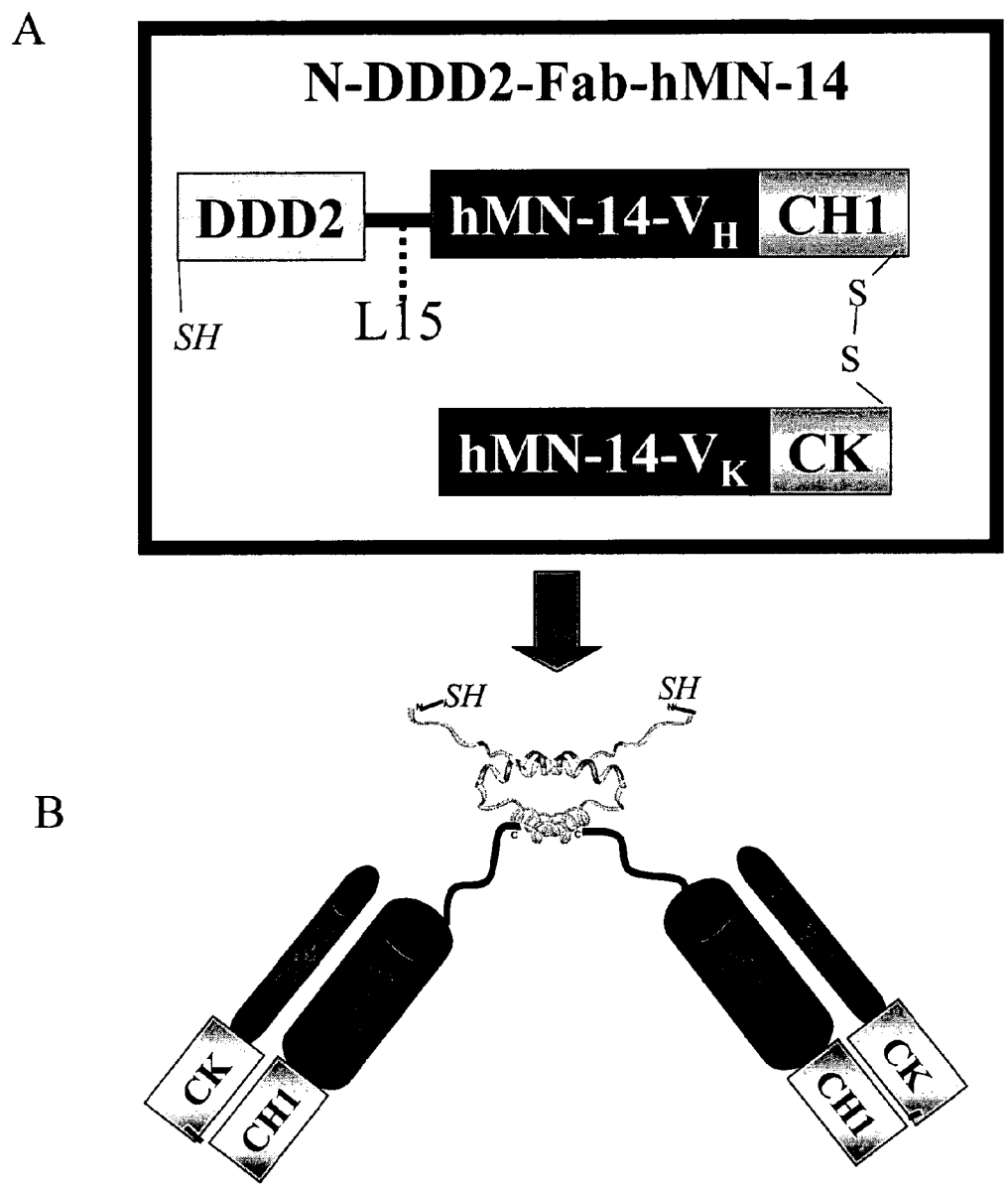
FIG. 3 shows a schematic diagram of N-DDD2-Fab-hMN-14 (A), and the putative $a_2$ structure formed by DDD2-mediated dimerization (B).

All documents, or portions of documents, cited in this application, including but not limited to patents, patent applications, articles, books, and treatises, are hereby expressly incorporated by reference in their entirety.

In certain embodiments, novel stably tethered structures in the format of $a_2b$ and methods for making these complexes are provided. In general, the binary complexes are made up of a noncovalently linked homodimer structure, referred to as A or $a_2$, with which a second structure, referred to as B or b, associates site-specifically. The resulting $a_2b$ structure may be stabilized by non-covalent, or preferably by covalent interaction (e.g., disulfide bonds) between A and B. A is formed from two identical subunits, where each subunit is composed of a precursor linked to a peptide sequence, referred to as the dimerization and docking domain (DDD), which in preferred embodiments is derived from a cAMP-dependent protein kinase (PKA). The DDD domain contained in the subunit associates spontaneously to form a stable homodimer, and this association in turn produces a high affinity binding site for a peptide sequence, referred to as the anchoring domain (AD), which is found, for example, in various A-kinase anchor proteins (AKAPs), and is contained in B. Thus, B is composed of a precursor linked to an AD.

Assembly of the binary complex occurs readily via interaction of the AD peptide with the $(DDD)_2$ binding site. The DDD peptide may be inserted into essentially any polypeptide sequence or tethered to any precursor, provided that such derivatization does not interfere with its ability to dimerize, as well as to bind to the AD peptide. Likewise, the AD peptide may be inserted into essentially any polypeptide sequence or tethered to any precursor provided that such derivatization does not interfere with its binding to the homodimer DDD binding site. This modular approach is highly versatile and can be used to combine essentially any A with any B to form a binary assembly that contains two subunits ($a_2$) derived from the precursor of A and one subunit (b) derived from the precursor of B. Where both precursors of A and B contain an antibody domain that can associate with a second antibody domain to produce an antigen binding site (for example, a Fab or scFv), the resulting $a_2b$ complex is bispecific and trivalent. In some embodiments, the binary complex may be linked, for example via chemical conjugation, to effectors, such as ligands or drugs, to carriers, such as dextran or nanoparticles, or to both effectors and carriers, to allow additional applications enabled by such modifications. In preferred embodiments, variations on this theme may be used to prepare hexameric complexes that are either homohexamers or heterohexamers.

As the stability of the binary complex depends primarily on the binding affinity of the DDD contained in A for the AD contained in B, which is estimated by equilibrium size-exclusion HPLC analysis to be no stronger than 8 nM for two prototype $a_2b$ structures (described in Example 5) formed between a C-terminally fused AD1 construct (h679-Fab-AD1, described in Example 3) to a C- or N-terminally fused DDD1 construct (C-DDD1-Fab-hMN-14 or N-DDD1-Fab-hMN-14, both described in Example 4), covalently linking A and B contained in the $a_2b$ complex would prevent undesirable dissociation of the individual subunits, thereby facilitating in vivo applications. To stabilize the binary complex, cysteine residues may be introduced onto both the DDD and AD sequences at strategic positions to enable the formation of disulfide linkages between the DDD and AD. Other methods or strategies may be applied to effect the formation of a stabilized complex via crosslinking $a_2$ and b. For example, the constituent subunits can be covalently linked to each other in a less specific way with lower efficiency using glutaraldehyde or the PICUP method. Other known methods of covalent cross-linking may also be used.

Definitions

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

A "dimerization and docking domain (DDD)" refers to a peptide sequence that allows the spontaneous dimer formation of two homomonomers containing the DDD sequence. The resulting homodimer contains a docking site within the DDD sequence for an anchoring domain. Although exemplary DDD sequences may be obtained from cAMP-dependent protein kinase, other known DDD sequences may be utilized.

An "anchoring domain (AD)" is a peptide sequence that has binding affinity for a dimerized DDD sequence. Although exemplary AD sequences may be derived from any of the A-kinase anchor proteins (AKAPs), other known AD sequences may be utilized.

The term "precursor" is used according to its plain and ordinary meaning of a substance from which a more stable, definitive or end product is formed.

A "binding molecule," "binding moiety" or "targeting molecule," as used herein, is any molecule that can specifically bind to a target molecule, cell, complex and/or tissue. A binding molecule may include, but is not limited to, an antibody or a fragment, analog or mimic thereof, an avimer, an aptamer or a targeting peptide.

An "antibody," as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion or analog of an immunoglobulin molecule, like an antibody fragment.

An "antibody fragment" is a portion of an antibody such as $F(ab)_2$, $F(ab')_2$, Fab, Fv, sFv and the like. Regardless of structure, an antibody fragment binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units (CDR) consisting of the amino acid residues that mimic the hypervariable region.

An "effector" is an atom, molecule, or compound that brings about a chosen result. An effector may include a therapeutic agent and/or a diagnostic agent.

A "therapeutic agent" is an atom, molecule, or compound that is useful in the treatment of a disease. Examples of therapeutic agents include antibodies, antibody fragments, drugs, toxins, enzymes, nucleases, hormones, immunomodulators, antisense oligonucleotides, small interfering RNA (siRNA), chelators, boron compounds, photoactive agents, dyes, and radioisotopes. Other exemplary therapeutic agents and methods of use are disclosed in U.S. Patent Publication Nos. 20050002945, 20040018557, 20030148409 and 20050014207, each incorporated herein by reference.

A "diagnostic agent" is an atom, molecule, or compound that is useful in diagnosing a disease. Useful diagnostic agents include, but are not limited to, radioisotopes, dyes (such as with the biotin-streptavidin complex), contrast agents, fluorescent compounds or molecules, and enhancing agents (e.g., paramagnetic ions) for magnetic resonance imaging (MRI).

An "immunoconjugate" is a conjugate of a binding molecule (e.g., an antibody component) with an atom, molecule, or a higher-ordered structure (e.g., with a carrier, a therapeutic agent, or a diagnostic agent).

A "naked antibody" is an antibody that is not conjugated to any other agent.

A "carrier" is an atom, molecule, or higher-ordered structure that is capable of associating with a therapeutic or diagnostic agent to facilitate delivery of such agent to a targeted cell. Carriers may include lipids (e.g., amphiphilic lipids that are capable of forming higher-ordered structures), polysaccharides (such as dextran), or other higher-ordered structures, such as micelles, liposomes, or nanoparticles.

As used herein, the term "antibody fusion protein" is a recombinantly produced antigen-binding molecule in which two or more of the same or different scFv or antibody fragments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds to one such epitope, for example a diabody with two binding site reactive with the same antigen. The fusion protein may comprise a single antibody component, a multivalent or multispecific combination of different antibody components, or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

An antibody or immunoconjugate preparation, or a composition described herein, is said to be administered in a "therapeutically effective amount" if the amount administered is physiologically significant. An agent is physiologically significant if its presence results in a detectable change in the physiology of a recipient mammal. In particular embodiments, an antibody preparation is physiologically significant if its presence invokes an antitumor response or mitigates the signs and symptoms of an autoimmune disease state. A physiologically significant effect could also be the evocation of a humoral and/or cellular immune response in the recipient mammal leading to growth inhibition or death of target cells. A "therapeutically effective amount" is not limited to the amount of an agent that produces the most preferred effect in a subject, but may refer to an amount that results in any of the possible known effects of the agent on a subject, cell, tissue or organ.

Methods to Generate a Stably Tethered Assembly of Modular Subunits

The disclosed methods and compositions provide a platform technology for generating a stably tethered assembly of modular subunits. One embodiment concerns a stably tethered binary complex formed from two defined components, A and B, which are preferably produced separately. However, in alternative embodiments both A and B may be produced together, for example by transfecting a single cell line with a vector that codes for both A and B, or with two different vectors that separately encode A and B. Separate production is preferred where A and B are both Fab fragments, as otherwise co-production would result in heterogenous products due to light chain scrambling.

In some embodiments, A, consisting of two identical subunits ($a_2$), is combined with B, consisting of one subunit (b), to form an assembly in the configuration of $a_2b$. The association of A and B is site-specific and spontaneous, due to the strong binding interaction between the DDD and AD sequences that are built into A and B, respectively. Both A and B can be any entity and the precursor of A to which the DDD is linked may be different from or the same as the precursor of B to which the AD is linked. In the latter case, the resulting $a_2b$ complex, referred to as $a_3$, is composed of three subunits, each containing the same precursor but linked to both DDD and AD.

The modular nature of the claimed methods and compositions allows the combination of any A with any B. There is essentially no limit on the types of precursors that can be attached to or incorporated into A and B, so long as they do not interfere with the dimerization of DDD or the binding of DDD to AD. When constructed by recombinant engineering, A and B can be produced independently in a different host cell, purified, and stored (or alternatively produced in the same host cell as discussed above). However, the need for purification of A and B prior to assembly is not absolutely required. Cell extracts or culture media containing A and B may be mixed directly under appropriate conditions to effect the formation of the binary complex, which may then be stabilized by disulfide linkages upon oxidation, and purified afterwards. In certain applications, it may be desirable to conjugate B, after purification and before combining with A, with effectors or carriers. Alternatively, it may be desirable to conjugate A, after purification and before combining with B, with effectors or carriers. It may also be desirable to modify both A and B with effectors or carriers before combining. In addition, conjugation of the $a_2b$ complex with effectors or carriers may also be desirable in certain applications. Where A and B are produced in the same host cell, they may spontaneously assemble into an $a_2b$ complex.

Preferred embodiments take advantage of the specific protein/protein interactions between cAMP-dependent protein kinase (PKA) regulatory subunits and A-kinase anchor proteins (AKAP) anchoring domains that occur in nature. PKA was first reported in 1968 (See Walsh et al., *J. Biol. Chem.* 243:3763-65 (1968)). The structure of the holoenzyme, which consists of two catalytic subunits that are held in an inactive form by a regulatory (R) subunit dimer, was elucidated in the mid 1970s (See Corbin et al., *J. Biol. Chem.* 248:1813-21 (1973)). Two types of R subunits (RI and RII) are found and each has α and β isoforms. The R subunits have been isolated only as stable dimers and the dimerization domain has been shown to consist of the first 44 amino-terminal residues (See Hausken et al., *J. Biol. Chem.* 271:29016-22 (1996)). The signaling specificity of PKA, which is a broad-spectrum serine/threonine kinase, is achieved through compartmentalization of the holoenzyme via docking proteins called A-kinase anchor proteins (AKAPs) (Scott et al., *J. Biol. Chem.* 265:21561-66 (1990)).

Figure 7:
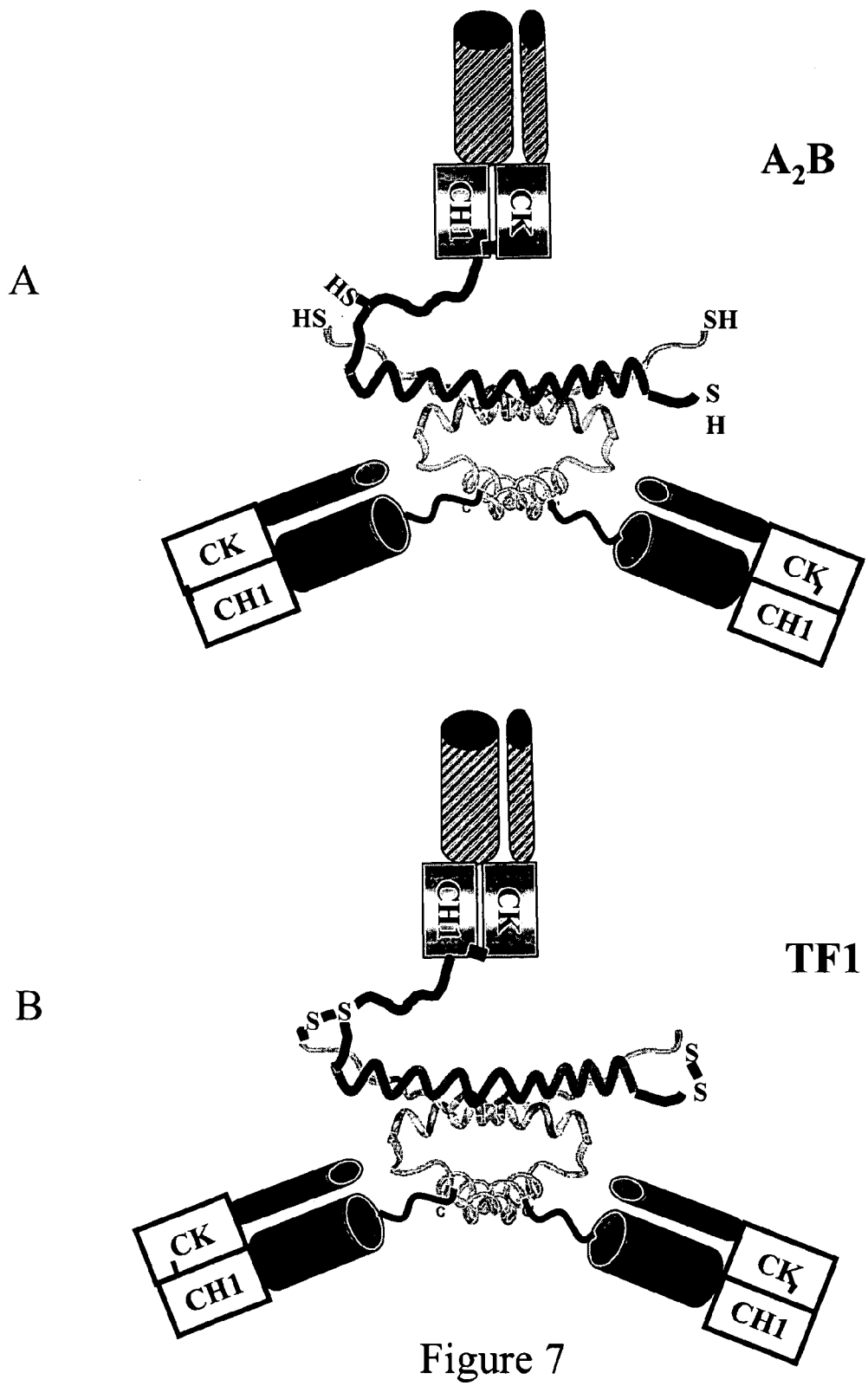
FIG. 7 shows a schematic representation of (A) the noncovalent $a_2b$ complex that is formed upon mixing N-DDD2-Fab-hMN-14 and h679-Fab-AD2 under reducing conditions, and (B) the covalent TF1 structure formed by disulfide bridges.

The first AKAP, microtubule-associated protein-2, was characterized in 1984 (Lohmann et al., *Proc. Natl. Acad. Sci USA.* 81:6723-27 (1984)). To date, more than 50 structurally diverse AKAPs have been identified in species ranging from yeast to humans (See Wong et al., *Nat Rev Mol Cell Biol.* 12:959-70 (2004)). The PKA anchoring domain of AKAPs is an amphipathic helix of 14-18 residues (See Carr et al. *J. Biol. Chem.* 266:14188-92 (1991)). The amino acid sequences of the PKA anchoring domain are quite diverse among AKAPs and the binding affinities for RII dimers ranges from 2-90 nM while the binding affinities for RI dimers is about 100-fold weaker (See Alto et al. *Proc. Natl. Acad. Sci USA.* 100:4445-50 (2003)). The anchoring domain binds to a hydrophobic surface on RII dimers formed by the first amino terminal 23 residues of RII (Colledge et al., *Trends Cell Biol.* 6:216-21 (1999)). Thus, the RII dimerization domain and AKAP binding domain are both located within the same 44 amino acid sequence. Further, AKAPs will only bind to RII dimers, not monomers. A structural model of this interaction is shown in FIG. 7.

The non-covalent complexes formed via the interaction of the DDD and AD sequences may be covalently stabilized to allow in vivo applications. This may be achieved through the introduction of cysteine residues into both the DDD and AD sequences at strategic positions (as those shown for DDD2 and AD2) to facilitate the formation of disulfide linkages. Alternatively, other known types of covalent cross-linking may be employed.

The two components of the binary complex (A and B), when produced by recombinant engineering, may be synthesized within the same host cell, or more preferably in two separate host cell lines. An expression vector directing the synthesis of A will contain the DNA sequences of a polypeptide of interest (A) fused to a sequence encoding the DDD of a PKA R-subunit, such as DDD1 or DDD2, which may consist of the first 30 or more amino acids of RIα, RIβ, RIIα, RIIβ, or any natural or synthetic functional analog. The DDD can be coupled to the amino-terminal or carboxyl terminal end of A, either directly or preferably with a spacer containing an appropriate length and composition of amino acid residues. Alternatively, the DDD can be positioned internally within the fusion protein provided that the binding activity of the DDD and the desired activity of the polypeptide fusion partner are not compromised. Upon synthesis, the A/DDD fusion protein will form exclusively a stable homodimer with DDD1, or predominantly a stable homotetramer with DDD2. Methods for forming stable homohexamers or heterohexamers are discussed below in the Examples.

A second expression cassette directing the synthesis of B, which can be in the same vector that directs the synthesis of A or preferably an independent one, will contain the DNA sequences of a polypeptide of interest (B) fused to a sequence encoding an anchoring domain (AD), such as AD1 or AD2, which can be derived from any AKAP protein, or a natural or synthetic analog as disclosed in US 2003/0232420A1, incorporated herein by reference. The AD can be coupled to the amino-terminal or carboxyl terminal end of B, either directly or preferably with a spacer containing appropriate length or composition of amino acid residues. Mixing the B/AD2 fusion protein (b) with the A/DDD2 fusion protein (predominantly $a_4$) in the presence of a disulfide reducing agent results in a binary complex consisting of $a_2b$, which is subsequently stabilized with the formation of disulfide bonds facilitated by the addition of a suitable oxidizing agent such as dimethyl sulfoxide (DMSO).

The modular nature of the subunits allows the combination of any DDD2-polypeptide dimer with any AD2-polypeptide. Stocks of a variety of modular subunits can be maintained individually either as purified products or unpurified cell culture supernatants and subsequently combined to obtain various $a_2b$ structures when desired.

A further embodiment is that effectors, such as drugs or chelators, or carriers, such as dextran or nanoparticles, may be coupled using appropriate conjugation chemistry to either A or B following its purification. Alternatively, such modifications can be made to the structure after its formation and purification, or to both A and B before mixing.

Stably Tethered Assembly of Modular Subunits Derived from Recombinant Antibody Binding Domains The disclosed methods and compositions are useful for providing recombinant antibody-based multivalent binding structures, which can be monospecific or bispecific. For example, the DDD2 sequence can be fused to a single chain Fv to obtain monospecific binding structures. More generally, a DDD sequence can be fused to an antibody variable domain that can associate with a complementary antibody variable domain to form an antigen-binding site. For example, the DDD1 or DDD2 sequence can be fused to an antibody sequence containing a $V_H$ domain and a CH1 domain (Fd/DDD), or alternatively to a $V_L$ domain and a CL domain (L/DDD). The Fd/DDD or L/DDD can then associate with a complementary L or Fd, respectively, to form a Fab/DDD and further a dimer of Fab/DDD1 or a tetramer/dimer of Fab/DDD2.

Similarly, an AD sequence like AD2 can be fused to a single chain Fv, or more generally, to an antibody sequence containing a VH domain and a CH1 domain (Fd/AD2), which forms a Fab/AD2 when paired with a cognate L-chain. Alternatively, an AD sequence like AD2 may be fused to an antibody sequence containing a VL domain and a CL domain, which forms a Fab/AD2 when paired with a cognate Fd chain. Mixing a tetramer/dimer of Fab/DDD2 with Fab/AD2 followed by reduction and oxidation results in a stably tethered assembly of a trivalent binding structure, which can be monospecific or bispecific.

The $V_H$ and $V_L$ regions of the binding structure may be derived from a "humanized" monoclonal antibody or from a human antibody. Alternatively, the $V_H$ and/or $V_L$ regions may comprise a sequence derived from human antibody fragments isolated from a combinatorial immunoglobulin library. See, for example, Barbas et al., METHODS: A companion to Methods in Enzymology 2: 119 (1991), and Winter et al., Ann. Rev. Immunol. 12: 433 (1994). Cloning and expression vectors that are useful for producing a human immunoglobulin phage library can be obtained, for example, from STRATAGENE Cloning Systems (La Jolla, Calif.).

The human antibody $V_H$ or $V_L$ sequence may be derived from a human monoclonal antibody produced in a mouse. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7: 13 (1994), Lonberg et al., Nature 368: 856 (1994), and Taylor et al., Int. Immun. 6: 579 (1994).

General Methods for the Production of Recombinant Fusion Proteins Containing Antibody Fragments Nucleic acid sequences encoding antibody fragments that recognize specific epitopes can be obtained by techniques that are well known in the art. For example, hybridomas secreting antibodies of a desired specificity can be used to obtain antibody-encoding DNA that can be prepared using known techniques, for example, by PCR or by traditional cDNA cloning techniques. Alternatively, Fab' expression libraries or antibody phage display libraries can be constructed to screen for antibody fragments having a desired specificity.

The nucleic acid encoding the antibody fragment can then be ligated, directly or via a sequence that encodes a peptide spacer, to nucleic acid encoding either the DDD or the AD. Methods of producing nucleic acid sequences encoding these types of fusion proteins are well known in the art and are further provided in the Examples.

In another embodiment, additional amino acid residues may be added to either the N- or C-terminus of the modular subunit composed of A/DDD or B/AD, where the exact fusion site may depend on whether the DDD or the AD are attached to the N- or C-terminus (or at an internal position). The additional amino acid residues may comprise a peptide tag, a signal peptide, a cytokine, an enzyme (for example, a pro-drug activating enzyme), a hormone, a toxin, a peptide drug, a membrane-interacting peptide, or other functional proteins.

Methods for producing recombinant proteins in a desired host cell are well known in the art. To facilitate purification, the stably tethered structures may contain suitable peptide tags, such as the FLAG sequence or the poly-HIS sequence, to facilitate their purification with a relevant affinity column.

A exemplary expression system suitable for expressing the constituent subunits of the stably tethered structures is the pdHL2 vector, which has an amplifiable murine dhfr gene that allows selection and amplification by methotrexate treatment. See Gillies et al., J. Immunol. Methods 125:191 (1989). The pdHL2 vector provides independent expression of two genes that are separately controlled by two metallothionine promoters and IgH enhancers.

Suitable host cells or cell lines for the expression of the constituent subunits of the stably tethered structures of are known to one skilled in the art. The use of a human host cell would enable any expressed molecules to be modified with human glycosylation patterns. However, there is no indication that a human host cell is essential or preferred for the disclosed methods.

As an illustration, a murine myeloma cell line such as Sp2/0 can be transfected by electroporation with linearized pdHL2 vector that encodes a constituent subunit of the stably tethered structures. Selection can be initiated 48 hours after transfection by incubating cells with medium containing 0.05-0.1 µM methotrexate. The clones selected can then be amplified by a stepwise increase in methotrexate concentration up to 5 µM.

Conjugates of the Stably Tethered Structures

Additional moieties can be conjugated to the stably tethered structures described above. For example, drugs, toxins, radioactive compounds, enzymes, hormones, cytotoxic proteins, chelates, cytokines, and other functional agents may be conjugated to one or more subunits of the stably tethered structures. Conjugation can be via, for example, covalent attachments to amino acid residues containing amine, carboxyl, thiol or hydroxyl groups in the side-chains. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the stably tethered structures preferably does not significantly affect the activity of each subunit contained in the unmodified structures. Conjugation can be carried out separately to the modular subunits and the subunits then allowed to assemble into the stably tethered construct, or alternatively conjugation may be carried out using the fully formed stably tethered construct or any intermediate in the formation of the stably tethered construct. In addition, cytotoxic or other agents may be first coupled to a polymeric carrier, which is then conjugated to a stably tethered structure. For this method, see Ryser et al., Proc. Natl. Acad. Sci. USA, 75:3867-3870, 1978; U.S. Pat. No. 4,699,784 and U.S. Pat. No. 4,046,722, which are incorporated herein by reference.

The conjugates described herein can be prepared by various methods known in the art. For example, a stably tethered structure can be radiolabeled with $^{131}$I and conjugated to a lipid, such that the resulting conjugate can form a liposome. The liposome may incorporate one or more therapeutic agents (e.g., a drug such as FUdR-dO) or diagnostic agents. Alternatively, in addition to the carrier, a stably tethered structure may be conjugated to $^{131}$I (e.g., at a tyrosine residue) and a drug (e.g., at the epsilon amino group of a lysine residue), and the carrier may incorporate an additional therapeutic or diagnostic agent. Therapeutic and diagnostic agents may be covalently associated with one or more than one subunit of the stably tethered structures.

The formation of liposomes and micelles is known in the art. See, e.g., Wrobel and Collins, Biochimica et Biophysica Acta (1995), 1235: 296-304; Lundberg et al., J. Pharm. Pharmacol. (1999), 51:1099-1105; Lundberg et al., Int. J. Pharm. (2000), 205:101-108; Lundberg, J. Pharm. Sci. (1994), 83:72-75; Xu et al., Molec. Cancer Ther. (2002), 1:337-346; Torchilin et al., Proc. Nat'l. Acad. Sci., U.S.A. (2003), 100: 6039-6044; U.S. Pat. No. 5,565,215; U.S. Pat. No. 6,379,698; and U.S. 2003/0082154.

Nanoparticles or nanocapsules formed from polymers, silica, or metals, which are useful for drug delivery or imaging, have been described as well. See, e.g., West et al., Applications of Nanotechnology to Biotechnology (2000), 11:215-217; U.S. Pat. No. 5,620,708; U.S. Pat. No. 5,702,727; and U.S. Pat. No. 6,530,944. The conjugation of antibodies or binding molecules to liposomes to form a targeted carrier for therapeutic or diagnostic agents has been described. See, e.g., Bendas, Biodrugs (2001), 15:215-224; Xu et al., Mol. Cancer Ther (2002), 1:337-346; Torchilin et al., Proc. Nat'l. Acad. Sci. U.S.A (2003), 100:6039-6044; Bally, et al., J. Liposome Res. (1998), 8:299-335; Lundberg, Int. J. Pharm. (1994), 109:73-81; Lundberg, J. Pharm. Pharmacol. (1997), 49:16-21; Lundberg, Anti-cancer Drug Design (1998), 13: 453-461. See also U.S. Pat. No. 6,306,393; U.S. Ser. No. 10/350,096; U.S. Ser. No. 09/590,284, and U.S. Ser. No. 60/138,284, filed Jun. 9, 1999. All these references are incorporated herein by reference.

A wide variety of diagnostic and therapeutic agents can be advantageously used to form the conjugates of the stably tethered structures, or may be linked to haptens that bind to a recognition site on the stably tethered structures. Diagnostic agents may include radioisotopes, enhancing agents for use in MRI or contrast agents for ultrasound imaging, and fluorescent compounds. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509).

In order to load a stably tethered structure with radioactive metals or paramagnetic ions, it may be necessary to first react it with a carrier to which multiple copies of a chelating group for binding the radioactive metals or paramagnetic ions have been attached. Such a carrier can be a polylysine, polysaccharide, or a derivatized or derivatizable polymeric substance having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and the like known to be useful for this purpose. Carriers containing chelates may be coupled to the stably tethered structure using standard chemistries in a way to minimize aggregation and loss of immunoreactivity.

Other, more unusual, methods and reagents that may be applied for preparing such conjugates are disclosed in U.S. Pat. No. 4,824,659, which is incorporated by reference herein in its entirety. Particularly useful metal-chelate combinations include 2-benzyl-DTPA and its monomethyl and cyclohexyl analogs, used with diagnostic isotopes in the general energy range of 60 to 4,000 keV. Some useful diagnostic nuclides may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In. The same chelates complexed with non-radioactive metals, such as manganese, iron and gadolinium, are useful for MRI, when used along with the stably tethered structures and carriers described herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used.

Therapeutic agents include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and proapoptotic agents, particularly doxorubicin, methotrexate, taxol, CPT-11, camptothecans, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art, and may be conjugated to the stably tethered structures described herein using methods that are known in the art.

Another class of therapeutic agents consists of radionuclides that emit α-particles (such as $^{212}$Pb, $^{212}$Bi, $^{213}$Bi, $^{211}$At, $^{223}$Ra, $^{225}$Ac), β articles (such as $^{32}$P, $^{33}$P, $^{47}$Sc, $^{67}$Cu, $^{67}$Ga, $^{89}$Sr, $^{90}$Y, $^{111}$Ag, $^{125}$I, $^{131}$I, $^{142}$Pr, $^{153}$Sm, $^{161}$Tb, $^{166}$Ho, $^{166}$Dy, $^{177}$Lu, $^{186}$Re, $^{188}$Re, $^{189}$Re), or Auger electrons (such as $^{111}$In, $^{125}$I, $^{67}$Ga, $^{191}$Os, $^{193m}$Pt, $^{195m}$Pt, $^{195m}$Hg). The stably tethered structures may be labeled with one or more of the above radionuclides using methods as described for the diagnostic agents.

A suitable peptide containing a detectable label (e.g., a fluorescent molecule), or a cytotoxic agent, (e.g., a radioiodine), can be covalently, non-covalently, or otherwise associated with the stably tethered structures. For example, a therapeutically useful conjugate can be obtained by incorporating a photoactive agent or dye onto the stably tethered structures. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Jori et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photo-activated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529. Endoscopic or laparoscopic applications are also contemplated. Endoscopic methods of detection and therapy are described in U.S. Pat. No. 4,932,412; U.S. Pat. No. 5,525,338; U.S. Pat. No. 5,716,595; U.S. Pat. No. 5,736,119; U.S. Pat. No. 5,922,302; U.S. Pat. No. 6,096,289; and U.S. Pat. No. 6,387,350, which are incorporated herein by reference in their entirety.

In certain embodiments, the novel constructs and methods disclosed herein are useful for targeted delivery of RNAi for therapeutic intervention. The delivery vehicle can be a stably tethered structure with an internalizing antibody binding domain fused to human protamine (peptide of ~50 amino acid residues) as its precursor. An example of an $a_2$ construct of use would be VH-CH1-hP1-DDD1//VL-CL or VH-CH1-hP2-DDD1//VL-CL, where hP1 and hP2 are human protamine 1 and human protamine 2, respectively; both capable of forming stable DNA complexes for in vivo applications (Nat Biotechnol. 23: 709-717, 2005; Gene Therapy. 13: 194-195, 2006). An example of an $a_4$ construct of use would be VH-CH1-hP1-DDD2//VL-CL or VH-CH1-hP2-DDD2//VL-CL, which would provide four active Fab fragments, each carrying a human protamine for binding to RNAi. The multivalent complex will facilitate the binding to and receptor-mediated internalization into target cells, where the noncovalently bound RNAi is dissociated in the endosomes and released into cytoplasm. As no redox chemistry is involved, the existence of 3 intramolecular disulfide bonds in hP1 or hP2 does not present a problem. In addition to delivery of RNAi, these constructs may also be of use for targeted delivery of therapeutic genes or DNA vaccines. Another area of use is to apply the technology for producing intrabodies, which is the protein analog of RNAi in terms of function.

Therapeutic Agents

Pharmaceutical Compositions

In some embodiments, a stably tethered structure and/or one or more other therapeutic agents may be administered to a subject, such as a subject with cancer. Such agents may be administered in the form of pharmaceutical compositions. Generally, this will entail preparing compositions that are essentially free of impurities that could be harmful to humans or animals. One skilled in the art would know that a pharmaceutical composition can be administered to a subject by various routes including, for example, orally or parenterally, such as intravenously.

In certain embodiments, an effective amount of a therapeutic agent must be administered to the subject. An "effective amount" is the amount of the agent that produces a desired effect. An effective amount will depend, for example, on the efficacy of the agent and on the intended effect. For example, a lesser amount of an antiangiogenic agent may be required for treatment of a hyperplastic condition, such as macular degeneration or endometriosis, compared to the amount required for cancer therapy in order to reduce or eliminate a solid tumor, or to prevent or reduce its metastasizing. An effective amount of a particular agent for a specific purpose can be determined using methods well known to those in the art.

Chemotherapeutic Agents

In certain embodiments, chemotherapeutic agents may be administered. Anti-cancer chemotherapeutic agents of use include, but are not limited to, 5-fluorouracil, bleomycin, busulfan, camptothecins, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, methotrexate, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. Chemotherapeutic agents of use against infectious organisms include, but are not limited to, acyclovir, albendazole, amantadine, amikacin, amoxicillin, amphotericin B, ampicillin, aztreonam, azithromycin, bacitracin, bactrim, Batrafen®, bifonazole, carbenicillin, caspofungin, cefaclor, cefazolin, cephalosporins, cefepime, ceftriaxone, cefotaxime, chloramphenicol, cidofovir, Cipro®, clarithromycin, clavulanic acid, clotrimazole, cloxacillin, doxycycline, econazole, erythrocycline, erythromycin, flagyl, fluconazole, flucytosine, foscarnet, furazolidone, ganciclovir, gentamycin, imipenem, isoniazid, itraconazole, kanamycin, ketoconazole, lincomycin, linezolid, meropenem, miconazole, minocycline, naftifine, nalidixic acid, neomycin, netilmicin, nitrofurantoin, nystatin, oseltamivir, oxacillin, paromomycin, penicillin, pentamidine, piperacillin-tazobactam, rifabutin, rifampin, rimantadine, streptomycin, sulfamethoxazole, sulfasalazine, tetracycline, tioconazole, tobramycin, tolciclate, tolnaftate, trimethoprim sulfamethoxazole, valacyclovir, vancomycin, zanamir, and zithromycin.

Chemotherapeutic agents and methods of administration, dosages, etc., are well known to those of skill in the art (see for example, the "Physicians Desk Reference", Goodman & Gilman's "The Pharmacological Basis of Therapeutics" and in "Remington's Pharmaceutical Sciences", incorporated herein by reference in relevant parts). Some variation in dosage will necessarily occur depending on the condition of the subject being treated. The person responsible for administration will, in any event, determine the appropriate dose for the individual subject.

Hormones

Corticosteroid hormones can increase the effectiveness of other chemotherapy agents, and consequently, they are frequently used in combination treatments. Prednisone and dexamethasone are examples of corticosteroid hormones. Progestins, such as hydroxyprogesterone caproate, medroxyprogesterone acetate, and megestrol acetate, have been used in cancers of the endometrium and breast. Estrogens such as diethylstilbestrol and ethinyl estradiol have been used in cancers such as prostate cancer. Antiestrogens such as tamoxifen have been used in cancers such as breast cancer. Androgens such as testosterone propionate and fluoxymesterone have also been used in treating breast cancer.

Angiogenesis Inhibitors

In certain embodiments, anti-angiogenic agents, such as angiostatin, baculostatin, canstatin, maspin, anti-VEGF antibodies, anti-P1GF peptides and antibodies, anti-vascular growth factor antibodies, anti-Flk-1 antibodies, anti-Flt-1 antibodies and peptides, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Immunomodulators

As used herein, the term "immunomodulator" includes cytokines, stem cell growth factors, lymphotoxins and hematopoietic factors, such as interleukins, colony-stimulating factors, interferons (e.g., interferons-α, -β and -γ) and the stem cell growth factor designated "S1 factor." Examples of suitable immunomodulator moieties include IL-2, IL-6, IL-10, IL-12, IL-18, IL-21, interferon-gamma, TNF-alpha, and the like.

The term "cytokine" is a generic term for proteins or peptides released by one cell population which act on another cell as intercellular mediators. As used broadly herein, examples of cytokines include lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines. Similarly, the terms immunomodulator and cytokine overlap in their respective members.

Radioisotope Therapy and Radioimmunotherapy

In some embodiments, the peptides and/or proteins may be of use in radionuclide therapy or radioimmunotherapy methods (see, e.g., Govindan et al., 2005, *Technology in Cancer Research & Treatment*, 4:375-91; Sharkey and Goldenberg, 2005, *J. Nucl. Med.* 46:115S-127S; Goldenberg et al. (J Clin Oncol 2006; 24:823-834), "Antibody Pre-targeting Advances Cancer Radioimmunodetection and Radioimmunotherapy," each incorporated herein by reference.) In specific embodiments, stably tethered structures may be directly tagged with a radioisotope of use and administered to a subject. In alternative embodiments, radioisotope(s) may be administered in a pre-targeting method as discussed above, using a haptenic peptide or ligand that is radiolabeled and injected after administration of a bispecific stably tethered structure that localizes at the site of elevated expression in the diseased tissue.

Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

For example, $^{67}$Cu, considered one of the more promising radioisotopes for radioimmunotherapy due to its 61.5 hour half-life and abundant supply of beta particles and gamma rays, can be conjugated to a protein or peptide using the chelating agent, p-bromoacetamido-benzyl-tetraethylamine-tetraacetic acid (TETA). Alternatively, $^{90}$Y, which emits an energetic beta particle, can be coupled to a peptide, antibody, fusion protein, or fragment thereof, using diethylenetriamine-pentaacetic acid (DTPA).

Additional potential radioisotopes include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

In another embodiment, a radiosensitizer can be used. The addition of the radiosensitizer can result in enhanced efficacy. Radiosensitizers are described in D. M. Goldenberg (ed.), CANCER THERAPY WITH RADIOLABELED ANTIBODIES, CRC Press (1995), which is incorporated herein by reference in its entirety.

The stably tethered structure that has a boron addend-loaded carrier for thermal neutron activation therapy will normally be effective in some ways. However, it will be advantageous to wait until non-targeted immunoconjugate clears before neutron irradiation is performed. Clearance can be accelerated using an antibody that binds to the ligand. See U.S. Pat. No. 4,624,846 for a description of this general principle. For example, boron addends such as carboranes, can be attached to antibodies. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the antibody. After administration of the conjugate, a boron addend is activated by thermal neutron irradiation and converted to radioactive atoms which decay by alpha-emission to produce highly toxic, short-range effects.

Kits

Various embodiments may concern kits containing components suitable for treating or diagnosing diseased tissue in a patient. Exemplary kits may contain at least one stably tethered structure. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more separate containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

Formulation and Administration

The stably tethered structures, including their conjugates, may be further formulated to obtain compositions that include one or more pharmaceutically suitable excipients, one or more additional ingredients, or some combination of these. These can be accomplished by known methods to prepare pharmaceutically useful dosages, whereby the active ingredients (i.e., the stably tethered structures or conjugates), are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parental injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, including oral administration, are also contemplated.

Formulated compositions comprising stably tethered structures can be used for intravenous administration via, for example, bolus injection or continuous infusion. Compositions for injection can be presented in unit dosage form, e.g., in ampules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The pH of the solution should be in the range of pH 5 to 9.5, preferably pH 6.5 to 7.5. The formulation thereof should be in a solution having a suitable pharmaceutically acceptable buffer such as phosphate, tris (hydroxymethyl)aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included. Systemic administration of the formulated composition is typically made every two to three days or once a week if a humanized form of the antibody is used as a template for the stably tethered structures. Alternatively, daily administration is useful. Usually administration is by either intramuscular injection or intravascular infusion.

The compositions may be administered to a mammal subcutaneously or by other parenteral routes. Moreover, the administration may be by continuous infusion or by single or multiple boluses. Methods useful for the antibodies or immunoconjugates can be applied to the compositions described herein. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of the active ingredient that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule. In various exemplary embodiments, dosages may range from 100 to 500 mg, from 200 to 1000 mg, from 500 to 2000 mg, from 100 to 250 mg, from 250 to 500 mg, from 500 to 1000 mg, or other ranges known for antibody, antibody fragment or fusion protein administration.

Pharmaceutical methods employed to control the duration of action of immunoconjugates or antibodies may be applied to the formulated compositions described herein. Control release preparations can be achieved through the use of biocompatible polymers to complex or adsorb the immunoconjugate or naked antibody, for example, matrices of poly(ethylene-co-vinyl acetate) and matrices of a polyanhydride copolymer of a stearic acid dimer and sebacic acid. See Sherwood et al., Bio/Technology (1992), 10: 1446. The rate of release of an immunoconjugate or antibody from such a matrix depends upon the molecular weight of the immunoconjugate or antibody, the amount of immunoconjugate, antibody within the matrix, and the size of dispersed particles. See Saltzman et al., Biophys. J (1989), 55: 163; Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

For purposes of therapy, the composition is administered to a mammal in a therapeutically effective amount. A suitable subject for the therapeutic and diagnostic methods disclosed herein is usually a human, although a non-human animal subject, such as mammals, cats, dogs, horses, pigs, goats, cows, alpacas, llamas or sheep is also contemplated.

The stably tethered structures disclosed herein are particularly useful in the method of treating autoimmune disorders, disclosed in pending U.S. Ser. No. 09/590,284 filed on Jun. 9, 2000 entitled "Immunotherapy of Autoimmune Disorders using Antibodies that Target B-Cells," which is incorporated in its entirety by reference. Compositions containing such binding structures are preferably administered intravenously or intramuscularly at a dose of 20-5000 mg. Administration may also be intranasal or by other nonparenteral routes. The compositions may also be administered via microspheres, liposomes or other microparticulate delivery systems placed in certain tissues including blood.

The compositions may be administered by aerosol to achieve localized delivery to the lungs. Either an aqueous aerosol or a nonaqueous (e.g., fluorocarbon propellent) suspension could be used. Sonic nebulizers preferably are used in preparing aerosols to minimize exposing the stably tethered structure in the compositions to shear, which can result in its degradation and loss of activity.

In general, the dosage of administration will vary depending upon such factors as the patient's age, weight, height, sex, general medical condition and previous medical history. Preferably, a saturating dose of the stably tethered structure is administered to a patient.

Typically, it is desirable to provide the recipient with a dosage that is in the range of from about 50 to 500 milligrams of the stably tethered structure, although a lower or higher dosage also may be administered as circumstances dictate. Examples of dosages include 20 to 1500 milligrams protein per dose, 20 to 500 milligrams protein per dose, 20 to 100 milligrams protein per dose, 20 to 1000 milligrams protein per dose, 100 to 1500 milligrams protein per dose. In the embodiments where the composition comprises a radionuclide, the dosage may be measured by millicurries. In the case of $^{90}$Y, the dosage may be between 15 and 40 mCi, 10 and 30 mCi, 20 and 30 mCi, or 10 and 20 mCi.

A stably tethered structure linked to a radionuclide is particularly effective for microbial therapy. After it has been determined that the stably tethered structure is localized at one or more infectious sites in a subject, higher doses of the labeled composition, generally from 20 mCi to 150 mCi per dose for $^{131}$I, 5 mCi to 30 mCi per dose for $^{90}$Y, or 5 mCi to 20 mCi per dose of $^{186}$Re, each based on a 70 kg patient weight, are injected. Injection may be intravenous, intraarterial, intralymphatic, intrathecal, or intracavitary (i.e., parenterally), and may be repeated. It may be advantageous for some therapies to administer multiple, divided doses, thus providing higher microbial toxic doses without usually effecting a proportional increase in radiation of normal tissues.

Chemotherapeutic agents, antimicrobial agents, cytokines, granulocyte-colony stimulating factor (G-CSF), granulocyte macrophage-colony stimulating factor (GM-CSF), erythropoietin, thrombopoietin, and the like, which are not chemically linked to the stably tethered structures, may be administered before, during, or after the administration of the composition. Alternatively, such agents may be attached to the stably tethered structures.

The stably tethered structures in the $a_2b$ format are particularly suitable as pretargeting agents. A exemplary structure will consist of two scFv or Fab subunits as $a_2$ that bind bivalently to a target tissue or cell, and one scFv or Fab subunit as b that binds to a hapten. Such a bispecific trivalent structure is first administered to a subject, optionally followed by a clearing agent, followed by administration of an agent in which the hapten is bound to a functional agent, such as a detectable label for diagnosis, or a therapeutic agent for methods of treatment. The skilled artisan will be aware that other known methods of using bispecific antibodies may also be practiced using the stably tethered structures. These methods of diagnosis and therapy may be applied in essentially any circumstance in which antibody-based agents have been used for diagnosis or therapy. As discussed below, bispecific hexavalent stably tethered structures may also be utilized for the same purposes as bispecific trivalent structures.

Uses for Treatment and Diagnosis: Applications not Involving Pretargeting

The stably tethered structures, including their conjugates, are suitable for use in a wide variety of therapeutic and diagnostic applications that utilize antibodies or immunoconjugates and do not require pretargeting. For example, the trivalent structures can be used for therapy as a "naked" construct, i.e. in an embodiment where such a structure is not conjugated to an additional functional agent, in the same manner as therapy using a naked antibody. Alternatively, the stably tethered structures can be derivatized with one or more functional agents to enable diagnostic or therapeutic applications. The additional agent may be covalently linked to the stably tethered structures as described above.

Also contemplated is the use of radioactive and non-radioactive diagnostic agents, which are linked to the stably tethered structures. Suitable non-radioactive diagnostic agents are those used for magnetic resonance imaging (MRI), computed tomography (CT) or ultrasound. MRI agents include, for example, non-radioactive metals, such as manganese, iron and gadolinium, which are complexed with suitable chelates such as 2-benzyl-DTPA and its monomethyl and cyclohexyl analogs. See U.S. Ser. No. 09/921,290 filed on Oct. 10, 2001, which is incorporated in its entirety by reference.

The stably tethered structures may be labeled with a radioisotope useful for diagnostic imaging. Suitable radioisotopes may include those in the energy range of 60 to 4,000 KeV, or more specifically, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{45}$Ti, $^{111}$In, $^{123}$I, $^{124}$I, $^{125}$I, $^{131}$I, $^{154-158}$Gd, $^{177}$Lu, $^{32}$P, $^{188}$Re, and the like, or a combination thereof. See, e.g., U.S. patent application entitled "Labeling Targeting Agents with Gallium-68"-Inventors G. L. Griffiths and W. J. McBride, and U.S. Provisional Application No. 60/342,104, which discloses positron emitters, such as $^{18}$F, $^{68}$Ga, $^{94m}$Tc, and the like, for imaging purposes; incorporated entirely by reference). Detection can be achieved, for example, by single photon emission computed tomography (SPECT), or positron emission tomography (PET). The application also may be for intraoperative diagnosis to identify occult neoplastic tumors.

In another embodiment the stably tethered structures may be labeled with one or more radioactive isotopes useful for killing neoplastic or other rapidly dividing cells, which include β-emitters (such as $^{32}$P, $^{33}$P, $^{47}$Sc, $^{67}$Cu, $^{67}$Ga, $^{89}$Sr, $^{90}$Y, $^{111}$Ag, $^{125}$I, $^{131}$I, $^{142}$Pr, $^{153}$Sm, $^{161}$Tb, $^{166}$Ho, $^{166}$Dy, $^{177}$Lu, $^{186}$Re, $^{188}$Re, $^{189}$Re), Auger electron emitters such as $^{111}$In, $^{125}$I, $^{67}$Ga, $^{191}$Os, $^{193m}$Pt, $^{195m}$Pt, $^{195m}$Hg), α-emitters (such as $^{212}$Pb, $^{212}$Bi, $^{213}$Bi, $^{211}$At, $^{223}$Ra, $^{225}$Ac), or a combination thereof.

The stably tethered structures may be used for MRI by linking to one or more image enhancing agents, which may include complexes of metals selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III). Similarly, the stably tethered structures may be used for ultrasound imaging by linking to one or more image enhancing agents currently on the market. U.S. Pat. No. 6,331,175 describes MRI technique and the preparation of antibodies conjugated to an MRI enhancing agent and is incorporated in its entirety by reference.

A functional protein, such as a toxin, may be present in the stably tethered structures in several ways. For example, a functional protein may serve as the precursor for either component of the binary complex by fusing to either DDD2 or AD2, which is then combined with a targeting entity, composed of, for example, Fab/AD2 or Fab/DDD2, respectively. Alternatively, a functional protein can be fused to a targeting structure to serve as a precursor for A, and the resulting A is optionally paired with a suitable B. Toxins that may be used in this regard include ricin, abrin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin. (See, e.g., Pastan. et al., Cell (1986), 47:641, and Goldenberg, C A—A Cancer Journal for Clinicians (1994), 44:43. Additional toxins suitable for use herein are known to those of skill in the art and are disclosed in U.S. Pat. No. 6,077,499, which is incorporated in its entirety by reference. Other functional proteins of interest include various cytokines, clot-dissolving agents, enzymes, and fluorescent proteins.

Also provided is a method of treating a neoplastic disorder in a subject, by administering to the subject a "naked" stably tethered binding structure as described above, where at least one of the antigen binding sites binds to an antigen selected from the group consisting of carbonic anydrase IX, alpha-fetoprotein, A3, antigen specific for A33 antibody, Ba 733, BrE3-antigen, CA125, carcinoembryonic antigen (CEACAM5), CEACAM6, CD1, CD1a, CD3, CD5, CD15, CD16, CD19, CD20, CD21, CD22, CD23, CD25, CD30, CD33, CD38, CD45, CD74, CD79a, CD80, CD138, colon-specific antigen-p (CSAp), EGFR, EGP-1, EGP-2, Flt-1, Flt-3, folate receptor, HER2/neu, HLA-DR, human chorionic gonadrotropin, Ia, IL-2, IL-6, IL-8, insulin-like growth factor, KC4-antigen, KS-1, KS1-4, Le(y), macrophage-inhibition factor (MIF), MAGE, MUC1, MUC2, MUC3, MUC4, NCA66, NCA95, NCA90, necrosis antigens, antigen bound by p53, PAM-4 antibody, placental growth factor, prostatic acid phosphatase, PSA, PSMA, RS5, S100, T101, TAC, TAG-72, Tn antigen, Thomson-Friedenreich antigens, tumor necrosis antigens, tenascin, TRAIL receptors, ED-B fibronectin, VEGF, 17-1A-antigen, an angiogenesis marker, an oncogene marker or an oncogene product. Antibodies against TRAIL receptors, such as TRAIL-R1 and TRAIL-R2, are well known in the art. (See, e.g., Georgakis et al., Br. J. Haematol. 2005, 130:501-510; Mori et al., FEBS Lett. 2005, 579:5379-84.) Such antibodies or fragments may be used alone or in combination with anti-TAA antibodies for cancer therapy.

The neoplastic disorder may be selected from the group consisting of carcinomas, sarcomas, gliomas, lymphomas, leukemias, and melanomas. Exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid, non-Hodgkin's lymphoma, ovarian cancer, pancreatic cancer, glioma, melanoma, liver cancer, prostate cancer, and urinary bladder cancer.

Also provided is a method for treating a B-cell malignancy, or B-cell immune or autoimmune disorder in a subject, by administering to the subject one or more dosages of a therapeutic composition containing a stably tethered binding structure as described above and a pharmaceutically acceptable carrier, where each antigen binding site binds a distinct epitope of CD19, CD20, CD22 or IL-17. The therapeutic composition may be parenterally administered in a dosage of 20 to 1500 milligrams protein per dose, or 20 to 500 milligrams protein per dose, or to 100 milligrams protein per dose. The subject may receive repeated parenteral dosages of 20 to 100 milligrams protein per dose, or repeated parenteral dosages of 20 to 1500 milligrams protein per dose. In these methods, a sub-fraction of the binding structure may be labeled with a radioactive isotope, such as $^{32}P$, $^{33}P$, $^{47}Sc$, $^{67}Cu$, $^{67}Ga$, $^{90}Y$, $^{111}Ag$, $^{111}In$, $^{125}I$, $^{131}I$, $^{142}Pr$, $^{153}Sm$, $^{161}Tb$, $^{166}Dy$, $^{166}Ho$, $^{177}Lu$, $^{186}Re$, $^{188}Re$, $^{189}Re$, $^{212}Pb$, $^{212}Bi$, $^{213}Bi$, $^{211}At$, $^{223}Ra$, and $^{225}Ac$, or a combination thereof.

Also provided is a method for detecting or diagnosing a B-cell malignancy, or B-cell immune or autoimmune disorder in a subject, by administering to the subject a diagnostic composition containing a stably tethered binding structure, where each antigen binding site binds a distinct epitope of CD19, CD20, CD22 or IL-17, a pharmaceutically acceptable carrier, and a radionuclide selected from the group consisting of $^{18}F$, $^{52}Fe$, $^{62}Cu$, $^{64}Cu$, $^{67}Cu$, $^{67}Ga$, $^{68}Ga$, $^{86}Y$, $^{89}Zr$, $^{94m}Tc$, $^{94}Tc$, $^{99m}Tc$, $^{111}In$, $^{123}I$, $^{124}I$, $^{125}I$, $^{131}I$, $^{1254-158}Gd$, $^{177}Lu$, $^{32}P$, $^{45}Ti$ and $^{188}Re$, or a combination thereof. Detection may be by SPECT or PET as described above. The application also may be for intraoperative diagnosis to identify occult neoplastic tumors.

Also provided is a method for detecting or diagnosing a B-cell malignancy, or B-cell immune or autoimmune disorder in a subject, by administering to the subject a diagnostic composition containing a stably tethered binding structure, where each antigen binding site binds a distinct epitope of CD19, CD20, CD22 or IL-17, a pharmaceutically acceptable carrier, and one or more image enhancing agents for use in magnetic resonance imaging (MRI). The image enhancing agent may be selected from those described above.

Also provided is a method of diagnosing and/or treating a non-neoplastic disease or disorder, by administering to a subject suffering from the disease or disorder a stably tethered binding structure, where a detectable label or therapeutic agent is attached, and where one or more of the antigen binding sites is specific for a marker substance of the disease or disorder. The disease or disorder may be caused by a fungus, such as Microsporum, *Trichophyton, Epidermophyton, Sporothrix schenckii, Cryptococcus neoformans, Coccidioides immitis, Histoplasma capsulatum, Blastomyces dermatitidis*, and *Candida albicans*, or a virus, such as human immunodeficiency virus (HIV), herpes virus, cytomegalovirus, rabies virus, influenza virus, human papilloma virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, and blue tongue virus.

The disease or disorder may be caused by a bacterium, such as Anthrax *bacillus, Streptococcus agalactiae, Legionella pneumophilia, Streptococcus pyogenes, Escherichia coli, Neisseria gonorrhoeae, Neisseria meningitidis, Pneumococcus, Hemophilis influenzae* B, *Treponema pallidum*, Lyme disease spirochetes, *Pseudomonas aeruginosa, Mycobacterium leprae, Brucella abortus*, and *Mycobacterium tuberculosis*, or a *Mycoplasma*. The disease or disorder may be caused by a parasite, such as malaria.

The disease or disorder may be an autoimmune disease, such as acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, parnphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, and fibrosing alveolitis.

The disease or disorder may be myocardial infarction, ischemic heart disease, or atherosclerotic plaques, or graft rejection, or Alzheimer's disease, or caused by atopic tissue. The disease or disorder may be inflammation caused by accretion of activated granulocytes, monocytes, lymphoid cells or macrophages at the site of inflammation, and where the inflammation is caused by an infectious agent.

In addition, cells expressing a particular receptor or over-expressing a receptor may be targeted using a stably tethered structure wherein either the A or B component contains a ligand for the receptor that directs binding of the structure to the cell(s) bearing the receptor. Therapeutic or diagnostic agents can be fused or conjugated to one or more of the subunits of the structure to permit methods of diagnosis and therapy.

Uses for Treatment and Diagnosis: Applications Involving Pretargeting

Pretargeting is a multistep process originally developed to resolve the slow blood clearance of directly targeting antibodies, which contributes to undesirable toxicity to normal tissues, in particular, bone marrow. With pretargeting, a radionuclide or other therapeutic agent is attached to a small compound that is cleared within minutes from the blood. The pretargeting agent, which is capable of recognizing the small radiolabeled compound in addition to the target antigen, is administered first, and the radiolabeled compound is administered at a later time when the pretargeting agent is sufficiently cleared from the blood.

Pretargeting methods have been developed to increase the target:background ratios of detection or therapeutic agents. Examples of pre-targeting and biotin/avidin approaches are described, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. No. 6,077,499; U.S. Ser. No. 09/597,580; U.S. Ser. No. 10/361, 026; U.S. Ser. No. 09/337,756; U.S. Ser. No. 09/823,746; U.S. Ser. No. 10/116,116; U.S. Ser. No. 09/382,186; U.S. Ser. No. 10/150,654; U.S. Pat. No. 6,090,381; U.S. Pat. No. 6,472, 511; U.S. Ser. No. 10/114,315; U.S. Provisional Application No. 60/386,411; U.S. Provisional Application No. 60/345, 641; U.S. Provisional Application No. 60/3328,835; U.S. Provisional Application No. 60/426,379; U.S. Ser. No. 09/823,746; U.S. Ser. No. 09/337,756; U.S. Provisional Application No. 60/342,103; and U.S. Pat. No. 6,962,702, all of which are incorporated herein by reference.

In a specific, non-limiting example, a pretargeting agent based on the stably tethered structure contains two identical tumor antigen binding sites that are specific for CEA and the third binding site is specific for the hapten, histamine-succinyl-glycine (HSG). In alternative embodiments, a different tumor-associated antigen may be targeted, with the same or a different hapten.

For pretargeting applications, the targetable agent may be a liposome with a bivalent HSG-peptide covalently attached to the outside surface of the liposome lipid membrane. The liposome may be gas filled for contrast or may be filled with a therapeutic or diagnostic agent.

A pretargeting method of treating or diagnosing a disease or disorder in a subject is provided by (1) administering to the subject a bispecific trivalent or hexavalent binding structure described above, where the first antigen binding sites are directed to a marker substance, or marker substances specific for the disorder, and the second antigen binding sites are directed to a targetable construct containing a bivalent hapten; (2) optionally administering to the subject a clearing composition, and allowing the composition to clear the binding structure from circulation; and (3) administering to the subject the targetable construct containing a bivalent hapten, where the targetable construct further contains one or more chelated or chemically bound therapeutic or diagnostic agents. The disease or disorder may be as described above.

Also provided is a method of antibody dependent enzyme prodrug therapy (ADEPT) by (1) administering to a patient with a neoplastic disorder a binding structure as above, where the structure contains a covalently attached enzyme capable of activating a prodrug, (2) optionally administering to the subject a clearing composition, and allowing the composition to clear the binding structure from circulation, and (3) administering the prodrug to the patient.

Additional Uses

In general, the stably tethered structures may be substituted for antibody-based agents that have shown efficacy for treating cancers or non-cancer diseases. It is well known that radioisotopes, drugs, and toxins can be conjugated to antibodies or antibody fragments which specifically bind to markers produced by or associated with cancer cells, and that such antibody conjugates can be used to target the radioisotopes, drugs or toxins to tumor sites to enhance their therapeutic efficacy and minimize side effects. Examples of these agents and methods are reviewed in Wawrzynczak and Thorpe (in Introduction to the Cellular and Molecular Biology of Cancer, L. M. Franks and N. M. Teich, eds, Chapter 18, pp. 378-410, Oxford University Press. Oxford, 1986), in Immunoconjugates. Antibody Conjugates in Radioimaging and Therapy of Cancer (C. W. Vogel, ed., 3-300, Oxford University Press, N.Y., 1987), and in Dillman, R. O. (CRC Critical Reviews in Oncology/Hematology 1:357, CRC Press, Inc., 1984). See also Pastan et al., Cell (1986), 47:641; Vitetta et al., Science (1987), 238:1098-1104; and Brady et al., Int. J. Rad. Oncol. Biol. Phys. (1987), 13:1535-1544.

In certain embodiments, multivalent stably tethered structures may be of use in treating and/or imaging normal or diseased tissue and organs, for example using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Additional methods are described in U.S. application Ser. No. 09/337,756 filed Jun. 22, 1999 and in U.S. application Ser. No. 09/823,746, filed Apr. 3, 2001. Such imaging can be conducted by direct labeling of the stably tethered structure, or by a pretargeted imaging method, as described in Goldenberg et al, "Antibody Pretargeting Advances Cancer Radioimmunodetection and Radiotherapy," (in press, J. Clin. Oncol.), see also U.S. Patent Publication Nos. 20050002945, 20040018557, 20030148409 and 20050014207, each incorporated herein by reference.

Other examples of the use of immunoconjugates for cancer and other forms of therapy have been disclosed, inter alia, in the following U.S. Pat. Nos. 4,331,647, 4,348,376, 4,361,544, 4,468,457, 4,444,744, 4,460,459, 4,460,561 4,624,846, 4,818,709, 4,046,722, 4,671,958, 4,046,784, 5,332,567, 5,443,953, 5,541,297, 5,601,825, 5,635,603, 5,637,288, 5,677,427, 5,686,578, 5,698,178, 5,789,554, 5,922,302, 6,187,287, and 6,319,500. These methods are also applicable to the methods disclosed herein by the substitution of the engineered antibodies and antibodies of the previous methods with the present stably tethered structures.

In some embodiments, the stably tethered structures disclosed and claimed herein may be of use in radionuclide therapy or radioimmunotherapy methods (see, e.g., Govindan et al., 2005, Technology in Cancer Research & Treatment, 4:375-91; Sharkey and Goldenberg, 2005, J. Nucl. Med. 46:115 S-127S; Goldenberg et al. (in press, J. Clin. Oncol.), "Antibody Pretargeting Advances Cancer Radioimmunodetection and Radioimmunotherapy," each incorporated herein by reference.)

In another embodiment, a radiosensitizer can be used in combination with a naked or conjugated stably tethered structure, antibody or antibody fragment. For example, the radiosensitizer can be used in combination with a radiolabeled stably tethered structure. The addition of the radiosensitizer can result in enhanced efficacy when compared to treatment with the radiolabeled stably tethered structure alone. Radiosensitizers are described in D. M. Goldenberg (ed.), CANCER THERAPY WITH RADIOLABELED ANTIBODIES, CRC Press (1995), which is incorporated herein by reference in its entirety.

The stably tethered structures for use in any of the claimed methods, may be associated or administered with antimicrobial agents.

The stably tethered structure, for use in any of the claimed methods, may be associated or administered with cytokines and immune modulators. These cytokines and immune modulators, include, at least, interferons of alpha, beta and gamma, and colony stimulating factors.

The disclosed methods may also be of use for stimulating the immune response in a patient using the stably tethered structures. In one embodiment, the stably tethered structure may comprise an antigen binding site (ABS) of an anti-idiotype antibody. Such a stably tethered structure may mimic an epitope of a tumor-associated antigen to enhance the body's immune response.

The stably tethered structure may be used for many immunological procedures currently employing antibodies. These procedures include the use of anti-idiotypic antibodies and epitope conjugated antibodies to boost the immune system. See U.S. Pat. Nos. 5,798,100; 6,090,381; and 6,132,718. Anti-idiotypic antibodies are also employed as vaccines against cancers and infectious diseases. See U.S. Pat. Nos. 6,440,416 and 6,472,511. Further, a polyspecific trimeric or hexameric binding structure may bind multidrug transporter proteins and overcome multidrug resistant phenotype in cells and pathogens. The antibodies in these methods may be replaced by the stably tethered structure disclosed herein.

Various embodiments concern methods for treating a symptom of an autoimmune disorder. In the method, a stably tethered structure is administered to a patient with an autoimmune disorder, which may be admixed with a pharmaceutically acceptable carrier before administration. The stably tethered structure of this method should contain at least one ABS with binding specificity to a B-cell or T-cell antigen epitope. The B cell antigen may be CD22 and the epitope may be epitope A, epitope B, epitope C, epitope D and epitope E of CD22 and others. The B cell-associated antigen may also be another cell antigen such as CD 19, CD20, HLA-DR and CD74. The T-cell antigens may include CD25. In certain embodiments, stably tethered structures of use to treat autoimmune disease may be selected to bind to IL-17.

The ABS may contain a sequence of subhuman primate, murine monoclonal antibody, chimeric antibody, humanized antibody, or human origin. For example, the ABS may be of humanized LL2 (anti-CD22), humanized LL1 (anti-CD74) or humanized A20 (anti-CD20) monoclonal antibody origin.

The administration may be parenteral with dosages from 20 to 2000 mg per dose. Administration may be repeated until a degree of reduction in symptoms is achieved.

The patients who may be treated by the claimed methods include any animal including humans. Preferably, the animal is a mammal such as humans, primates, equines, canines and felines.

The stably tethered structures may be used for the treatment of diseases that are resistant or refractory towards systemic chemotherapy. These include various viral, fungal, bacterial and protozoan infections, as well as particular parasitic infections. Viral infections include those caused by influenza virus, herpes virus, Epstein-Barr virus and cytomegalovirus, rabies virus (Rhabdoviridae), papilloma virus, and papovavirus, all of which are difficult to treat with systemic antibiotic/cytotoxic agents. Use of multivalent binding structures may provide a higher avidity for the target viruses, resulting in significantly higher therapeutic index. Targeted radioimmunotherapy using conjugates of the stably tethered structures that are labeled with radioisotopes (and including boron addends activatable with thermal neutron) offers a new approach to antiviral therapy.

Protozoans that may be treated by the methods described in the invention include, e.g., Plasmodia (especially *P. falciparum*, the malaria parasite), *Toxoplasma gondii* (the toxoplasmosis infectious agent), Leishmaniae (infectious agent in leishmaniasis), and *Escherichia histolytica*. Detection and treatment of malaria in its various stages may be significantly enhanced using the stably tethered structures. Monoclonal antibodies (mAbs) that bind to sporozoite antigens are known. However, since sporozoite antigens are not shared by blood stage parasites, the use of such mAbs against sporozoite antigens for targeting is limited to a relatively short period of time in which the sporozoites are free in the circulation, just after injection and prior to development in the host's hepatocytes. Thus, it is preferable to use a mixture of mAbs that can target more than one parasite stage of a protozoan (such as *P. falciparum*), which may be achieved with one or more than one stably tethered structure having multiple specificity. The use of conjugates may offer further advantages for imaging, e.g. with $^{99m}$Tc, or for therapy, e.g., with $^{211}$At or an antimalarial drug, e.g., pyrimethamine.

Toxoplasmosis is also resistant to systemic chemotherapy. It is not clear whether mAbs that bind specifically to *T. gondii*, or natural, host antibodies, can play a role in the immune response to toxoplasmosis but, as in the case of malarial parasites, appropriately targeted stably tethered structures may be effective vehicles for the delivery of therapeutic agents.

Schistosomiasis, a widely prevalent helminth infection, is initiated by free-swimming cercariae that are carried by some freshwater snails. As in the case of malaria, there are different stages of cercariae involved in the infectious process. Stably tethered structures that bind to a plurality of stages of cercariae, optionally to a plurality of epitopes on one or more thereof, and preferably in the form of a polyspecific composite, can be conjugated to an imaging or therapy agent for effective targeting and enhanced therapeutic efficacy.

Stably tethered structures that bind to one or more forms of *Trypanosoma cruzi*, the causative agent of Chagas' disease, can be made and used for detection and treatment of this microbial infection. Stably tethered structures which react with a cell-surface glycoprotein or other surface antigens on differentiation stages of the trypanosome are suitable for directing imaging and therapeutic agents to sites of parasitic infiltration in the body.

Another very difficult infectious organism to treat by available drugs is the leprosy bacillus (*Mycobacterium leprae*). Stably tethered structures that specifically bind to a plurality of epitopes on the surface of *M. leprae* can be made and may be used, alone or in combination, to target imaging agents and/or antibiotic/cytotoxic agents to the *bacillus*.

Helminthic parasitic infections, e.g., Strongyloidosis and Trichinosis, themselves relatively refractory towards chemotherapeutic agents, are suitable targets for stably tethered structures. Their diagnosis and therapy may be achieved by appropriate stably tethered structures or conjugates that bind specifically to one or, preferably, to a plurality of epitopes on the parasites.

Antibodies are available or can easily be raised that specifically bind to most of the microbes and parasites responsible for the majority of infections in humans. Many of these have been used previously for in vitro diagnostic purposes and may be incorporated into stably tethered structures as components of antibody conjugates to target diagnostic and therapeutic agents to sites of infection. Microbial pathogens and invertebrate parasites of humans and mammals are organisms with complex life cycles having a diversity of antigens expressed at various stages thereof. Therefore, targeted treatment can best be effected when stably tethered structures which recognize antigen determinants on the different forms are made and used in combination, either as mixtures or as polyspecific conjugates, linked to the appropriate therapeutic modality. The same principle applies to using the reagents comprising stably tethered structures for detecting sites of infection by attachment of imaging agents, e.g., radionuclides and/or MRI enhancing agents.

Other embodiments concern methods of intraoperatively identifying diseased tissues by administering an effective amount of a stably tethered structure and a targetable construct where the stably tethered structure comprises at least one antigen binding site that specifically binds a targeted tissue and at least one other antigen binding site that specifically binds the targetable construct; and wherein said at least one antigen binding site is capable of binding to a complementary binding moiety on the target cells, tissues or pathogen or on a molecule produced by or associated therewith.

Still other embodiments concern methods for the endoscopic identification of diseased tissues, in a subject, by administering an effective amount of a stably tethered structure and administering a targetable construct. The stably tethered structure comprises at least one antigen binding site that specifically binds a targeted tissue and at least one antigen binding site that specifically binds the targetable construct; and wherein said at least one antigen binding site shows specific binding to a complementary binding moiety on the target cells, tissues or pathogen or on a molecule produced by or associated therewith.

An alternative method of detection of use is wireless capsule endoscopy, using an ingested capsule camera/detector of the type that is commercially available from, for example, Given Imaging (Norcross Ga.). Certain embodiments concern methods for the endoscopic identification of diseased tissues, in a subject, by administering an effective amount of a stably tethered structure, and administering a targetable construct. In this embodiment, the stably tethered structure comprises at least one antigen binding site that specifically binds a targeted tissue and at least one antigen binding site that specifically binds the targetable construct; and wherein said at least one antigen binding site shows specific binding to a complementary binding moiety on the target cells, tissues or pathogen or on a molecule produced by or associated therewith.

Alternative embodiments concern methods for the intravascular identification of diseased tissues, in a subject by administering an effective amount of a stably tethered structure and a targetable construct. The stably tethered structure comprises at least one antigen binding site (ABS) that specifically binds a complementary binding moiety on the target cells, tissues or pathogen or on a molecule produced by or associated with the cell, tissues or pathogen, and at least one ABS that specifically binds a targetable construct. The target tissue may be a normal tissue such as thyroid, liver, heart, ovary, thymus, parathyroid, endometrium, bone marrow, lymph nodes or spleen.

Some embodiments concern kits for practicing the claimed methods. The kit may include a targetable construct. The targetable construct may be labeled by any of the agents described as suitable for targetable constructs above. Further, the targetable construct may be unlabeled but the kit may comprise labeling reagents to label the targetable construct. The labeling reagents, if included, may contain the label and a crosslinker. The kit may also contain a stably tethered structure comprising at least one ABS specific for the targetable construct and at least one ABS specific for a targetable tissue. The kit may optionally contain a clearing composition to remove stably tethered structure from circulation.

Targets for Stably Tethered Structures

Additional disclosure concerning targets for stably tethered structures are disclosed in provisional U.S. Patent Application Ser. No. 60/634,076, "Methods and Compositions for Immunotherapy and Detection of Inflammatory and Immune-dysregulatory Disease, Infectious Disease, Pathologic Angiogenesis and Cancer," by Goldenberg et al., filed Dec. 9, 2004, the entire text of which is incorporated herein by reference.

In some embodiments, the stably tethered structures claimed herein react specifically with two different targets. The different targets may include, but are not limited to, proinflammatory effectors of the innate immune system, coagulation factors, complement factors and complement regulatory proteins, targets specifically associated with an inflammatory or immune-dysregulatory disorder, with an infectious pathogen, or with a pathologic angiogenesis or cancer, wherein this latter class of target is not a proinflammatory effector of the immune system or a coagulation factor. Thus, in certain embodiments the stably tethered structure contains at least one binding specificity related to the diseased cell, pathologic angiogenesis or cancer, or infectious disease, and at least one specificity to a component of the immune system, such as a receptor or antigen of B cells, T cells, neutrophils, monocytes and macrophages, and dendritic cells, or modulators of coagulation, such as thrombin or tissue factor, or proinflammatory cytokines, such as IL-1, IL-6, IL-10, HMGB-1, and MIF.

The stably tethered structure can be naked, but can also be conjugated to a diagnostic imaging agent (e.g., isotope, radiological contrast agent,) or to a therapeutic agent, including a radionuclide, a boron compound, an immunomodulator, a peptide a hormone, a hormone antagonist, an enzyme, oligonucleotides, an enzyme inhibitor, a photoactive therapeutic agent, a cytotoxic agent, an angiogenesis inhibitor, and a combination thereof. The binding of the stably tethered structure to a target can down-regulate or otherwise affect an immune cell function, but the stably tethered structure also may bind to other targets that do not directly affect immune cell function. For example, an anti-granulocyte antibody, such as against CD66 or CEACAM6 (e.g., NCA90 or NCA95), can be used to target granulocytes in infected tissues, and can also be used to target cancers that express CEACAM6.

In one embodiment, the therapeutic agent is an oligonucleotide. For example, the oligonucleotide can be an antisense oligonucleotide, or a double stranded interfering RNA (RNAi) molecule. The oligonucleotide can be against an oncogene like bcl-2 or p53. An antisense molecule inhibiting bcl-2 expression is described in U.S. Pat. No. 5,734,033. It may be conjugated to, or form the therapeutic agent portion of a stably tethered structure. Alternatively, the oligonucleotide may be administered concurrently or sequentially with the stably tethered structure.

In another embodiment, the therapeutic agent is a boron addend, and treatment entails irradiation with thermal or epithermal neutrons after localization of the therapeutic agent. The therapeutic agent also may be a photoactive therapeutic agent, particularly one that is a chromogen or a dye.

In a preferred embodiment, the therapeutic agent is a cytotoxic agent, such as a drug or toxin. Also preferred, the drug is selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzymes, enzyme inhibitors, epipodophyllotoxins, platinum coordination complexes, vinca alkaloids, substituted ureas, methyl hydrazine derivatives, adrenocortical suppressants, hormone antagonists, endostatin, taxols, SN38, camptothecins, doxorubicins and their analogs, antimetabolites, alkylating agents, antimitotics, antiangiogenic, apoptotoic agents, methotrexate, CPT-11, and a combination thereof.

In another preferred embodiment, the therapeutic agent is a toxin derived from a source selected from the group comprising an animal, a plant, and a microbial source. Preferred toxins include ricin, abrin, alpha toxin, saporin, ribonuclease (RNase), DNase I, Staphylococcal enterotoxin-A, pokeweed antiviral protein, gelonin, diphtherin toxin, *Pseudomonas* exotoxin, and *Pseudomonas* endotoxins.

The therapeutic agent may be an immunomodulator, such as a cytokine, a stem cell growth factor, a lymphotoxin, a hematopoietic factor, a colony stimulating factor (CSF), an interferon (IFN), a stem cell growth factor, erythropoietin, thrombopoietin and a combination thereof said lymphotoxin is tumor necrosis factor (TNF). The hematopoietic factor may be an interleukin (IL), the colony stimulating factor may be a granulocyte-colony stimulating factor (G-CSF) or granulocyte macrophage-colony stimulating factor (GM-CSF)), the interferon may be interferons-α, β or γ, and the stem cell growth factor may be S1 factor. Alternatively, the immunomodulator may comprise IL-1, IL-2, IL-3, IL-6, IL-10, IL-12, IL-17, IL-18, IL-21, interferon-γ, TNF-α, or a combination thereof.

Preferred therapeutic radionuclides include beta, alpha, and Auger emitters, with a keV range of 80-500 keV. Exemplary therapeutic radioisotopes include $^{32}$P, $^{33}$P, $^{47}$Sc, $^{125}$I, $^{131}$I, $^{86}$Y, $^{90}$Y, $^{186}$Re, $^{188}$Re, $^{189}$Re, $^{64}$Cu, $^{67}$Cu, $^{67}$Ga, $^{111}$Ag, $^{142}$Pr, $^{153}$Sm, $^{161}$Tb, $^{166}$Dy, $^{166}$Ho, $^{177}$Lu, $^{198}$Au, $^{211}$At, $^{212}$Pb, $^{212}$Bi, $^{213}$Bi, $^{223}$Ra and $^{225}$Ac, and combinations thereof. Exemplary photoactive therapeutic agents are selected from the group comprising chromogens and dyes.

Still preferred, the therapeutic agent is an enzyme selected from the group comprising malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

Various examples of therapeutic agent peptides are known in the art and any such known agent may be used. Exemplary therapeutic peptides include, but are not limited to, hormones, growth factors, cytokines, chemokines, binding peptides, blocking peptides, toxins, angiogenic factors, anti-angiogenic factors, antibiotics, anti-cancer peptides, anti-viral peptides, pharmaceutical peptides, enzymes, agonists, antagonists, hematopoietic agents such as erythropoietin and many other clinically useful compounds.

The stably tethered structure may bind specifically to at least one proinflammatory effector cytokine, proinflammatory effector chemokine, or proinflammatory effector receptor. Proinflammatory effector cytokines to which the stably tethered structure may bind include, but are not restricted to, MIF, HMGB-1, TNF-α (tumor necrosis factor alpha), IL-1, IL-4, IL-5, IL-6, IL-8, IL-12, IL-15, IL-17 and IL-18. Proinflammatory effector chemokines include, but are not restricted to, CCL19, CCL21, IL-8, MCP-1 (monocyte chemotactic protein 1), RANTES, MIP-1A (macrophage inflammatory protein 1A), MIP-1B (macrophage inflammatory protein 1B), ENA-78 (epithelial neutrophil activating peptide 78), IP-10, GROB (GRO beta), and Eotaxin. Proinflammatory effector receptors include, but are not restricted to, IL-4R, IL-6R, IL-13R, IL-15R, IL-17R and IL-18R. The stably tethered structure also may react specifically with at least one coagulation factor, such as tissue factor or thrombin. The lymphokines/cytokines react with their receptors on the immune cells to effect activation, and antibodies can block activation by neutralizing the lymphokine/cytokine. Alternatively, antibodies can react with the lymphokine/cytokine receptors to block activation.

The different targets to which the stably tethered structure binds specifically may be from the same or different classes of effectors and coagulation factors. For example, the two or more different targets to which the stably tethered structure binds specifically may be selected from the same class of effectors or coagulation factors, such as two or more different proinflammatory effector cytokines, two ore more different proinflammatory effector chemokines, two or more different proinflammatory effector receptors, or two or more coagulation factors. Alternatively, the two or more different targets may be selected from different classes of effectors and coagulation factors. For example, one target may be a proinflammatory effector of the innate immune system and one target may be a coagulation factor. Or the stably tethered structure may react specifically with two different classes of proinflammatory effectors, such as at least one proinflammatory effector cytokine and at least one proinflammatory effector chemokine, at least one proinflammatory effector cytokine and at least one proinflammatory effector receptor, or at least one proinflammatory effector chemokine and at least one proinflammatory effector receptor. It may also be the case that the two different targets with which the stably tethered structure reacts specifically are more than one epitope of the same proinflammatory effector of the innate immune system or more than one epitope of the same coagulation factor.

Thus, "two different targets" can refer to two different antigens, or to two different epitopes of the same antigen. Multiple antibodies may be used against the same antigen, thus increasing valency. For example, when targeting MIF or HMGB-1, particularly for the treatment of sepsis, some cancers, and atherosclerotic plaques, two antibodies binding to two identical epitopes of the targets can be incorporated into a stably tethered structure with another antibody having one or more binding arms to a different antigen, such as an HLA class II invariant chain antigen, such as CD74. The antibodies may be selected to bind to two different antigens, e.g., antibodies to MIF and CD74; antibodies to HMGB-1 and CD74.

When a proinflammatory effector receptor is targeted, in a preferred embodiment the actual target may be an extracellular domain of the proinflammatory effector receptor. In an alternative embodiment, the stably tethered structure may comprise at least one molecule reactive with a proinflammatory effector receptor. This molecule may be a natural antagonist for said proinflammatory effector receptor, or a fragment or mutant of this antagonist that interacts specifically with the receptor. In a preferred embodiment, the natural antagonist is the natural IL-1 receptor antagonist, or a fragment or mutant of this antagonist.

In one embodiment, a target may be an antigen or receptor of the adaptive immune system. In other embodiments, the target of the stably tethered structure may occur on cells of the innate immune system, such as granulocytes, monocytes, macrophages, dendritic cells, and NK-cells. Other targets include platelets and endothelial cells. Yet another group of targets is the group consisting of C5a, LPS, IFNγ and B7. A further group of suitable targets include CD2, CD3, CD4, CD14, CD18, CD11a, CD20, CD22, CD23, CD25, CD29, CD38, CD40L, CD52, CD64, CD83, CD147, and CD154. The CDs are targets on immune cells, which can be blocked to prevent an immune cell response. CD83 is particularly useful as a marker of activated dendritic cells (Cao et al., *Biochem J.*, Aug. 23, 2004 (Epub ahead of print); Zinser et al., *J. Exp Med.* 200(3):345-51 (2004)).

Certain targets are of particular interest, such as MIF, HMGB-1, TNF-α, the complement factors and complement regulatory proteins, and the coagulation factors. MIF is a pivotal cytokine of the innate immune system and plays an important part in the control of inflammatory responses. Originally described as a T lymphocyte-derived factor that inhibited the random migration of macrophages, the protein known as macrophage migration inhibitory factor (MIF) was an enigmatic cytokine for almost 3 decades. In recent years, the discovery of MIF as a product of the anterior pituitary gland and the cloning and expression of bioactive, recombinant MIF protein have led to the definition of its critical biological role in vivo. MIF has the unique property of being released from macrophages and T lymphocytes that have been stimulated by glucocorticoids. Once released, MIF overcomes the inhibitory effects of glucocorticoids on TNF-α, IL-1 beta, IL-6, and IL-8 production by LPS-stimulated monocytes in vitro and suppresses the protective effects of steroids against lethal endotoxemia in vivo. MIF also antagonizes glucocorticoid inhibition of T-cell proliferation in vitro by restoring IL-2 and IFN-gamma production. MIF is the first mediator to be identified that can counter-regulate the inhibitory effects of glucocorticoids and thus plays a critical role in the host control of inflammation and immunity. MIF is particularly useful in treating cancer, pathological angiogenesis, and sepsis or septic shock.

HMGB-1, a DNA binding nuclear and cytosolic protein, is a proinflammatory cytokine released by monocytes and macrophages that have been activated by IL-1β, TNF, or LPS. Via its B box domain, it induces phenotypic maturation of DCs. It also causes increased secretion of the proinflammatory cytokines IL-1 alpha, IL-6, IL-8, IL-12, TNF-α and RANTES. HMGB-1 released by necrotic cells may be a signal of tissue or cellular injury that, when sensed by DCs, induces and/or enhances an immune reaction. Palumbo et al. report that HMBG1 induces mesoangioblast migration and proliferation (*J Cell Biol*, 164:441-449 (2004)).

HMGB-1 is a late mediator of endotoxin-induced lethality that exhibits significantly delayed kinetics relate to TNF and IL-1beta. Experimental therapeutics that target specific early inflammatory mediators such as TNF and IL-1beta alone have not proven efficacious in the clinic, but stably tethered structures can improve response by targeting both early and late inflammatory inflammatory mediators.

Stably tethered structures that target HMBG-1 are especially useful in treating arthritis, particularly collagen-induced arthritis. Stably tethered structures comprising HMBG-1 also are useful in treating sepsis and/or septic shock. Yang et al., *PNAS USA* 101:296-301 (2004); Kokkola et al., *Arthritis Rheum*, 48:2052-8 (2003); Czura et al., *J Infect Dis*, 187 Suppl 2:S391-6 (2003); Treutiger et al., *J Intern Med*, 254:375-85 (2003).

TNF-α is an important cytokine involved in systemic inflammation and the acute phase response. TNF-α is released by stimulated monocytes, fibroblasts, and endothelial cells. Macrophages, T-cells and B-lymphocytes, granulocytes, smooth muscle cells, eosinophils, chondrocytes, osteoblasts, mast cells, glial cells, and keratinocytes also produce TNF-α after stimulation. Its release is stimulated by several other mediators, such as interleukin-1 and bacterial endotoxin, in the course of damage, e.g., by infection. It has a number of actions on various organ systems, generally together with interleukins-1 and -6. One of the actions of TNF-α is appetite suppression; hence stably tethered structures for treating cachexia preferably target TNF-α. It also stimulates the acute phase response of the liver, leading to an increase in C-reactive protein and a number of other mediators. It also is a useful target when treating sepsis or septic shock.

The complement system is a complex cascade involving proteolytic cleavage of serum glycoproteins often activated by cell receptors. The "complement cascade" is constitutive and non-specific but it must be activated in order to function. Complement activation results in a unidirectional sequence of enzymatic and biochemical reactions. In this cascade, a specific complement protein, C5, forms two highly active, inflammatory byproducts, C5a and C5b, which jointly activate white blood cells. This in turn evokes a number of other inflammatory byproducts, including injurious cytokines, inflammatory enzymes, and cell adhesion molecules. Together, these byproducts can lead to the destruction of tissue seen in many inflammatory diseases. This cascade ultimately results in induction of the inflammatory response, phagocyte chemotaxis and opsonization, and cell lysis.

The complement system can be activated via two distinct pathways, the classical pathway and the alternate pathway. Most of the complement components are numbered (e.g., C1, C2, C3, etc.) but some are referred to as "Factors." Some of the components must be enzymatically cleaved to activate their function; others simply combine to form complexes that are active. Active components of the classical pathway include C1q, C1r, C1s, C2a, C2b, C3a, C3b, C4a, and C4b. Active components of the alternate pathway include C3a, C3b, Factor B, Factor Ba, Factor Bb, Factor D, and Properdin. The last stage of each pathway is the same, and involves component assembly into a membrane attack complex. Active components of the membrane attack complex include C5a, C5b, C6, C7, C8, and C9n.

While any of these components of the complement system can be targeted by a stably tethered structure, certain of the complement components are preferred. C3a, C4a and C5a cause mast cells to release chemotactic factors such as histamine and serotonin, which attract phagocytes, antibodies and complement, etc. These form one group of preferred targets. Another group of preferred targets includes C3b, C4b and C5b, which enhance phagocytosis of foreign cells. Another preferred group of targets are the predecessor components for these two groups, i.e., C3, C4 and C5. C5b, C6, C7, C8 and C9 induce lysis of foreign cells (membrane attack complex) and form yet another preferred group of targets.

Complement C5a, like C3a, is an anaphylatoxin. It mediates inflammation and is a chemotactic attractant for induction of neutrophilic release of antimicrobial proteases and oxygen radicals. Therefore, C5a and its predecessor C5 are particularly preferred targets. By targeting C5, not only is C5a affected, but also C5b, which initiates assembly of the membrane-attack complex. Thus, C5 is another preferred target. C3b, and its predecessor C3, also are preferred targets, as both the classical and alternate complement pathways depend upon C3b. Three proteins affect the levels of this factor, C1 inhibitor, protein H and Factor I, and these are also preferred targets according to the invention. Complement regulatory proteins, such as CD46, CD55, and CD59, may be targets to which the stably tethered structures bind.

Coagulation factors also are preferred targets, particularly tissue factor (TF) and thrombin. TF is also known also as tissue thromboplastin, CD142, coagulation factor III, or factor III. TF is an integral membrane receptor glycoprotein and a member of the cytokine receptor superfamily. The ligand binding extracellular domain of TF consists of two structural modules with features that are consistent with the classification of TF as a member of type-2 cytokine receptors. TF is involved in the blood coagulation protease cascade and initiates both the extrinsic and intrinsic blood coagulation cascades by forming high affinity complexes between the extracellular domain of TF and the circulating blood coagulation factors, serine proteases factor VII or factor VIIa. These enzymatically active complexes then activate factor IX and factor X, leading to thrombin generation and clot formation.

TF is expressed by various cell types, including monocytes, macrophages and vascular endothelial cells, and is induced by IL-1, TNF-α or bacterial lipopolysaccharides. Protein kinase C is involved in cytokine activation of endothelial cell TF expression. Induction of TF by endotoxin and cytokines is an important mechanism for initiation of disseminated intravascular coagulation seen in patients with Gram-negative sepsis. TF also appears to be involved in a variety of non-hemostatic functions including inflammation, cancer, brain function, immune response, and tumor-associated angiogenesis. Thus, stably tethered structures that target TF are useful not only in the treatment of coagulopathies, but also in the treatment of sepsis, cancer, pathologic angiogenesis, and other immune and inflammatory dysregulatory diseases according to the invention. A complex interaction between the coagulation pathway and the cytokine network is suggested by the ability of several cytokines to influence TF expression in a variety of cells and by the effects of ligand binding to the receptor. Ligand binding (factor VIIa) has been reported to give an intracellular calcium signal, thus indicating that TF is a true receptor.

Thrombin is the activated form of coagulation factor II (prothrombin); it converts fibrinogen to fibrin. Thrombin is a potent chemotaxin for macrophages, and can alter their production of cytokines and arachidonic acid metabolites. It is of particular importance in the coagulopathies that accompany sepsis. Numerous studies have documented the activation of the coagulation system either in septic patients or following LPS administration in animal models. Despite more than thirty years of research, the mechanisms of LPS-induced liver toxicity remain poorly understood. It is now clear that they involve a complex and sequential series of interactions between cellular and humoral mediators. In the same period of time, gram-negative systemic sepsis and its sequallae have become a major health concern, attempts to use monoclonal antibodies directed against LPS or various inflammatory mediators have yielded only therapeutic failures. Stably tethered structures that target both thrombin and at least one other target address the clinical failures in sepsis treatment.

In other embodiments, the stably tethered structures bind to a MHC class I, MHC class II or accessory molecule, such as CD40, CD54, CD80 or CD86. The stably tethered structure also may bind to a T-cell activation cytokine, or to a cytokine mediator, such as NF-κB.

In certain embodiments, one of the two different targets may be a cancer cell receptor or cancer-associated antigen, particularly one that is selected from the group consisting of B-cell lineage antigens (CD19, CD20, CD21, CD22, CD23, etc.), VEGFR, EGFR, carcinoembryonic antigen (CEA), placental growth factor (P1GF), tenascin, HER-2/neu, EGP-1, EGP-2, CD25, CD30, CD33, CD38, CD40, CD45, CD52, CD74, CD80, CD138, NCA66, CEACAM6 (carcinoembryonic antigen-related cellular adhesion molecule 6), MUC1, MUC2, MUC3, MUC4, MUC16, IL-6, α-fetoprotein (AFP), A3, CA125, colon-specific antigen-p (CSAp), folate receptor, HLA-DR, human chorionic gonadotropin (HCG), Ia, EL-2, insulin-like growth factor (ILGF) and ILGF receptor, KS-1, Le(y), MAGE, necrosis antigens, PAM-4, prostatic acid phosphatase (PAP), Pr1, prostate specific antigen (PSA), prostate specific membrane antigen (PSMA), S100, T101, TAC, TAG72, TRAIL receptors, and carbonic anhydrase IX.

Targets associated with sepsis and immune dysregulation and other immune disorders include MIF, IL-1, IL-6, IL-8, CD74, CD83, and C5aR. Antibodies and inhibitors against C5aR have been found to improve survival in rodents with sepsis (Huber-Lang et al., *FASEB J* 2002; 16:1567-1574; Riedemann et al., *J Clin Invest* 2002; 110:101-108) and septic shock and adult respiratory distress syndrome in monkeys (Hangen et al., *J Surg Res* 1989; 46:195-199; Stevens et al., *J Clin Invest* 1986; 77:1812-1816). Thus, for sepsis, one of the two different targets preferably is a target that is associated with infection, such as LPS/C5a. Other preferred targets include HMGB-1, TF, CD14, VEGF, and IL-6, each of which is associated with septicemia or septic shock. Preferred stably tethered structures are those that target two or more targets from HMGB-1, TF and MIF, such as MIF/TF, and HMGB-1/TF.

In still other embodiments, one of the two different targets may be a target that is associated with graft versus host disease or transplant rejection, such as MIF (Lo et al., *Bone Marrow Transplant,* 30(6):375-80 (2002)). One of the two different targets also may be one that associated with acute respiratory distress syndrome, such as IL-8 (Bouros et al., *PMC Pulm Med,* 4(1):6 (2004), atherosclerosis or restenosis, such as MIF (Chen et al., *Arterioscler Thromb Vasc Biol,* 24(4):709-14 (2004), asthma, such as IL-18 (Hata et al., *Int Immunol,* Oct. 11, 2004 Epub ahead of print), a granulomatous disease, such as TNF-α (Ulbricht et al., *Arthritis Rheum,* 50(8):2717-8 (2004), a neuropathy, such as carbamylated EPO (erythropoietin) (Leist et al., *Science* 305(5681):164-5 (2004), or cachexia, such as IL-6 and TNF-α.

Other targets include C5a, LPS, IFN-gamma, B7; CD2, CD4, CD14, CD18, CD11a, CD11b, CD11c, CD14, CD18, CD27, CD29, CD38, CD40L, CD52, CD64, CD83, CD147, CD154. Activation of mononuclear cells by certain microbial antigens, including LPS, can be inhibited to some extent by antibodies to CD18, CD11b, or CD11c, which thus implicate β$_2$-integrins (Cuzzola et al., *J Immunol* 2000; 164:5871-5876; Medvedev et al., *J Immunol* 1998; 160: 4535-4542). CD83 has been found to play a role in giant cell arteritis (GCA), which is a systemic vasculitis that affects medium- and large-size arteries, predominately the extracranial branches of the aortic arch and of the aorta itself, resulting in vascular stenosis and subsequent tissue ischemia, and the severe complications of blindness, stroke and aortic arch syndrome (Weyand and Goronzy, *N Engl J Med* 2003; 349: 160-169; Hunder and Valente, In: Inflammatory Diseases of Blood Vessels. G. S. Hoffman and C. M. Weyand, eds, Marcel Dekker, New York, 2002; 255-265). Antibodies to CD83 were found to abrogate vasculitis in a SCID mouse model of human GCA (Ma-Krupa et al., *J Exp Med* 2004; 199:173-183), suggesting to these investigators that dendritic cells, which express CD83 when activated, are critical antigen-processing cells in GCA. In these studies, they used a mouse anti-CD83 Mab (IgG1 clone HB15e from Research Diagnostics). CD154, a member of the TNF family, is expressed on the surface of CD4-positive T-lymphocytes, and it has been reported that a humanized monoclonal antibody to CD154 produced significant clinical benefit in patients with active systemic lupus erythematosus (SLE) (Grammar et al., *J Clin Invest* 2003; 112:1506-1520). It also suggests that this antibody might be useful in other autoimmune diseases (Kelsoe, *J Clin Invest* 2003; 112:1480-1482). Indeed, this antibody was also reported as effective in patients with refractory immune thrombocytopenic purpura (Kuwana et al., *Blood* 2004; 103:1229-1236).

In rheumatoid arthritis, a recombinant interleukin-1 receptor antagonist, IL-1Ra or anakinra (Kineret®), has shown activity (Cohen et al., *Ann Rheum Dis* 2004; 63:1062-8; Cohen, *Rheum Dis Clin North Am* 2004; 30:365-80). An improvement in treatment of these patients, which hitherto required concomitant treatment with methotrexate, is to combine anakinra with one or more of the anti-proinflammatory effector cytokines or anti-proinflammatory effector chemokines (as listed above). Indeed, in a review of antibody therapy for rheumatoid arthritis, Taylor (*Curr Opin Pharmacol* 2003; 3:323-328) suggests that in addition to TNF, other antibodies to such cytokines as IL-1, IL-6, IL-8, IL-15, IL-17 and IL-18, are useful.

Some of the more preferred target combinations include the following. This is a list of examples of preferred combinations, but is not intended to be exhaustive.

| First target | Second target |
| --- | --- |
| MIF | A second proinflammatory effector cytokine, especially HMGB-1, TNF-α, IL-1, or IL-6 |
| MIF | Proinflammatory effector chemokine, especially MCP-1, RANTES, MIP-1A, or MIP-1B |
| MIF | Proinflammatory effector receptor, especially IL-6R IL-13R, and IL-15R |
| MIF | Coagulation factor, especially TF or thrombin |
| MIF | Complement factor, especially C3, C5, C3a, or C5a |
| MIF | Complement regulatory protein, especially CD46, CD55, CD59, and mCRP |
| MIF | Cancer associated antigen or receptor |
| HMGB-1 | A second proinflammatory effector cytokine, especially MIF, TNF-α, IL-1, or IL-6 |
| HMGB-1 | Proinflammatory effector chemokine, especially MCP-1, RANTES, MIP-1A, or MIP-1B |
| HMGB-1 | Proinflammatory effector receptor especially MCP-1, RANTES, MIP-1A, or MIP-1B |
| HMGB-1 | Coagulation factor, especially TF or thrombin |
| HMGB-1 | Complement factor, especially C3, C5, C3a, or C5a |
| HMGB-1 | Complement regulatory protein, especially CD46, CD55, CD59, and mCRP |
| HMGB-1 | Cancer associated antigen or receptor |
| TNF-α | A second proinflammatory effector cytokine, especially MIF, HMGB-1, TNF-α, IL-1, or IL-6 |
| TNF-α | Proinflammatory effector chemokine, especially MCP-1, RANTES, MIP-1A, or MIP-1B |
| TNF-α | Proinflammatory effector receptor, especially IL-6R IL-13R, and IL-15R |
| TNF-α | Coagulation factor, especially TF or thrombin |
| TNF-α | Complement factor, especially C3, C5, C3a, or C5a |
| TNF-α | Complement regulatory protein, especially CD46, CD55, CD59, and mCRP |
| TNF-α | Cancer associated antigen or receptor |
| LPS | Proinflammatory effector cytokine, especially MIF, HMGB-1, TNF-α, IL-1, or IL-6 |
| LPS | Proinflammatory effector chemokine, especially MCP-1, RANTES, MIP-1A, or MIP-1B |
| LPS | Proinflammatory effector receptor, especially IL-6R IL-13R, and IL-15R |
| LPS | Coagulation factor, especially TF or thrombin |
| LPS | Complement factor, especially C3, C5, C3a, or C5a |
| LPS | Complement regulatory protein, especially CD46, CD55, CD59, and mCRP |
| TF or thrombin | Proinflammatory effector cytokine, especially MIF, HMGB-1, TNF-α, IL-1, or IL-6 |
| TF or thrombin | Proinflammatory effector chemokine, especially MCP-1, RANTES, MIP-1A, or MIP-1B |
| TF or thrombin | Proinflammatory effector receptor, especially IL-6R IL-13R, and IL-15R |
| TF or thrombin | Complement factor, especially C3, C5, C3a, or C5a |
| TF or thrombin | Complement regulatory protein, especially CD46, CD55, CD59, and mCRP |
| TF or thrombin | Cancer associated antigen or receptor |

The stably tethered structure may be a mixture that contains at least two separate antibodies and/or receptors or their ligands that bind to the different targets. In one preferred embodiment the targets are selected from the group consisting of proinflammatory effectors of the innate immune system, coagulation factors, complement factors and complement regulatory proteins, and targets specifically associated with an inflammatory or immune-dysregulatory disorder, with a pathologic angiogenesis or cancer, or with an infectious disease.

The stably tethered structure may bind to a receptor or to its target molecule, such as for LPS, IL-1, IL-10, IL-6, MIF, HMGB1, TNF, IFN, tissue factor, thrombin, CD14, CD27, and CD134. Many of these exist as both receptors and as soluble forms in the blood. Binding by the stably tethered structure results in rapid clearance from the blood, and then targeting by the second component of the stably tethered structure to another cell, such as a macrophage, for transport and degradation by the cell, especially the lysosomes. This is particularly effective when the second targeting component is against an internalizing antigen, such as CD74, expressed by macrophages and dendritic cells. This is consistent with the disclosure of Hansen, U.S. Pat. No. 6,458,933, but focusing on inflammatory cytokines and other immune modulation molecules and receptors for immune-dysregulation diseases, and cancer antigens for the immunotherapy of these cancers.

Preferred stably tethered structures for the treatment of cancer include antibodies to CD55 and to any of the above cancer antigens, antibodies to CD46 and to any of the above cancer antigens, antibodies to CD59 and to any of the above cancer antigens, antibodies to MIF and to any of the above cancer antigens, antibodies to NF-κB and any of the above cancer antigens, and antibodies to IL-6 and to any of the above cancer antigens other than IL-6.

The stably tethered structure may be used in conjunction with one or more secondary therapeutics. This secondary therapeutic may be one that affects a component of the innate immune system. Alternatively, it may affect a component of the adaptive immune system. The secondary therapeutic may also be a component that affects coagulation, cancer, or an autoimmune disease, such as a cytotoxic drug.

The stably tethered structure with a diagnostic or therapeutic agent may be provided as a kit for human or mammalian therapeutic and diagnostic use in a pharmaceutically acceptable injection vehicle, preferably phosphate-buffered saline (PBS) at physiological pH and concentration. The preparation preferably will be sterile, especially if it is intended for use in humans. Optional components of such kits include stabilizers, buffers, labeling reagents, radioisotopes, paramagnetic compounds, second antibody for enhanced clearance, and conventional syringes, columns, vials and the like.

Phage Display

In some alternative embodiments, binding peptides for construction of DDD and/or AD domains may be determined by phage display methods that are well known in the art. For example, peptides that bind to DDD domains and that therefore may be substituted for naturally occurring AD sequences may be identified by phage display panning against a DDD dimer and selecting for phage with high binding affinity. Other types of binding peptides that are selective or specific for particular target molecules may be detected by phage display panning against the selected target.

Various methods of phage display and techniques for producing diverse populations of peptides are well known in the art. For example, U.S. Pat. Nos. 5,223,409; 5,622,699 and 6,068,829, each of which is incorporated herein by reference, disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257).

The past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence. This method has also been used to identify novel peptide ligands that may serve as leads to the development of peptidomimetic drugs or imaging agents (Arap et al., 1998a, Science 279:377-380). In addition to peptides, larger protein domains such as single-chain antibodies may also be displayed on the surface of phage particles (Arap et al., 1998a).

Targeting amino acid sequences selective for a given target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to target molecules and samples containing bound phage are collected. Target molecules may, for example, be attached to the bottom of microtiter wells in a 96-well plate. Phage that bind to a target may be eluted and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998a, Smith et al., 1985).

Aptamers

In certain embodiments, a precursor for construct formation may comprise an aptamer. Methods of constructing and determining the binding characteristics of aptamers are well known in the art. For example, such techniques are described in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S, Not all linkages in an oligomer need to be identical.

Methods for preparation and screening of aptamers that bind to particular targets of interest are well known, for example U.S. Pat. No. 5,475,096 and U.S. Pat. No. 5,270,163, each incorporated by reference. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) is retained during separation. Each cycle results in an enrichment of aptamers with high affinity for the target. Repetition for between three to six selection and amplification cycles may be used to generate aptamers that bind with high affinity and specificity to the target.

Avimers

In certain embodiments, the precursors, components and/or complexes described herein may comprise one or more avimer sequences. Avimers are a class of binding proteins somewhat similar to antibodies in their affinities and specifities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, AD and/or DDD sequences for use in the claimed methods and compositions. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Proteins and Peptides

A variety of polypeptides or proteins may be used within the scope of the claimed methods and compositions. In certain embodiments, the proteins may comprise antibodies or fragments of antibodies containing an antigen-binding site. In other embodiments, a protein or peptide may be an effector molecule, such as an enzyme, hormone, cytokine, binding protein or toxin.

As used herein, a protein, polypeptide or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. Accordingly, the term "protein or peptide" encompasses amino acid sequences comprising at least one of the 20 common amino acids found in naturally occurring proteins, or at least one modified or unusual amino acid.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to: 2-Aminoadipic acid, 3-Aminoadipic acid, β-alanine, β-Amino-propionic acid, 2-Aminobutyric acid, 4-Aminobutyric acid, piperidinic acid, 6-Aminocaproic acid, 2-Aminoheptanoic acid, 2-Aminoisobutyric acid, 3-Aminoisobutyric acid, 2-Aminopimelic acid, 2,4-Diaminobutyric acid, Desmosine, 2,2'-Diaminopimelic acid, 2,3-Diaminopropionic acid, N-Ethylasparagine, Hydroxylysine, allo-Hydroxylysine, 3-Hydroxyproline, 4-Hydroxyproline, Isodesmosine, allo-Isoleucine, N-Methylglycine, sarcosine, N-Methylisoleucine, 6-N-Methyllysine, N-Methylvaline, Norvaline Norleucine and Ornithine. Alternatively, proteins or peptides may comprise one or more D-amino acids in addition to or instead of the naturally occurring L-amino acids. Methods of producing peptides incorporating D-amino acids are disclosed, for example, in U.S. Patent Application Publication No. 20050025709, McBride et al., filed Jun. 14, 2004.

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed and may be found at computerized databases known to those of ordinary skill in the art. One such database is the National Center for Biotechnology Information's Genbank and GenPept databases. The coding regions for known genes may be amplified and/or expressed using the techniques disclosed herein or as would be know to those of ordinary skill in the art. Alternatively, various commercial preparations of proteins, polypeptides, and peptides are known to those of skill in the art.

Peptide Mimetics

Another embodiment for the preparation of polypeptides is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993), incorporated herein by reference. The rationale behind the use of peptide mimetics is that the peptide backbone of proteins exists chiefly to orient amino acid side chains so as to facilitate molecular interactions, such as those of antibody and antigen. A peptide mimetic is expected to permit molecular interactions similar to the natural molecule. These principles may be used to engineer second generation molecules having many of the natural properties of the binding peptides disclosed herein, but with altered or improved characteristics, such as increased absorption across the stomach or intestine and/or improved stability or activity in vivo.

Fusion Proteins

Various embodiments may concern fusion proteins. These molecules generally have all or a substantial portion of a peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope. Yet another useful form of fusion may include attachment of a moiety of use for purification, such as the FLAG epitope (Prickett et al., 1989, Biotechniques 7:580-589; Castrucci et al., 1992, J Virol 66:4647-4653). Another use of fusion proteins would concern construction of components of the tethered complexes claimed herein, for example to provide a DDD sequence attached to a first monomer and an AD sequence attached to a second monomer.

Methods of generating fusion proteins are well known to those of skill in the art. Such proteins may be produced, for example, by chemical attachment using bifunctional cross-linking reagents, by de novo synthesis of the complete fusion protein, or by attachment of a DNA sequence encoding a first protein or peptide to a DNA sequence encoding a second peptide or protein, followed by expression of the intact fusion protein, as exemplified in the following Examples.

Synthetic Peptides

Proteins or peptides may be synthesized, in whole or in part, in solution or on a solid support in accordance with conventional techniques. Various automatic synthesizers are commercially available and can be used in accordance with known protocols. See, for example, Stewart and Young, (1984, Solid Phase Peptide Synthesis, 2d. ed., Pierce Chemical Co.); Tam et al., (1983, J. Am. Chem. Soc., 105:6442); Merrifield, (1986, Science, 232: 341-347); and Barany and Merrifield (1979, The Peptides, Gross and Meienhofer, eds., Academic Press, New York, pp. 1-284). Short peptide sequences, usually from about 6 up to about 35 to 50 amino acids, can be readily synthesized by such methods. Alternatively, recombinant DNA technology may be employed wherein a nucleotide sequence which encodes a peptide of interest is inserted into an expression vector, transformed or transfected into an appropriate host cell, and cultivated under conditions suitable for expression.

Peptide Administration

Various embodiments of the claimed methods and/or compositions may concern one or more peptide based stably tethered structures to be administered to a subject. Administration may occur by any route known in the art, including but not limited to oral, nasal, buccal, inhalational, rectal, vaginal, topical, orthotopic, intradermal, subcutaneous, intramuscular, intraperitoneal, intraarterial, intrathecal or intravenous injection.

Unmodified peptides administered orally to a subject can be degraded in the digestive tract and depending on sequence and structure may exhibit poor absorption across the intestinal lining. However, methods for chemically modifying peptides to render them less susceptible to degradation by endogenous proteases or more absorbable through the alimentary tract are well known (see, for example, Blondelle et al., 1995, Biophys. J. 69:604-11; Ecker and Crooke, 1995, Biotechnology 13:351-69; Goodman and Ro, 1995, BURGER'S MEDICINAL CHEMISTRY AND DRUG DISCOVERY, VOL. I, ed. Wollf, John Wiley & Sons; Goodman and Shao, 1996, Pure & Appl. Chem. 68:1303-08). Methods for preparing libraries of peptide analogs, such as peptides containing D-amino acids; peptidomimetics consisting of organic molecules that mimic the structure of a peptide; or peptoids such as vinylogous peptoids, have also been described and may be used to construct peptide based stably tethered structures suitable for oral administration to a subject.

In certain embodiments, the standard peptide bond linkage may be replaced by one or more alternative linking groups, such as $CH_2$—NH, $CH_2$—S, $CH_2$—$CH_2$, CH=CH, CO—$CH_2$, CHOH—$CH_2$ and the like. Methods for preparing peptide mimetics are well known (for example, Hruby, 1982, *Life Sci* 31:189-99; Holladay et al., 1983, *Tetrahedron Lett.* 24:4401-04; Jennings-White et al., 1982, *Tetrahedron Lett.* 23:2533; Almquiest et al., 1980, *J. Med. Chem.* 23:1392-98; Hudson et al., 1979, *Int. J. Pept. Res.* 14:177-185; Spatola et al., 1986, *Life Sci* 38:1243-49; U.S. Pat. Nos. 5,169,862; 5,539,085; 5,576,423, 5,051,448, 5,559,103, each incorporated herein by reference.) Peptide mimetics may exhibit enhanced stability and/or absorption in vivo compared to their peptide analogs.

Alternatively, peptides may be administered by oral delivery using N-terminal and/or C-terminal capping to prevent exopeptidase activity. For example, the C-terminus may be capped using amide peptides and the N-terminus may be capped by acetylation of the peptide. Peptides may also be cyclized to block exopeptidases, for example by formation of cyclic amides, disulfides, ethers, sulfides and the like.

Peptide stabilization may also occur by substitution of D-amino acids for naturally occurring L-amino acids, particularly at locations where endopeptidases are known to act. Endopeptidase binding and cleavage sequences are known in the art and methods for making and using peptides incorporating D-amino acids have been described (e.g., U.S. Patent Application Publication No. 20050025709, McBride et al., filed Jun. 14, 2004, incorporated herein by reference). In certain embodiments, peptides and/or proteins may be orally administered by co-formulation with proteinase- and/or peptidase-inhibitors.

Other methods for oral delivery of therapeutic peptides are disclosed in Mehta ("Oral delivery and recombinant production of peptide hormones," June 2004, *BioPharm International*). The peptides are administered in an enteric-coated solid dosage form with excipients that modulate intestinal proteolytic activity and enhance peptide transport across the intestinal wall. Relative bioavailability of intact peptides using this technique ranged from 1% to 10% of the administered dosage. Insulin has been successfully administered in dogs using enteric-coated microcapsules with sodium cholate and a protease inhibitor (Ziv et al., 1994, *J. Bone Miner. Res.* 18 (Suppl. 2):792-94. Oral administration of peptides has been performed using acylcarnitine as a permeation enhancer and an enteric coating (Eudragit L30D-55, Rohm Pharma Polymers, see Mehta, 2004). Excipients of use for orally administered peptides may generally include one or more inhibitors of intestinal proteases/peptidases along with detergents or other agents to improve solubility or absorption of the peptide, which may be packaged within an enteric-coated capsule or tablet (Mehta, 2004). Organic acids may be included in the capsule to acidify the intestine and inhibit intestinal protease activity once the capsule dissolves in the intestine (Mehta, 2004). Another alternative for oral delivery of peptides would include conjugation to polyethylene glycol (PEG)-based amphiphilic oligomers, increasing absorption and resistance to enzymatic degradation (Soltero and Ekwuribe, 2001, *Pharm. Technol.* 6:110).

In still other embodiments, peptides may be modified for oral or inhalational administration by conjugation to certain proteins, such as the Fc region of IgG1 (see Examples 3-7). Methods for preparation and use of peptide-Fc conjugates are disclosed, for example, in Low et al. (2005, *Hum. Reprod.* 20:1805-13) and Dumont et al. (2005, *J. Aerosol. Med.* 18:294-303), each incorporated herein by reference. Low et al. (2005) disclose the conjugation of the alpha and beta subunits of FSH to the Fc region of IgG1 in single chain or heterodimer form, using recombinant expression in CHO cells. The Fc conjugated peptides were absorbed through epithelial cells in the lung or intestine by the neonatal Fc receptor mediated transport system. The Fc conjugated peptides exhibited improved stability and absorption in vivo compared to the native peptides. It was also observed that the heterodimer conjugate was more active than the single chain form.

Cross-Linkers

In some embodiments, proteins, peptides or other macromolecules may be covalently cross-linked using various cross-linking reagents known in the art, such as homo-bifunctional, hetero-bifunctional and/or photoactivatable cross-linking reagents. Non-limiting examples of such reagents include bisimidates; 1,5-difluoro-2,4-(dinitrobenzene); N-hydroxysuccinimide ester of suberic acid; disuccinimidyl tartarate; dimethyl-3,3'-dithio-bispropionimidate; N-succinimidyl-3-(2-pyridyldithio)propionate; 4-(bromoaminoethyl)-2-nitrophenylazide; and 4-azidoglyoxal. In an exemplary embodiment, a carbodiimide cross-linker, such as DCCD or EDC, may be used to cross-link acidic residues to amino or other groups. Such reagents may be modified to attach various types of labels, such as fluorescent labels.

Bifunctional cross-linking reagents have been extensively used for a variety of purposes. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described (U.S. Pat. No. 5,889,155). The cross-linking reagents combine a nucleophilic hydrazide residue with an electrophilic maleimide residue, allowing coupling in one example, of aldehydes to free thiols. The cross-linking reagent can be modified to cross-link various functional groups.

Antibodies

Various embodiments may concern antibodies for a target. The term "antibody" is used herein to refer to any antibody-like molecule that has an antigen binding region, and includes antibody fragments such as Fab', Fab, F(ab')$_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlowe and Lane, 1988, *Antibodies: A Laboratory Manual*, Cold Spring Harbor Laboratory). Antibodies of use may also be commercially obtained from a wide variety of known sources. For example, a variety of antibody secreting hybridoma lines are available from the American Type Culture Collection (ATCC, Manassas, Va.).

Production of Antibody Fragments

Some embodiments of the claimed methods and/or compositions may concern antibody fragments. Such antibody fragments may be obtained by pepsin or papain digestion of whole antibodies by conventional methods. For example, antibody fragments may be produced by enzymatic cleavage of antibodies with pepsin to provide F(ab')$_2$ fragments. This fragment may be further cleaved using a thiol reducing agent and, optionally, followed by a blocking group for the sulfhydryl groups resulting from cleavage of disulfide linkages, to produce Fab' monovalent fragments. Alternatively, an enzymatic cleavage using papain n produces two monovalent Fab fragments and an Fc fragment. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as *E. coli*. The recombinant host cells synthesize a single polypeptide chain with a linker peptide bridging the two V domains. Methods for producing sFv's are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.).

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immunol., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990).

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the $\mu$, $\gamma$ and $\kappa$ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods, as known in the art. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols. A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Methods of Disease Tissue Detection, Diagnosis and Imaging
Protein-Based In Vitro Diagnosis The present invention contemplates the use of stably tethered structures to screen biological samples in vitro and/or in vivo for the presence of the disease-associated antigens. In exemplary immunoassays, a stably tethered structure comprising an antibody, fusion protein, or fragment thereof may be utilized in liquid phase or bound to a solid-phase carrier, as described below. In preferred embodiments, particularly those involving in vivo administration, the antibody or fragment thereof is humanized. Also preferred, the antibody or fragment thereof is fully human. Still more preferred, the fusion protein comprises a humanized or fully human antibody. The skilled artisan will realize that a wide variety of techniques are known for determining levels of expression of a particular gene and any such known method, such as immunoassay, RT-PCR, mRNA purification and/or cDNA preparation followed by hybridization to a gene expression assay chip may be utilized to determine levels of expression in individual subjects and/or tissues. Exemplary in vitro assays of use include RIA, ELISA, sandwich ELISA, Western blot, slot blot, dot blot, and the like. Although such techniques were developed using intact antibodies, stably tethered structures that incorporate antibodies, antibody fragments or other binding moieties may be used.

Stably tethered structures incorporating antibodies, fusion proteins, antibody fragments and/or other binding moieties may also be used to detect the presence of a target antigen in tissue sections prepared from a histological specimen. Such in situ detection can be used to determine the presence of the antigen and to determine the distribution of the antigen in the examined tissue. In situ detection can be accomplished by applying a detectably-labeled structure to frozen or paraffin-embedded tissue sections. General techniques of in situ detection are well-known to those of ordinary skill. See, for example, Ponder, "Cell Marking Techniques and Their Application," in MAMMALIAN DEVELOPMENT: A PRACTICAL APPROACH 113-38 Monk (ed.) (IRL Press 1987), and Coligan at pages 5.8.1-5.8.8.

Stably tethered structures can be detectably labeled with any appropriate marker moiety, for example, a radioisotope, an enzyme, a fluorescent label, a dye, a chromogen, a chemiluminescent label, a bioluminescent label or a paramagnetic label.

The marker moiety may be a radioisotope that is detected by such means as the use of a gamma counter or a beta-scintillation counter or by autoradiography. In a preferred embodiment, the diagnostic conjugate is a gamma-, beta- or a positron-emitting isotope. A marker moiety refers to a molecule that will generate a signal under predetermined conditions. Examples of marker moieties include radioisotopes, enzymes, fluorescent labels, chemiluminescent labels, bioluminescent labels and paramagnetic labels. The binding of marker moieties to stably tethered structures can be accomplished using standard techniques known to the art. Typical methodology in this regard is described by Kennedy et al., Clin. Chim. Acta 70: 1 (1976), Schurs et al., Clin. Chim. Acta 81: 1 (1977), Shih et al., Intel J. Cancer 46: 1101 (1990).

Nucleic Acid Based In Vitro Diagnosis

Stably tethered structures may, in some embodiments, incorporated nucleic acid moieties. In particular embodiments, nucleic acids may be analyzed to determine levels of binding, particularly using nucleic acid amplification methods. Various forms of amplification are well known in the art and any such known method may be used. Generally, amplification involves the use of one or more primers that hybridize selectively or specifically to a target nucleic acid sequence to be amplified.

The term primer, as defined herein, is meant to encompass any nucleic acid that is capable of priming the synthesis of a nascent nucleic acid in a template-dependent process. Computerized programs for selection and design of amplification primers are available from commercial and/or public sources well known to the skilled artisan. A number of template dependent processes are available to amplify the marker sequences present in a given sample. One of the best-known amplification methods is the polymerase chain reaction (referred to as PCR), which is described in detail in U.S. Pat. Nos. 4,683,195, 4,683,202 and 4,800,159. However, other methods of amplification are known and may be used.

In Vivo Diagnosis

Methods of diagnostic imaging with labeled peptides or MAbs are well-known. For example, in the technique of immunoscintigraphy, ligands or antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993). Also preferred is the use of positron-emitting radionuclides (PET isotopes), such as with an energy of 511 keV, such as $^{18}$F, $^{68}$Ga, $^{64}$Cu, and $^{124}$I. Such imaging can be conducted by direct labeling of the stably tethered structure, or by a pretargeted imaging method, as described in Goldenberg et al, "Antibody Pre-targeting Advances Cancer Radioimmunodetection and Radioimmunotherapy," (J Clin Oncol 2006; 24:823-834), see also U.S. Patent Publication Nos. 20050002945, 20040018557, 20030148409 and 20050014207, each incorporated herein by reference.

The radiation dose delivered to the patient is maintained at as low a level as possible through the choice of isotope for the best combination of minimum half-life, minimum retention in the body, and minimum quantity of isotope which will permit detection and accurate measurement. Examples of radioisotopes that are appropriate for diagnostic imaging include $^{99m}$Tc and $^{111}$In.

The stably tethered structures, or haptens or carriers that bind to them, also can be labeled with paramagnetic ions and a variety of radiological contrast agents for purposes of in vivo diagnosis. Contrast agents that are particularly useful for magnetic resonance imaging comprise gadolinium, manganese, dysprosium, lanthanum, or iron ions. Additional agents include chromium, copper, cobalt, nickel, rhenium, europium, terbium, holmium, or neodymium. ligands, antibodies and fragments thereof can also be conjugated to ultrasound contrast/enhancing agents. For example, one ultrasound contrast agent is a liposome that comprises a humanized IgG or fragment thereof. Also preferred, the ultrasound contrast agent is a liposome that is gas filled.

Imaging Agents and Radioisotopes

Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, carbon$^{14}$, chromium$^{51}$, chlorine$^{36}$, cobalt$^{57}$, cobalt$^{58}$, copper$^{62}$, copper$^{64}$, copper$^{67}$, Eu$^{152}$, fluorine$^{18}$, gallium$^{67}$, gallium$^{68}$, hydrogen$^{3}$, iodine$^{123}$, iodine$^{124}$, iodine$^{125}$, iodine$^{131}$, indium$^{111}$, iron$^{52}$, iron$^{59}$, lutetium$^{177}$, phosphorus$^{32}$, phosphorus$^{33}$, rhenium$^{186}$, rhenium$^{188}$, Sc$^{47}$, selenium$^{75}$, silver$^{111}$, sulphur$^{35}$, technetium$^{94m}$, technetium$^{99m}$, yttrium$^{86}$ and yttrium$^{90}$, and zirconium$^{89}$. I$^{125}$ is often being preferred for use in certain embodiments, and technetium$^{99m}$ and indium$^{111}$ are also often preferred due to their low energy and suitability for long-range detection.

Radioactively labeled proteins or peptides may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups which are often used to bind radioisotopes which exist as metallic ions to peptides include diethylenetriaminepentaacetic acid (DTPA), DOTA, NOTA, porphyrin chelators and ethylene diaminetetracetic acid (EDTA). Also contemplated for use are fluorescent labels, including rhodamine, fluorescein isothiocyanate and renographin.

In certain embodiments, the proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference. These fluorescent labels are preferred for in vitro uses, but may also be of utility in in vivo applications, particularly endoscopic or intravascular detection procedures.

In alternative embodiments, ligands, antibodies, or other proteins or peptides may be tagged with a fluorescent marker. Non-limiting examples of photodetectable labels include Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2', 7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, Edans and Texas Red. These and other luminescent labels may be obtained from commercial sources such as Molecular Probes (Eugene, Oreg.), and EMD Biosciences (San Diego, Calif.).

Chemiluminescent labeling compounds of use may include luminol, isoluminol, an aromatic acridinium ester, an imidazole, an acridinium salt and an oxalate ester, or a bioluminescent compound such as luciferin, luciferase and aequorin. Diagnostic conjugates may be used, for example, in intraoperative, endoscopic, or intravascular tumor or disease diagnosis.

In various embodiments, labels of use may comprise metal nanoparticles. Methods of preparing nanoparticles are known. (See e.g., U.S. Pat. Nos. 6,054,495; 6,127,120; 6,149,868; Lee and Meisel, *J. Phys. Chem.* 86:3391-3395, 1982.) Nanoparticles may also be obtained from commercial sources (e.g., Nanoprobes Inc., Yaphank, N.Y.; Polysciences, Inc., Warrington, Pa.). Modified nanoparticles are available commercially, such as Nanogold® nanoparticles from Nanoprobes, Inc. (Yaphank, N.Y.). Functionalized nanoparticles of use for conjugation to proteins or peptides may be commercially obtained.

EXAMPLES

The following examples are provided to illustrate, but not to limit the claimed invention.

Methods for Generating Non-Covalent a₂b Complexes Composed of Three Fab-Subunits Example 1

General Strategy for Production of Modular Fab Subunits

Fab modules may be produced as fusion proteins containing either a DDD or AD sequence. Independent transgenic cell lines are developed for each Fab fusion protein. Once produced, the modules can be purified if desired or maintained in the cell culture supernatant fluid. Following production, any (Fab-DDD)₂ module can be combined with any Fab-AD module to generate a bispecific trivalent Fab (bsTF).

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1, FIG. 1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1, FIG. 2), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consists of the upstream (5') of the CH1 domain and a SacII restriction endonuclease site, which is 5' of the CH1 coding sequence. The right primer consists of the sequence coding for the first 4 residues of the hinge (PKSC) followed by GGGGS with the final two codons (GS) comprising a Bam HI restriction site.

```
5' of CH1 Left Primer
                                              (SEQ ID NO: 5)
5'GAACCTCGCGGACAGTTAAG-3'

CH1 + G₄S-Bam Right
                                              (SEQ ID NO: 6)
5'GGATCCTCCGCCGCCGCAGCTCTTAGGTTTCTTGTCCACCTTGGTGTT
GCTGG-3'
```

The 410 bp PCR amplimer was cloned into the pGemT PCR cloning vector (Promega, Inc.) and clones were screened for inserts in the T7 (5') orientation.

Construction of (G₄S)₂DDD1

A duplex oligonucleotide, designated (G₄S)₂DDD1, was synthesized by Sigma Genosys (Haverhill, UK) to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

```
                                              (SEQ ID NO: 7)
GSGGGGSGGGGSHIQIPPGLTELLQGYTVEVLRQQPPDLVEFAVEYFTR
LREARA
```

The two oligonucleotides, designated RIIA1-44 top and RIIA1-44 bottom, that overlap by 30 base pairs on their 3' ends, were synthesized (Sigma Genosys) and combined to comprise the central 154 base pairs of the 174 bp DDD1 sequence. The oligonucleotides were annealed and subjected to a primer extension reaction with Taq polymerase.

```
RIIA1-44 top
                                              (SEQ ID NO: 8)
5'GTGGCGGGTCTGGCGGAGGTGGCAGCCACATCCAGATCCCGCCGGGGC

TCACGGAGCTGCTGCAGGGCTACACGGTGGAGGTGCTGCGACAG-3'

RIIA1-44 bottom
```

-continued (SEQ ID NO: 9)
5'GCGCGAGCTTCTCTCAGGCGGGTGAAGTACTCCACTGCGAATTCGACG

AGGTCAGGCGGCTGCTGTCGCAGCACCTCCACCGTGTAGCCCTG-3'

Following primer extension, the duplex was amplified by PCR using the following primers:

```
G4S Bam-Left
                                        (SEQ ID NO: 10)
5'-GGATCCGGAGGTGGCGGGTCTGGCGGAGGT-3'

1-44 stop Eag Right
                                        (SEQ ID NO: 11)
5'-CGGCCGTCAAGCGCGAGCTTCTCTCAGGCG-3'
```

This amplimer was cloned into pGemT and screened for inserts in the T7 (5') orientation.

Construction of (G4S)2-AD1

A duplex oligonucleotide, designated (G4S)2-AD1, was synthesized (Sigma Genosys) to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

GSGGGGSGGGGSQIEYLAKQIVDNAIQQA    (SEQ ID NO: 12)

Two complimentary overlapping oligonucleotides, designated AKAP-IS Top and AKAP-IS Bottom, were synthesized.

```
AKAP-IS Top
                                        (SEQ ID NO: 13)
5'GGATCCGGAGGTGGCGGGTCTGGCGGAGGTGGCAGCCAGATCGA
GTACCTGGCCAAGCAGATCGTGGACAACGCCATCCAGCAGGCCTGA
CGGCCG-3'

AKAP-IS Bottom
                                        (SEQ ID NO: 14)
5'CGGCCGTCAGGCCTGCTGGATGGCGTTGTCCACGATCTGCTTGG
CCAGGTACTCGATCTGGCTGCCACCTCCGCCAGACCCGCCACCTCC
GGATCC-3'
```

The duplex was amplified by PCR using the following primers:

```
G4S Bam-Left
                                        (SEQ ID NO: 15)
5'-GGATCCGGAGGTGGCGGGTCTGGCGGAGGT-3'

AKAP-IS stop Eag Right
                                        (SEQ ID NO: 16)
5'-CGGCCGTCAGGCCTGCTGGATG-3'
```

This amplimer was cloned into the pGemT vector and screened for inserts in the T7 (5') orientation.

Ligating DDD1 with CH1

A 190 bp fragment encoding the DDD1 sequence was excised from pGemT with BamHI and NotI restriction enzymes and then ligated into the same sites in CH1-pGemT to generate the shuttle vector CH1-DDD1-pGemT.

Ligating AD1 with CH1

A 110 bp fragment containing the AD1 sequence was excised from pGemT with BamHI and NotI and then ligated into the same sites in CH1-pGemT to generate the shuttle vector CH1-AD1-pGemT.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

N-Terminal DDD Domains

The location of the DDD or AD is not restricted to the carboxyl terminal end of CH1. A construct was engineered in which the DDD1 sequence was attached to the amino terminal end of the VH domain.

Example 2

Expression Vectors

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

Construction of N-DDD1-Fd-hMN-14-pdHL2

N-DDD1-Fd-hMN-14-pdHL2 is an expression vector for production of a stable dimer that comprises two copies of a fusion protein N-DDD1-Fab-hMN-14, in which DDD1 is linked to hMN-14 Fab at the amino terminus of VH via a flexible peptide spacer.

The expression vector was engineered as follows. The DDD1 domain was amplified by PCR using the two primers shown below.

```
DDD1 Nco Left
                                        (SEQ ID NO: 17)
5'CCATGGGCAGCCACATCCAGATCCCGCC-3'

DDD1-G4S Bam Right
                                        (SEQ ID NO: 18)
5'GGATCCGCCACCTCCAGATCCTCCGCCGCCAGCGCGAGCTTCTCTC
AGGCGGGTG-3'
```

As a result of the PCR, an NcoI restriction site and the coding sequence for part of the linker (G4S)2 containing a BamHI restriction were appended to the 5' and 3' ends, respectively. The 170 bp PCR amplimer was cloned into the pGemT vector and clones were screened for inserts in the T7 (5') orientation. The 194 bp insert was excised from the pGemT vector with NcoI and SalI restriction enzymes and cloned into the SV3 shuttle vector, which was prepared by digestion with those same enzymes, to generate the intermediate vector DDD1-SV3.

The hMN-14 Fd sequence was amplified by PCR using the oligonucleotide primers shown below.

```
hMN-14VH left G4S Bam
                                        (SEQ ID NO: 19)
5'-GGATCCGGCGGAGGTGGCTCTGAGGTCCAACTGGTGGAGAGCGG-3'

CH1-C stop Eag
                                        (SEQ ID NO: 20)
5'-CGGCCGTCAGCAGCTCTTAGGTTTCTTGTC-3'
```

As a result of the PCR, a BamHI restriction site and the coding sequence for part of the linker ($G_4S$) were appended to the 5' end of the amplimer. A stop codon and EagI restriction site was appended to the 3' end. The 1043 bp amplimer was cloned into pGemT. The hMN-14-Fd insert was excised from pGemT with BamHI and EagI restriction enzymes and then ligated with DDD1-SV3 vector, which was prepared by digestion with those same enzymes, to generate the construct N-DDD1-hMN-14Fd-SV3.

The N-DDD1-hMN-14 Fd sequence was excised with XhoI and EagI restriction enzymes and the 1.28 kb insert fragment was ligated with a vector fragment that was prepared by digestion of C-hMN-14-pdHL2 with those same enzymes. The final expression vector is N-DDD1-Fd-hMN-14-pDHL2.

Example 3

Production and Purification of h679-Fab-AD1

The h679-Fd-AD1-pdHL2 vector was linearized by digestion with Sal I restriction endonuclease and transfected into Sp/EEE myeloma cells by electroporation. The di-cistronic expression vector directs the synthesis and secretion of both h679 kappa light chain and h679 Fd-AD1, which combine to form h679 Fab-AD1. Following electroporation, the cells were plated in 96-well tissue culture plates and transfectant clones were selected with 0.05 µM methotrexate (MTX). Clones were screened for protein expression by ELISA using microtitre plates coated with a BSA-IMP-260 (HSG) conjugate and detection with HRP-conjugated goat anti-human Fab. BIAcore analysis using an HSG (IMP-239) sensorchip was used to determine the productivity by measuring the initial slope obtained from injection of diluted media samples. The highest producing clone had an initial productivity of approximately 30 mg/L. A total of 230 mg of h679-Fab-AD1 was purified from 4.5 liters of roller bottle culture by single-step IMP-291 affinity chromatography. Culture media was concentrated approximately 10-fold by ultrafiltration before loading onto an IMP-291-affigel column. The column was washed to baseline with PBS and h679-Fab-AD1 was eluted with 1 M imidazole, 1 mM EDTA, 0.1 M NaAc, pH 4.5. SE-HPLC analysis of the eluate showed a single sharp peak with a retention time (9.63 min) consistent with a 50 kDa protein (not shown). Only two bands, which represent the polypeptide constituents of h679-AD1, were evident by reducing SDS-PAGE analysis (not shown).

Example 4

Production and Purification of N-DDD1-Fab-hMN-14 and C-DDD1-Fab-hMN-14

The C-DDD1-Fd-hMN-14-pdHL2 and N-DDD1-Fd-hMN-14-pdHL2 vectors were transfected into Sp2/0-derived myeloma cells by electroporation. C-DDD1-Fd-hMN-14-pdHL2 is a di-cistronic expression vector, which directs the synthesis and secretion of both hMN-14 kappa light chain and hMN-14 Fd-DDD1, which combine to form C-DDD1-hMN-14 Fab. N-DDD1-hMN-14-pdHL2 is a di-cistronic expression vector, which directs the synthesis and secretion of both hMN-14 kappa light chain and N-DDD1-Fd-hMN-14, which combine to form N-DDD1-Fab-hMN-14. Each fusion protein forms a stable homodimer via the interaction of the DDD1 domain.

Following electroporation, the cells were plated in 96-well tissue culture plates and transfectant clones were selected with 0.05 µM methotrexate (MTX). Clones were screened for protein expression by ELISA using microtitre plates coated with WI2 (a rat anti-id monoclonal antibody to hMN-14) and detection with HRP-conjugated goat anti-human Fab. The initial productivity of the highest producing C-DDD1-Fab-hMN14 Fab and N-DDD1-Fab-hMN14 Fab clones was 60 mg/L and 6 mg/L, respectively.

Affinity Purification of N-DDD1-hMN-14 and C-DDD1-hMN-14 with AD1-Affigel

The DDD/AD interaction was utilized to affinity purify DDD1-containing constructs. AD1-C is a peptide that was made synthetically consisting of the AD1 sequence and a carboxyl terminal cysteine residue (see Example 6), which was used to couple the peptide to Affigel following reaction of the sulfhydryl group with chloroacetic anhydride. DDD-containing $a_2$ structures specifically bind to the AD1-C-Affigel resin at neutral pH and can be eluted at low pH (e.g., pH 2.5).

A total of 81 mg of C-DDD1-Fab-hMN-14 was purified from 1.2 liters of roller bottle culture by single-step AD1-C affinity chromatography. Culture media was concentrated approximately 10-fold by ultrafiltration before loading onto an AD1-C-affigel column. The column was washed to baseline with PBS and C-DDD1-Fab-hMN-14 was eluted with 0.1 M Glycine, pH 2.5. SE-HPLC analysis of the eluate showed a single protein peak with a retention time (8.7 min) consistent with a 107 kDa protein (not shown). The purity was also confirmed by reducing SDS-PAGE, showing only two bands of molecular size expected for the two polypeptide constituents of C-DDD1-Fab-hMN-14 (not shown).

A total of 10 mg of N-DDD1-hMN-14 was purified from 1.2 liters of roller bottle culture by single-step AD1-C affinity chromatography as described above. SE-HPLC analysis of the eluate showed a single protein peak with a retention time (8.77 min) similar to C-DDD1-Fab-hMN-14 and consistent with a 107 kDa protein (not shown). Reducing SDS-PAGE showed only two bands attributed to the polypeptide constituents of N-DDD1-Fab-hMN-14 (not shown).

The binding activity of C-DDD1-Fab-hMN-14 was determined by SE-HPLC analysis of samples in which the test article was mixed with various amounts of WI2. A sample prepared by mixing WI2 Fab and C-DDD1-Fab-hMN-14 at a molar ratio of 0.75:1 showed three peaks, which were attributed to unbound C-DDD1-Fab-hMN14 (8.71 min), C-DDD1-Fab-hMN-14 bound to one WI2 Fab (7.95 min), and C-DDD1-Fab-hMN14 bound to two WI2 Fabs (7.37 min) (not shown). When a sample containing WI2 Fab and C-DDD1-Fab-hMN-14 at a molar ratio of 4 was analyzed, only a single peak at 7.36 minutes was observed (not shown). These results demonstrate that hMN14-Fab-DDD1 is dimeric and has two active binding sites. Very similar results were obtained when this experiment was repeated with N-DDD1-Fab-hMN-14.

A competitive ELISA demonstrated that both C-DDD1-Fab-hMN-14 and N-DDD1-Fab-hMN-14 bind to CEA with an avidity similar to hMN-14 IgG, and significantly stronger than monovalent hMN-14 Fab (not shown). ELISA plates were coated with a fusion protein containing the epitope (A3B3) of CEA for which hMN-14 is specific.

Example 5

Formation of $a_2b$ Complexes

Evidence for the formation of an $a_2b$ complex was first provided by SE-HPLC analysis of a mixture containing C-DDD1-Fab-hMN-14 (as $a_2$) and h679-Fab-AD1 (as b) in an equal molar amount. When such a sample was analyzed, a single peak was observed having a retention time of 8.40 minutes, which is consistent with the formation of a new protein that is larger than either h679-Fab-AD1 (9.55 min) or C-DDD1-Fab-hMN-14 (8.73 min) alone (not shown). The upfield shift was not observed when hMN-14 F(ab')$_2$ was mixed with h679-Fab-AD1 or C-DDD1-Fab-hMN-14 was mixed with 679-Fab-NEM, demonstrating that the interaction is mediated specifically via the DDD1 and AD1 domains. Very similar results were obtained using h679-Fab-AD1 and N-DDD1-Fab-hMN-14 (not shown).

BIAcore was used to further demonstrate and characterize the specific interaction between the DD1 and AD1 fusion proteins. The experiments were performed by first allowing either h679-Fab-AD1 or 679-Fab-NEM to bind to the surface of a high density HSG-coupled (IMP239) sensorchip, followed by a subsequent injection of C-DDD1-Fab-hMN-14 or hMN-14 F(ab')$_2$. As expected, only the combination of h679-Fab-AD1 and C-DDD1-Fab-hMN-14 resulted in a further increase in response units when the latter was injected (not shown). Similar results were obtained using N-DDD1-Fab-hMN-14 and h679-Fab-AD1 (not shown).

Equilibrium SE-HPLC experiments were carried out to determine the binding affinity of the specific interaction between AD1 and DDD1 present in the respective fusion proteins. The dissociation constants ($K_d$) for the binding of h679-Fab-AD1 with C-DDD1-Fab-hMN-14, N-DDD1-hMN-14 and a commercial sample of recombinant human RIIα were found to be 15 nM, 8 nM and 30 nM, respectively.

Other Related Methods

Example 6

Generation of Di-AD1

In this example, a small polypeptide (AD1-C) having the amino acid sequence shown below was made synthetically.

NH$_2$-KQIEYLAKQIVDNAIQQAKGC-COOH (SEQ ID NO: 37)

In AD1-C, the AD1 amino acid sequence (underlined) is flanked by a lysine residue at N-terminus and a KGC tripeptide at carboxyl terminus. Two lysine (K) residues were introduced to increase solubility and a glycine (G) residue was inserted before the C-terminal cysteine to provide added flexibility. Upon treatment with DMSO, AD1-C was oxidized to a dimer, designated Di-AD1, which was purified by RP-HPLC. A schematic structure of Di-AD1 is shown below (=indicating the disulfide bridge)

NH$_2$-KQIEYLAKQIVDNAIQQAKGC = CGKAQQIANDVIQKALYEIQ (SEQ ID NO: 21)

K-NH$_2$

There are a number of functional groups present in Di-AD1 or AD1-C that may be utilized for further modifications. For examples, the 8 and 4 primary amino groups contained in Di-AD1 and AD1-C, respectively, may be used to couple drugs, toxins, proteins, or other effectors. Further, Di-AD1 and AD1-C have 2 and 1 tyrosine residues, respectively, which may be used for radio-iodination. Finally, AD1-C contains a free cysteine residue, which can also be used to couple effectors or form a Di-AD1 analog containing effectors.

Example 7

A Novel Pretargeting Approach

The method of the present invention lends itself to new pretargeting methodologies.

The following provides an example of a pretargeting system that uses the affinity enhancement system (Le Doussal et al., J Nucl Med (1989), 30:1358-66) without the need for a hapten-binding antibody. A dimer of C-DDD1-Fab-hMN-14 or N-Fab-DDD2-hMN-14, produced as described in Example 4, may be used for pretargeting a tumor. The 107 kDa protein is first administered intravenously to patients and allowed to bind CEA on tumors while clearing from blood and normal tissues. At a later time, a divalent peptide, such as a DOTA conjugate of Di-AD1 carrying a therapeutic (for example, $^{90}$Y) or diagnostic radioisotope (for example, $^{111}$In), is administered intravenously. The small peptide (=5000 Da), while rapidly clearing from blood and normal tissues, localizes to the tumor as it contains two AD sequences that is expected to interact specifically with C-DDD1-Fab-hMN-14 already retained by the tumor.

Cross-linking of C-DDD1-Fab-hMN-14 with Di-AD1 in vitro was demonstrated by SE-HPLC. When C-DDD1-Fab-hMN-14 was mixed with Di-AD1 the protein peak shifted from 8.67 min to 7.95 min, indicating the formation of a crosslinked structure (not shown). No such shift was observed when hMN-14 F(ab')$_2$ was mixed with Di-AD1, demonstrating that the cross-linking is mediated by the interaction between DDD1 and AD1. To confirm that the peak shift was in fact due to specific cross-linking of C-DDD1-Fab-hMN-14, the complex was reduced with DTT to cleave the disulfide linkage of Di-AD1, which resulted in the shift of the peak back to 8.67 min (not shown).

Example 8

Affinity Purification of Either DDD or AD Fusion Proteins

Universal affinity purification systems can be developed by production of DDD or AD proteins, which have lower affinity docking. The DDD formed by RIα dimers binds AKAP-IS (AD1) with a 500-fold weaker affinity (225 nM) compared to RIIα. Thus, RIα dimers formed from the first 44 amino acid resides can be produced and coupled to a resin to make an attractive affinity matrix for purification of any AD1-containing fusion protein.

Many lower affinity (0.1 μM) AKAP anchoring domains exist in nature. If necessary, highly predicable amino acid substitutions can be introduced to further lower the binding affinity. A low affinity AD can be produced either synthetically or biologically and coupled to resin for use in affinity purification of any DDD1 fusion protein.

Methods Related to the Generation of Stably Tethered Structures

Example 9

Vectors for Producing Disulfide Stabilized Structures Composed of Three Fab Fragments N-DDD2-Fd-hMN-14-pdHL2

Figure 4:
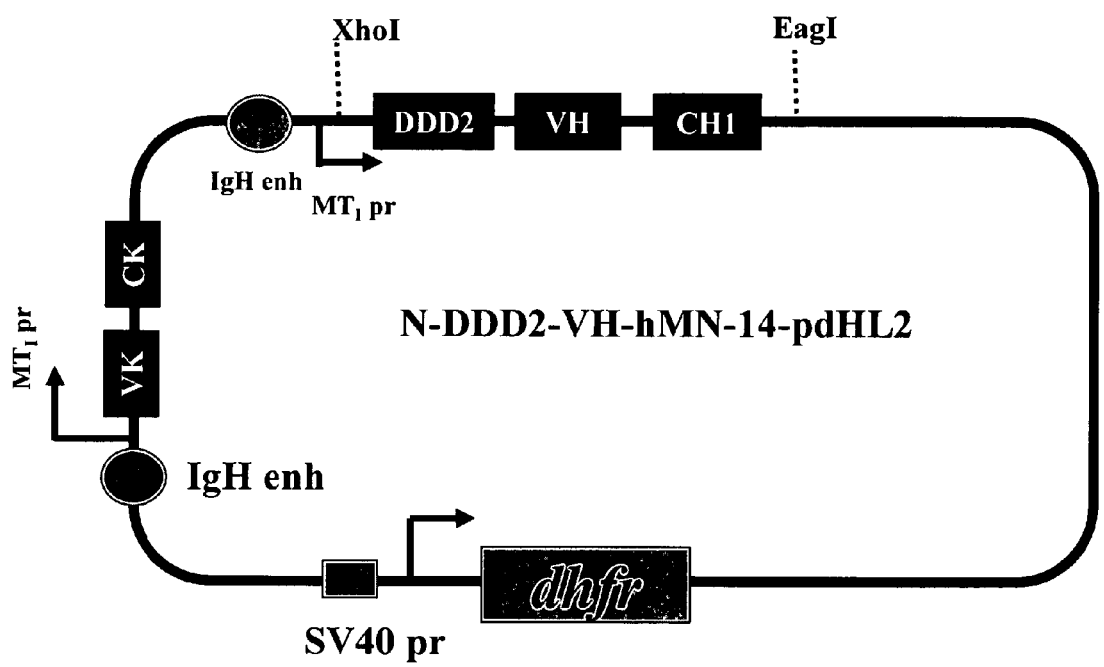
FIG. 4 shows the design of the N-DDD2-VH-hMN-14-pdHL2 plasmid expression vector.

N-DDD2-hMN-14-pdHL2 is an expression vector for production of N-DDD2-Fab-hMN-14, which possesses a dimerization and docking domain sequence of DDD2 appended to the amino terminus of the Fd (FIG. 4). The DDD2 is coupled to the $V_H$ domain via a 15 amino acid residue Gly/Ser peptide linker. DDD2 has a cysteine residue preceding the dimerization and docking sequences, which are identical to those of DDD1. The fusion protein secreted is composed of two identical copies of hMN-14 Fab held together by non-covalent interaction of the DDD2 domains (FIG. 3B).

The expression vector was engineered as follows. Two overlapping, complimentary oligonucleotides (DDD2 Top and DDD2 Bottom), which comprise residues 1-13 of DDD2, were made synthetically. The oligonucleotides were annealed and phosphorylated with T4 polynucleotide kinase (PNK), resulting in overhangs on the 5' and 3' ends that are compatible for ligation with DNA digested with the restriction endonucleases NcoI and PstI, respectively.

```
DDD2 Top
                                            (SEQ ID NO: 22)
5'CATGTGCGGCCACATCCAGATCCCGCCGGGGCTCACGGAGCTGC
TGCA-3'

DDD2 Bottom
                                            (SEQ ID NO: 23)
5'GCAGCTCCGTGAGCCCCGGCGGGATCTGGATGTGGCCGCA-3'
```

The duplex DNA was ligated with a vector fragment, DDD1-hMN14 Fd-SV3 that was prepared by digestion with NcoI and PstI, to generate the intermediate construct DDD2-hMN14 Fd-SV3. A 1.28 kb insert fragment, which contained the coding sequence for DDD2-hMN14 Fd, was excised from the intermediate construct with XhoI and EagI restriction endonucleases and ligated with hMN14-pdHL2 vector DNA that was prepared by digestion with those same enzymes. The final expression vector is N-DDD2-Fd-hMN-14-pdHL2 (FIG. 4).

C-DDD2-Fd-hMN-14-pdHL2

Figure 5:
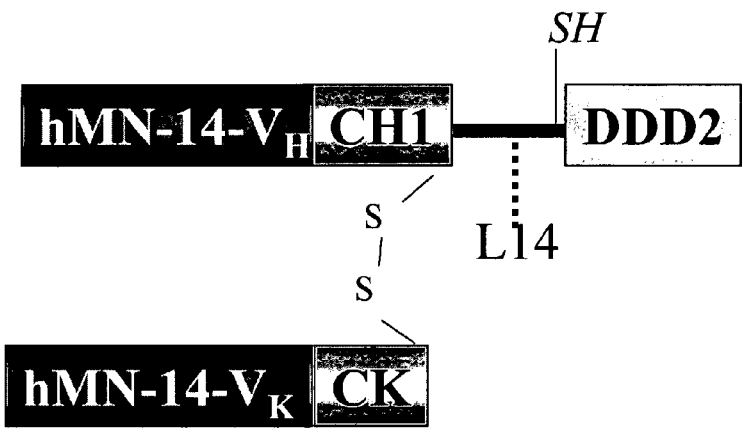
FIG. 5 shows a schematic diagram of C-DDD2-Fab-hMN-14 (A), and the putative $a_2$ structure formed by DDD2-mediated dimerization (B).
Figure 5:
Figure 5:
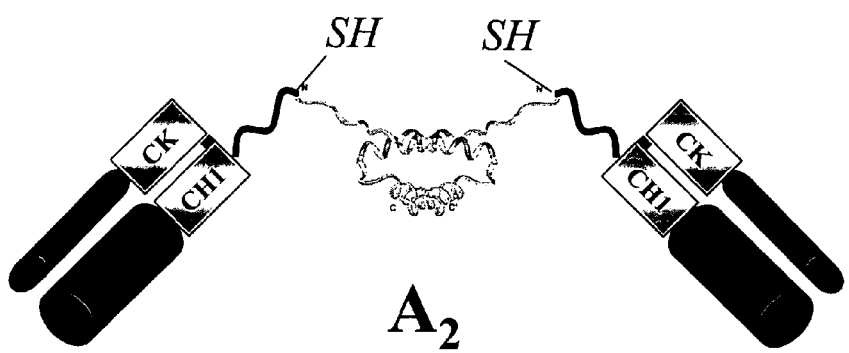

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd via a 14 amino acid residue Gly/Ser peptide linker (FIG. 5A). The fusion protein secreted is composed of two identical copies of hMN-14 Fab held together by non-covalent interaction of the DDD2 domains (FIG. 5B).

The expression vector was engineered as follows. Two overlapping, complimentary oligonucleotides, which comprise the coding sequence for part of the linker peptide (GGGGSGGGCG, SEQ ID NO:38) and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

```
G4S-DDD2 top
                                            (SEQ ID NO: 24)
5'GATCCGGAGGTGGCGGGTCTGGCGGAGGTTGCGGCCACATCCAGA
TCCCGCCGGGGCTCACGGAGCTGCTGCA-3'

G4S-DDD2 bottom
                                            (SEQ ID NO: 25)
5'GCAGCTCCGTGAGCCCCGGCGGGATCTGGATGTGGCCGCAACCTC
CGCCAGACCCGCCACCTCCG-3'
```

Figure 6:
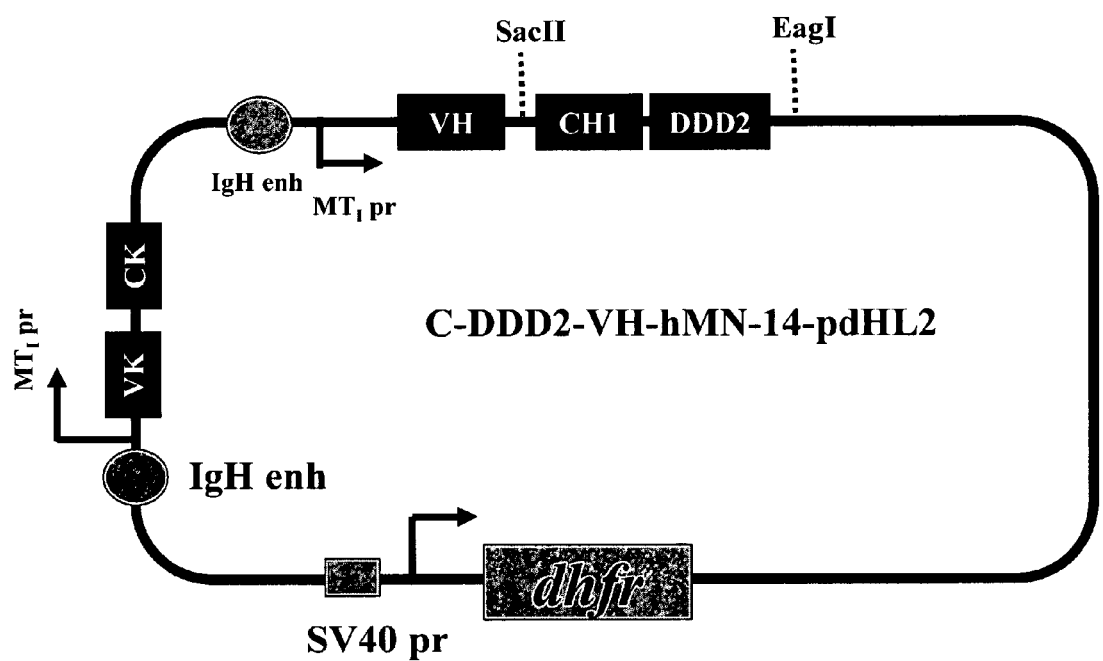
FIG. 6 shows the design of the C-DDD2-VH-hMN-14-pdHL2 plasmid expression vector.

The duplex DNA was ligated with the shuttle vector CH1-DDD1-pGemT, which was prepared by digestion with BamHI and PstI, to generate the shuttle vector CH1-DDD2-pGemT. A 507 bp fragment was excised from CH1-DDD2-pGemT with SacII and EagI and ligated with the IgG expression vector hMN14(I)-pdHL2, which was prepared by digestion with SacII and EagI. The final expression construct is C-DDD2-Fd-hMN-14-pdHL2 (FIG. 6)

h679-Fd-AD2-pdHL2 h679-Fab-AD2, was designed to pair as B to N-DDD2-Fab-hMN-14 or C-DDD2-Fab-hMN-14. h679-Fd-AD2-pdHL2 is an expression vector for the production of h679-Fab-AD2, which possesses an anchor domain sequence of AD2 appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

```
AD2 Top
                                            (SEQ ID NO: 26)
5'GATCCGGAGGTGGCGGGTCTGGCGGATGTGGCCAGATCGAGTACC
TGGCCAAGCAGATCGTGGACAACGCCATCCAGCAGGCCGGCTGCTGA
A-3'

AD2 Bottom
                                            (SEQ ID NO: 27)
5'TTCAGCAGCCGGCCTGCTGGATGGCGTTGTCCACGATCTGCTTGG
CCAGGTACTCGATCTGGCCACATCCGCCAGACCCGCCACCTCCG-3'
```

The duplex DNA was ligated into the shuttle vector CH1-AD1-pGemT, which was prepared by digestion with BamHI and SpeI, to generate the shuttle vector CH1-AD2-pGemT. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Example 10

Production of h679-Fab-AD2

The h679-Fd-AD2-pdHL2 vector was transfected into Sp/EEE myeloma cells by electroporation. The di-cistronic expression vector directs the synthesis and secretion of both h679 kappa light chain and h679 Fd-AD2, which combine to form h679-Fab-AD2. The cysteine residues on either end of the AD provide two potentially reactive sulfhydryl groups. Following electroporation, the cells were plated in 96-well tissue culture plates and transfectant clones were selected with 0.05 µM methotrexate (MTX). Clones were screened for protein expression by ELISA using microtitre plates coated with a BSA-IMP-260 (HSG) conjugate and detection with goat anti-human Fab-HRP. BIAcore analysis using an HSG (IMP-239) sensorchip was used to determine the productivity by measuring the initial slope obtained from injection of diluted media samples. The highest producing clone had an initial productivity of approximately 50 mg/L. A total of 160 mg of h679-Fab-AD2 was purified from 2.9 liters of roller bottle culture by single-step IMP-291 affinity chromatography. Culture media was concentrated approximately 10-fold by ultrafiltration before loading onto an IMP-291-affigel column. The column was washed to baseline with PBS and h679-AD2 was eluted with 1 M imidazole, 1 mM EDTA, 0.1 M NaAc, pH 4.5. SE-HPLC analysis shows a single sharp peak with a retention time (~10 min) consistent with a 50 kDa protein (not shown). When this material was mixed with hMN14-Fab-DDD1, only ⅓ was reactive as evident by the observation in the SE-HPLC trace of a new peak attributed to the binary complex (not shown). However, reduction of the h679-Fab-AD2 with TCEP resulted in 100% activity (not shown). This suggests that (1) an intramolecular disulfide bond may form between the two cysteine residues of AD2, preventing association with the DDD but also protecting the sulfhydryl groups from reacting with other substances; and (2) the intramolecular disulfide bridge can be broken by reduction resulting in a DDD-reactive anchor domain with two free sulfhydryl groups.

Example 11

Production of N-DDD2-Fab-hMN-14 as an $a_2$ Structure

The N-DDD2-Fd-hMN-14-pdHL2 vector was transfected into Sp/EEE myeloma cells by electroporation. The di-cistronic expression vector directs the synthesis and secretion of both hMN-14 kappa light chain and N-DDD2-hMN-14 Fd, which combine to form N-DDD2-hMN14 Fab. An $A_2$ structure is expected to form by dimerization via DDD2, resulting in two potentially reactive sulfhydryl groups provided by the cysteine residue in each DDD2. Following electroporation, the cells were plated in 96-well tissue culture plates and transfectant clones were selected with 0.05 μM methotrexate (MTX).

Clones were screened for protein expression by ELISA using microtitre plates coated with WI2 (hMN-14 anti-Id) and detection with goat anti-human Fab-HRP. The highest producing clones had an initial productivity of approximately 10 mg/L. A total of 16 mg of N-DDD2-hMN-14 was purified by protein L affinity chromatography from 1.8 liters of roller bottle culture. Culture media was concentrated approximately 10-fold by ultrafiltration before loading onto a protein L affinity chromatography column. The column was washed to baseline with PBS and N-DDD2-hMN14 was eluted with 1 mM EDTA, 0.1 M NaAc, pH 2.5 and immediately neutralized with Tris-HCl. SE-HPLC analysis showed four protein peaks (not shown), two of which were subsequently identified as $a_4$ (7.9 min) and $a_2$ (8.8 min) forms of N-DDD2-Fab-hMN-14 and the remaining two were the dimer and monomer of the kappa chain. This mixture showed little binding activity with h679-Fab-AD1, unless a thiol-reducing agent such as TCEP was added to convert most of the $a_4$ form to the $a_2$ form (not shown). These data suggest that (1) $a_4$ is formed via linking two $a_2$ structures through the cysteines present in the DDD2, thereby preventing association with the AD but also protecting the sulfhydryl groups from reacting with other substances; and (2) the intermolecular disulfide bridges can be broken by reduction, resulting in an $a_2$ structures with AD-reactive DDD dimers containing two free sulfhydril groups. Note that this side-product ($a_4$) is composed of four active Fab subunits. Approximately 15% of the total N-DDD2-Fab-hMN-14 remains in the $A_4$ form following reduction, even with high TCEP concentrations and long reaction times (not shown). This suggests that other mechanisms such as domain swapping may contribute to the formation of the $a_4$ form, in addition to disulfide bridging.

Example 12

Production of C-DDD2-Fab-hMN-14

The C-DDD2-Fd-hMN-14-pdHL2 vector was transfected into Sp/EEE myeloma cells by electroporation. The di-cistronic expression vector directs the synthesis and secretion of both hMN-14 kappa light chain and C-DDD2-Fd-hMN-14, which combine to form C-DDD2-Fab-hMN14. Like N-DDD2-Fab-hMN-14, an $a_2$ structure is expected to form by dimerization via DDD2, resulting in two potentially reactive sulfhydryl groups provided by the cysteine residue in each DDD2. Following electroporation, the cells were plated in 96-well tissue culture plates and transfectant clones were selected with 0.05 μM methotrexate (MTX).

Clones were screened for protein expression by ELISA using microtitre plates coated with WI2 (hMN-14 anti-Id) and detection with goat anti-human Fab-HRP. The highest producing clones had an initial productivity of approximately 100 mg/L, which was 10-fold higher than that of N-DDD2-Fab-hMN-14. A total of 200 mg of C-DDD2-hMN-14 was purified by protein L affinity chromatography from 1.8 liters of roller bottle culture as described in Example 3. The SE-HPLC profile of the Protein L-purified C-DDD2-Fab-hMN-14 (not shown) was similar to that of N-DDD2-Fab-hMN-14. Two of the four protein peaks were identified as the $a_4$ (8.40 min) and $a_2$ (9.26 min) forms of C-DDD2-Fab-hMN-14 and the remaining two represent dimer and monomer of the kappa chain. This mixture showed little binding activity with h679-AD1, unless a thiol-reducing agent such as TCEP was added to convert most of the $a_4$ form of to the $a_2$ form, which then bound avidly to h679-AD1. These data suggest that C-DDD2-Fab-hMN-14 is a functional equivalent of N-DDD2-hMN-14.

Example 13

Generation of TF1 h679-Fab-AD2 was designed as a B component to pair with an $a_2$ component such as N-DDD2-hMN-Fab-14 or C-DDD2-hMN-14, which when combined, would readily associate to form an $a_2b$ structure (FIG. 7A) that might be further induced to bind covalently via disulfide bonds (FIG. 7B). Since characterization of N-DDD2- and AD2-constructs demonstrated that reduction of each was necessary to achieve full DDD/AD interaction, a reduction step was included in the process. Initially, immobilized TCEP was used as a reducing agent to save the time required for removal of the reducing agent. Following reduction for 1 hour at room temperature, the TCEP-Agarose was removed by centrifugation and DMSO was added to the reaction solution to a final concentration of 10%. The first evidence of the existence of a covalently linked $a_2b$ complex, henceforth referred to as TF1, was demonstrated by BIAcore analysis.

After feasibility was established in small-scale reactions using immobilized TCEP, a large scale preparation of TF1 was carried out as follows. N-DDD2-Fab-hMN-14 (Protein L-purified) and h679-Fab-AD2 (IMP-291-purified) were first mixed in roughly stoichiometric concentrations in 1 mM EDTA, PBS, pH 7.4. Before the addition of TCEP, SE-HPLC did not show any evidence of $a_2b$ formation (not shown). Instead there were peaks representing $a_4$ (7.97 min; 200 kDa), $a_2$ (8.91 min; 100 kDa) and B (10.01 min; 50 kDa). Addition of 5 mM TCEP rapidly resulted in the formation of the $a_2b$ complex as demonstrated by a new peak at 8.43 min, consistent with a 150 kDa protein (not shown). Apparently there was excess B in this experiment as a peak attributed to h679-Fab-AD2 (9.72 min) was still evident yet no apparent peak corresponding to either $a_2$ or $a_4$ was observed (not shown). After reduction for one hour, the TCEP was removed by overnight dialysis against several changes of PBS. The resulting solution was brought to 10% DMSO and held overnight at room temperature.

When analyzed by SE-HPLC, the peak representing $a_2b$ appeared to be sharper with a slight reduction of the retention time by 0.1 min to 8.31 min (not shown), which, based on our previous findings, indicates an increase in binding affinity. The complex was further purified by IMP-291 affinity chromatography to remove the kappa chain contaminants. As expected, the excess h679-AD2 was co-purified and later removed by preparative SE-HPLC (not shown).

TF1 is a highly stable complex. When TF1 was tested for binding to an HSG (IMP-239) sensorchip, there was no apparent decrease of the observed response at the end of sample injection. In contrast, when a solution containing an equimolar mixture of both C-DDD1-Fab-hMN-14 and h679-Fab-AD1 was tested under similar conditions, the observed increase in response units was accompanied by a detectable drop during and immediately after sample injection, indicating that the initially formed $a_2b$ structure was unstable. Moreover, whereas subsequent injection of WI2 gave a substantial increase in response units for TF1, no increase was evident for the C-DDD1/AD1 mixture.

The additional increase of response units resulting from the binding of WI2 to TF1 immobilized on the sensorchip corresponds to two fully functional binding sites, each contributed by one subunit of N-DDD2-Fab-hMN-14. This was confirmed by the ability of TF1 to bind two Fab fragments of WI2 (not shown). When a mixture containing h679-AD2 and N-DDD1-hMN14, which had been reduced and oxidized exactly as TF1, was analyzed by BIAcore, there was little additional binding of WI2 (not shown), indicating that a disulfide-stabilized $a_2b$ complex such as TF1 could only form through the interaction of DDD2 and AD2.

Two improvements to the process were implemented to reduce the time and efficiency of the process. First, a slight molar excess of N-DDD2-Fab-hMN-14 present as a mixture of $a_4/a_2$ structures was used to react with h679-Fab-AD2 so that no free h679-Fab-AD2 remained and any $a_4/a_2$ structures not tethered to h679-Fab-AD2, as well as light chains, would be removed by IMP-291 affinity chromatography. Second, hydrophobic interaction chromatography (HIC) has replaced dialysis or diafiltration as a means to remove TCEP following reduction, which would not only shorten the process time but also add a potential viral removing step. N-DDD2-Fab-hMN-14 and 679-Fab-AD2 were mixed and reduced with 5 mM TCEP for 1 hour at room temperature. The solution was brought to 0.75 M ammonium sulfate and then loaded onto a Butyl FF HIC column. The column was washed with 0.75 M ammonium sulfate, 5 mM EDTA, PBS to remove TCEP. The reduced proteins were eluted from the HIC column with PBS and brought to 10% DMSO. Following incubation at room temperature overnight, highly purified TF1 was isolated by IMP-291 affinity chromatography (not shown). No additional purification steps, such as gel filtration, were required.

Example 14

Generation of TF2

Figure 8:
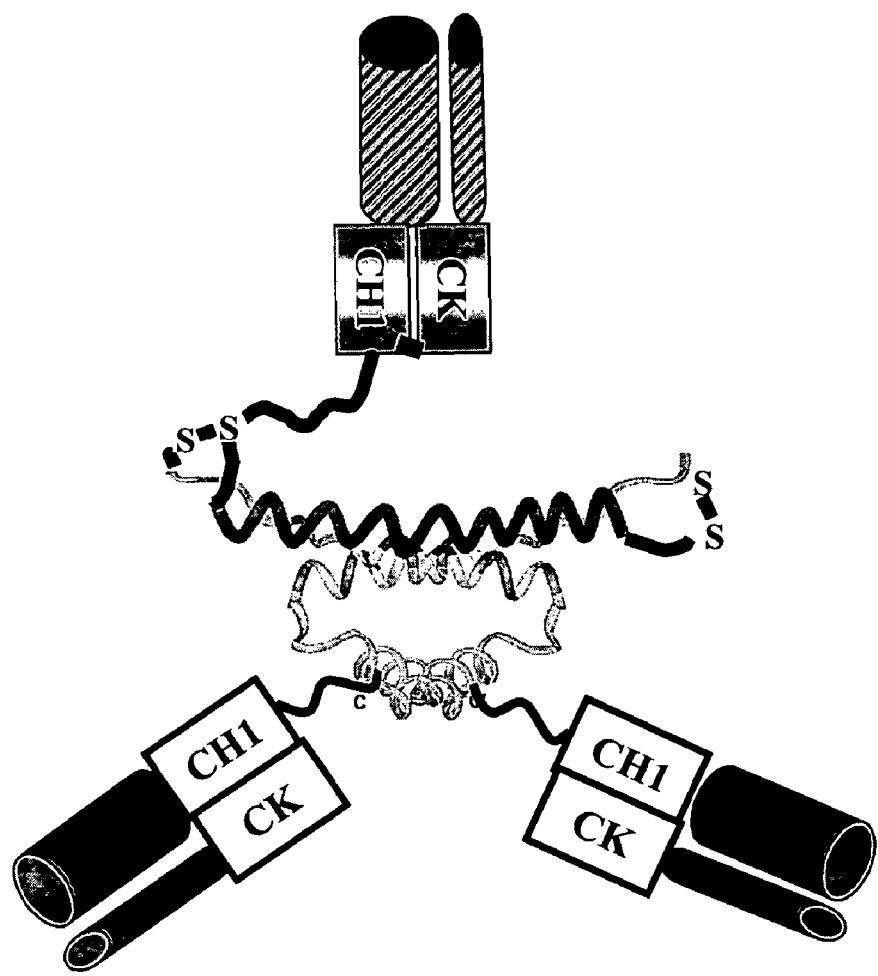
FIG. 8 shows a schematic diagram of TF2.

Following the successful creation of TF1, an analog designated TF2 (FIG. 8) was also obtained by reacting C-DDD2-Fab-hMN-14 with h679-Fab-AD2. TF2 has two potential advantages over TF1. First, C-DDD2-Fab-hMN-14 is produced at a 10-fold higher level than N-DDD2-Fab-hMN-14. Secondly, fusion proteins with C-terminal DDD domains exhibit a markedly stronger CEA-binding avidity than those with N-terminal DDD domains. This is likely attributed to the arrangement of the domains, where the binding of the N-DDD variants may be compromised due to steric interference.

A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involving TCEP reduction, HIC chromatography, DMSO oxidation, and IMP-291 affinity chromatography were the same as described for TF1. Before the addition of TCEP, SE-HPLC did not show any evidence of $a_2b$ formation (not shown). Instead there were peaks corresponding to $a_4$ (8.40 min; 215 kDa), $a_2$ (9.32 min; 107 kDa) and b (10.33 min; 50 kDa). Addition of 5 mM TCEP rapidly resulted in the formation of $a_2b$ complex as demonstrated by a new peak at 8.77 min (not shown), consistent with a 157 kDa protein expected for the binary structure. TF2 was purified to near homogeneity by IMP-291 affinity chromatography (not shown). SE-HPLC analysis of the IMP-291 unbound fraction demonstrates the removal of $a_4$, $a_2$ and free kappa chains from the product (not shown).

Non-reducing SDS-PAGE analysis demonstrated that the majority of TF2 exists as a large, covalent structure with a relative mobility near that of IgG (not shown). The additional bands suggest that disulfide formation is incomplete under the experimental conditions. Reducing SDS-PAGE shows that any additional bands apparent in the non-reducing gel are product-related (not shown), as only bands representing the constituent polypeptides of TF2 are evident. However, the relative mobilities of each of the four polypeptides are too close to be resolved. MALDI-TOF mass spectrometry (not shown) revealed a single peak of 156,434 Da, which is within 99.5% of the calculated mass (157,319 Da) of TF2.

The functionality of TF2 was determined by BIACORE as described for TF1. TF2, C-DDD1-hMN-14+h679-AD1 (used as a control sample of noncovalent $a_2b$ complex), or C-DDD2-hMN-14+h679-AD2 (used as a control sample of unreduced $a_2$ and b components) were diluted to 1 µg/ml (total protein) and pass over a sensorchip immoblized with HSG. The response for TF2 was approximately two-fold that of the two control samples, indicating that only the h679-Fab-AD component in the control samples would bind to and remains on the sensorchip. Subsequent WI2 IgG injections demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip also corresponds to two fully functional binding sites, each contributed by one subunit of C-DDD2-Fab-hMN-14. This was confirmed by the ability of TF2 to bind two Fab fragments of WI2 (not shown).

The relative CEA-binding avidity of TF2 was determined by competitive ELISA. Plates were coated (0.5 μg/well) with a fusion protein containing the A3B3 domain of CEA, which is recognized by hMN-14. Serial dilutions of TF1, TF2 and hMN-14 IgG were made in quadruplicate and incubated in wells containing HRP-conjugated hMN-14 IgG (1 nM). The data indicate that TF2 binds CEA with an avidity that is at least equivalent to that of IgG and two-fold stronger than TF1 (not shown). This is not surprising since previously in a similar assay, C-DDD1-Fab-hMN-14 was found to have a stronger CEA-binding avidity than hMN-14 IgG, which in turn bound more avidly than N-DDD1-Fab-hMN-14. A possible explanation for the apparent improved avidity of C-DDD-Fab-hMN-14 over the parental IgG is that the Gly/Ser linkers in the former provide for a more flexible molecule than IgG. Although the N-DDD variants also possess flexible peptide linkers, the CEA binding sites are positioned close to one another and adjacent to the DDD dimer, resulting in reduced avidity.

Example 15

Serum Stability of TF1 and TF2

TF1 and TF2 were designed to be stably tethered structures that could be used in vivo where extensive dilution in blood and tissues would occur. The stability of TF2 in human sera was assessed using BIACORE. TF2 was diluted to 0.1 mg/ml in fresh human serum, which was pooled from four donors, and incubated at 37° C. under 5% $CO_2$ for seven days. Daily samples were diluted 1:25 and then analyzed by BIACORE using an IMP-239 HSG sensorchip. An injection of WI2 IgG was used to quantify the amount of intact and fully active TF2. Serum samples were compared to control samples that were diluted directly from the stock. TF2 is highly stable in serum, retaining 98% of its bispecific binding activity after 7 days (not shown). Similar results were obtained for TF1 in either human or mouse serum (not shown).

Example 16

Biodistribution of TF2 in Tumor-Bearing Mice

The biodistribution studies were performed for TF2 in female athymic nude mice bearing s.c. human colorectal adenocarcinoma xenografts (LS 174T). Cells were expanded in tissue culture until enough cells had been grown to inject 50 mice s.c. with $1 \times 10^7$ cells per mouse. After one week, tumors were measured and mice assigned to groups of 5 mice per time-point. The mean tumor size at the start of this study was 0.141±0.044 $cm^3$. All the mice were injected with 40 μg $^{125}$I-TF2 (250 pmoles, 2 μCi). They were then sacrificed and necropsied at 0.5, 2, 4, 16, 24, 48, and 72 hrs post-injection. A total of 35 mice were used in this study. Tumor as well as various tissues were removed and placed in a γ-counter to determine percent-injected dose per gram (% ID/g) in tissue at each time-point.

Radioiodination of $^{125}$I-TF2 resulted in 2.7% unbound isotope with a specific activity of 1.48 mCi/mg. The labeled sample was then subjected to SE-HPLC alone and after mixing with a 20-fold molar excess of CEA. Approximately 83% of the TF2 eluted off with a retention time of 10.1 minutes. There was 9% aggregated material (RT=9.03 min) and 8% low molecular weight material (RT=14.37 min) in the labeled TF2. When mixed with CEA, 95% of the labeled TF2 shifted to a high molecular weigh species (RT=7.25 min). These results indicated that the labeled preparation was acceptable for administration to the tumor-bearing mice.

Table 1 presents the calculated % ID/g values in the tumors and various tissues. Peak tumor uptake occurred at 4 h post-injection (10.3±2.1% ID/g). Between 16 and 24 h post-injection, the amount of TF2 in the tumor is not significantly different (5.3±1.1% ID/g and 5.37±0.7% ID/g), indicating that peptide could be administered anytime between these two time-points, depending on blood values, without impacting tumor targeting. Uptake and clearance of TF2 from normal tissues was very similar to what has been observed previously for TF1. Both TF1 and TF2 appeared to favor clearance through the RES system (spleen and liver).

The blood PK for TF2 in tumor-bearing mice were also evaluated and found to exhibit biphasic clearance. These data were analyzed using two-compartment analysis provided in the WinNonlin Nonlinear Estimation Program (v. 4.1) and the parameters determined are shown in Table 2.

Example 17

Pretargeting with TF2 in Tumor Bearing Mice

A pretargeting study was performed with TF2 in female athymic nude mice bearing s.c. human colorectal adenocarcinoma xenografts (LS 174T). Cells were expanded in tissue culture until enough cells had been grown to inject 55 mice s.c. with $1 \times 10^7$ cells per mouse. After one week, tumors were measured and mice assigned to groups of 5 mice per time-point. The mean tumor size at the start of this study was 0.105±0.068 $cm^3$. Twenty mice were injected with 80 μg $^{125}$I-TF2 (500 pmoles, 2 μCi) and 16 h later administered $^{99m}$Tc-IMP-245 (40 μCi, 92 ng, 50 pmoles). The mice were sacrificed and necropsied at 0.5, 1, 4, and 24 h post-peptide injection. In addition, 3 mice of the 24 h time-point groups were imaged on a γ-camera at 1, 4, and 24 h post-injection. As a control, 3 additional mice received only $^{99m}$Tc-IMP-245 (no pretargeting) and were imaged at 1, 4, and 24 h post-injection, before being necropsied after the 24 h imaging session. Tumor as well as various tissues were removed and placed in a y-counter to determine % ID/g in tissue at each time-point.

The % ID/g values determined for $^{125}$I-TF2 and $^{99m}$Tc-IMP-245 pretargeted with $^{125}$I-TF2 are summarized in Tables 3 and 4, respectively. TF2 levels remained relatively unchanged over the first 4 h following injection of the peptide (or 20 h post-TF2 administration), ranging from 6.7±1.6% ID/g at 0.5 h post-peptide injection (16.5 h post-TF2 administration) to 6.5±1.5% ID/g at the 4 h time-point (20 h post-TF2 injection). Tumor uptake values (% ID/g) of IMP-245 pretargeted with TF2 were 22±3%, 30±14%, 25±4%, and 16±3% at 0.5, 1, 4, and 24 h post-peptide injection.

In terms of normal tissues, there was significantly less peptide in the liver, lungs, and blood at each time-point examined in the mice pretargeted with TF2 in comparison to the results obtained with other pretargeting agents developed to date (Rossi, et al. Clin Cancer Res. 2005; 11(19 Suppl): 7122s-7129s). These data indicate that the TF2 clears efficiently through normal organs without leaving behind any residual fragments that might bind subsequently administered peptide.

The high tumor uptake coupled with lower levels in normal tissues yielded excellent tumor:non-tumor (TlNT) ratios (Table 5), thus validating TF2 as a suitable pretargeting agent for localizing di-HSG-based effectors to CEA-producing tumors.

Example 18

Generation of TF2 Using a Glutathione Redox System

As an alternative embodiment to the methods disclosed in Examples 13 and 14 above, a stably tethered structure such as TF1 or TF2 may be generated using a glutathione redox system to form specific disulfide bonds linking the stably tethered structure together.

A simplified and efficient method for generating TF2 was accomplished as follows. The entire process was conducted at room temperature. C-DDD2-Fab-hMN-14 (Protein L-purified) and h679-Fab-AD2 (IMP-291-purified) were first mixed in roughly stoichiometric concentrations in 1 mM EDTA, PBS, pH 7.4. Reduced glutathione was added to a final concentration of 1 mM. After 30 minutes, oxidized glutathione was added to a final concentration of 2 mM. BIACORE analysis demonstrated that TF2 formation was 50% complete 2 minutes after addition of oxidized glutathione and 100% complete within 4 hours. TF2 was purified to near homogeneity by IMP-291 affinity chromatography as described in Example 14 above.

Example 19

Site-Specific Pegylation of Ganulocyte Macrophage Colony-Stimulating Factor (GM-CSF)

Recombinant human GM-CSF (14 kDa) is used clinically to treat a variety of hematological disorders. A limitation of current GM-SCF products is short circulating half-lives, which therefore must be administered to patients by daily injection for optimal effectiveness. One approach that has been used to prolong the circulation half-lives of protein therapeutics is to modify the protein with polyethylene glycol (PEG) to increase its effective size. However, all present methods known for conjugating PEG to proteins (pegylation) are not optimal, and usually require modification of the protein of interest to achieve site-specific coupling (Doherty et al., Bioconjugate Chem. 2005, 16: 1291-1298). Even with such modifications, the conjugation yields are varied and the resulting products may not be homogenous.

Site-specific pegylation of GM-CSF with quantitatively yield can be achieved with the present invention (hereafter referred to as the Dock-and-Lock (DNL) method or technology) as outlined below. The DDD2 sequence is fused to the C-terminus of GM-CSF via a spacer to produce a dimer of GM-SCF, creating a docking site for AD2, which is conjugated to PEG to obtain PEG-AD2. The formation of pegylated GM-CSF results by combining GM-CSF-DDD2 and PEG-AD2 under similar conditions as described for TF2. It is noted that in addition to prolonging the circulation half-lives, the dimeric structure of GM-CSF in the pegylated product should be more potent than the current monomeric form of GM-CSF. This strategy can be applied to other cytokines (such as recombinant human IL-2), enzymes (such as recombinant human arginase), or biologically active peptides (such as the peptide agonist of the thrombopoietin receptor, see Cwirta et al., Science 1997, 276: 1696-1699) or peptide mimetics that have a need for longer circulation half-lives to improve therapeutic efficacy.

Example 20

Novel Immunodrugs Enabled by the DNL Technology

A fusion protein as a B component that will allow the conjugation of a cytotoxic drug of interest can be produced and used for coupling to a targeting protein produced as an A component, resulting in a novel type of immunodrug as outlined below. First, a well-expressed immunoglobulin human light chain is selected as the scafold or carrier protein, which is fused to the AD2 sequence at its C-terminus. To prevent the formation of light chain dimer, the terminal cysteine (which forms a disulfide linkage with the Fd chain) is replaced with a serine. Further, at least one N-glycosylation site (the tripeptide sequence N-X-T) is engineered into the light chain to enable the addition of oligosaccharides, which can be produced recombinantly in high yield, purified to homogeneity, and used as a substrate for drug conjugation via appropriate chemistries, for example, as described by Shih et al for the conjugation of anthracyclin to amino-dextran (Cancer Res. 1991; 51: 4192-4198). Such drug-containing B-components can be combined with a variety of A components comprising DDD2 linked to a binding structure that possesses the targeting and internalization functions. Alternatively, a drug-containing amino-dextran derivatized with AD2 is combined with a suitable A component to enable target specific drug therapy. Other well-expressed recombinant molecules can also be selected as the scaffold or carrier proteins for drug conjugation.

Example 21

Targeting of Pathogens to Neutrophils for Kill

A broad-spectrum anti-infective agent potentially useful for treating the diseases caused by a variety of pathogens including influenza A virus, *Candida albicans*, and *E. coli* has been reported recently for a chemical conjugate comprising recombinant human surfactant protein fragment D (rfhSP-D) and the Fab of an anti-CD89 antibody (Tacken et al., J. Immunol. 2004, 172: 4934-4940). The DNL technology can be used for producing stably tethered complexes that will also target pathogens to neutrophils for kill as follows. A truncated fragment of hSP-D comprising the α-helical coiled coil neck domain and the C-terminal carbohydrate recognition domains (CRDs) is fused at the N-terminus to DDD2 to generate an A structure that binds multivalently to a pathogen through CRDs. To provide targeting for the FcRs on neutrophils the A structure is linked to a B component composed of a fusion protein of anti-CD89 Fab and AD2, resulting in a stable complex composed of two CRDs of hSP-D and one Fab of anti-CD89. Similar anti-infective agents can be prepared by substituting human surfactant protein A (hSP-A) for hSP-D and other antibodies such as those for CD3 and CD64.

Example 22

Multivalent, Multispecific Structures Generated with Protein-Protein Interaction Domains not Derived from PKA and AKAPs Two basic strategies are envisioned. The first strategy depends on searching and evaluating other naturally occurring protein-protein interaction domains that may be suitable for substituting the roles of DDD and AD. For example, the N-terminal dimerization domain of HNF-1a may replace DDD and the dimerization cofactor for HFN-1 (DcoH) may replace AD. The second strategy is outlined below.

Human p53 is a modular protein consisting of discrete functional domains. The C-terminal residues 325-355 (Scheme I) of human p53, termed the tetramerization domain (p53tet), spontaneously form a tetramer in solution, which is in fact a dimer of dimers with a weak affinity (Kd ~2 uM)

between the two dimers. However, the two monomers in each dimer are strongly associated, with a Kd reported to be lower than $10^{-15}$ M (Brokx et al., J. Biol. Chem. 2003; 278: 2327-2332). Fusion proteins containing p53tet are therefore expected to form very tightly bound dimers, as fusion proteins containing the DDD sequence of human RIIα of PKA. To ligate a second structure to the dimer of p53tet, binding peptides for p53tet with Kd of 1 uM or lower and containing 15 to 50 residues are selected using the yeast 2-hybrid system or a suitable phage display libraries. The peptide with the highest affinity (i.e. the lowest value for Kd) is derivatized with cysteine if necessary and fused to a protein of interest, which can be stably tethered to the dimer of p53tet.

Scheme I
GEYFTLQIRGRERFEMFRELNEALELKDAQA        (SEQ ID NO: 28)

Production and Use of Hexavalent IgG-Based DNL Structures (HIDS)

Example 23

Hexameric Constructs

The DNL technology described above for formation of $a_2b$ complexes was applied to generate hexavalent IgG-based DNL structures (HIDS). Two types of modules, which were produced as recombinant fusion proteins, were combined to generate a variety of HIDS. Fab-DDD2 modules were as described for use in generating Tri-Fab structures (Rossi et al. *Proc Natl Acad Sci USA*. 2006; 103(18): 6841-6, see Examples above). The Fab-DDD2 modules form stable homodimers that bind to AD2-containing modules. To generate HIDS, two types of IgG-AD2 modules were created to pair with the Fab-DDD2 modules: C-H-AD2-IgG and N-L-AD2-IgG.

Figure 9:
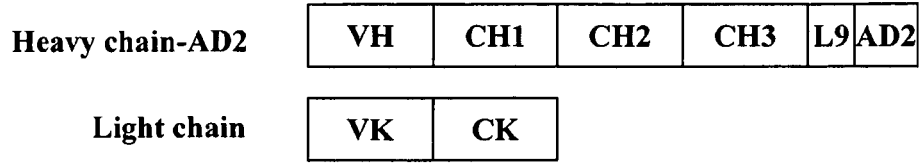
FIG. 9 is a sketch of C-H-AD2-IgG. (A) Arrangement of cDNA/polypeptide sequences for heavy chain-AD2 and light chain. (B) Schematic representation of a C-H-AD2-IgG.
Figure 9:
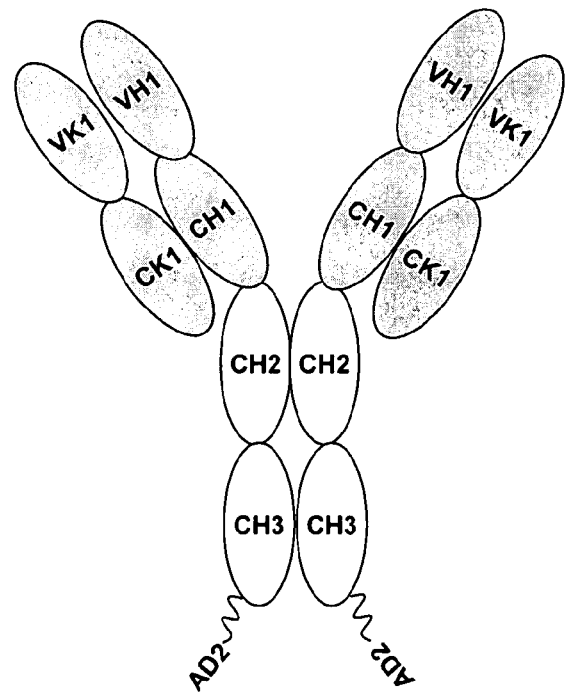
Figure 10:
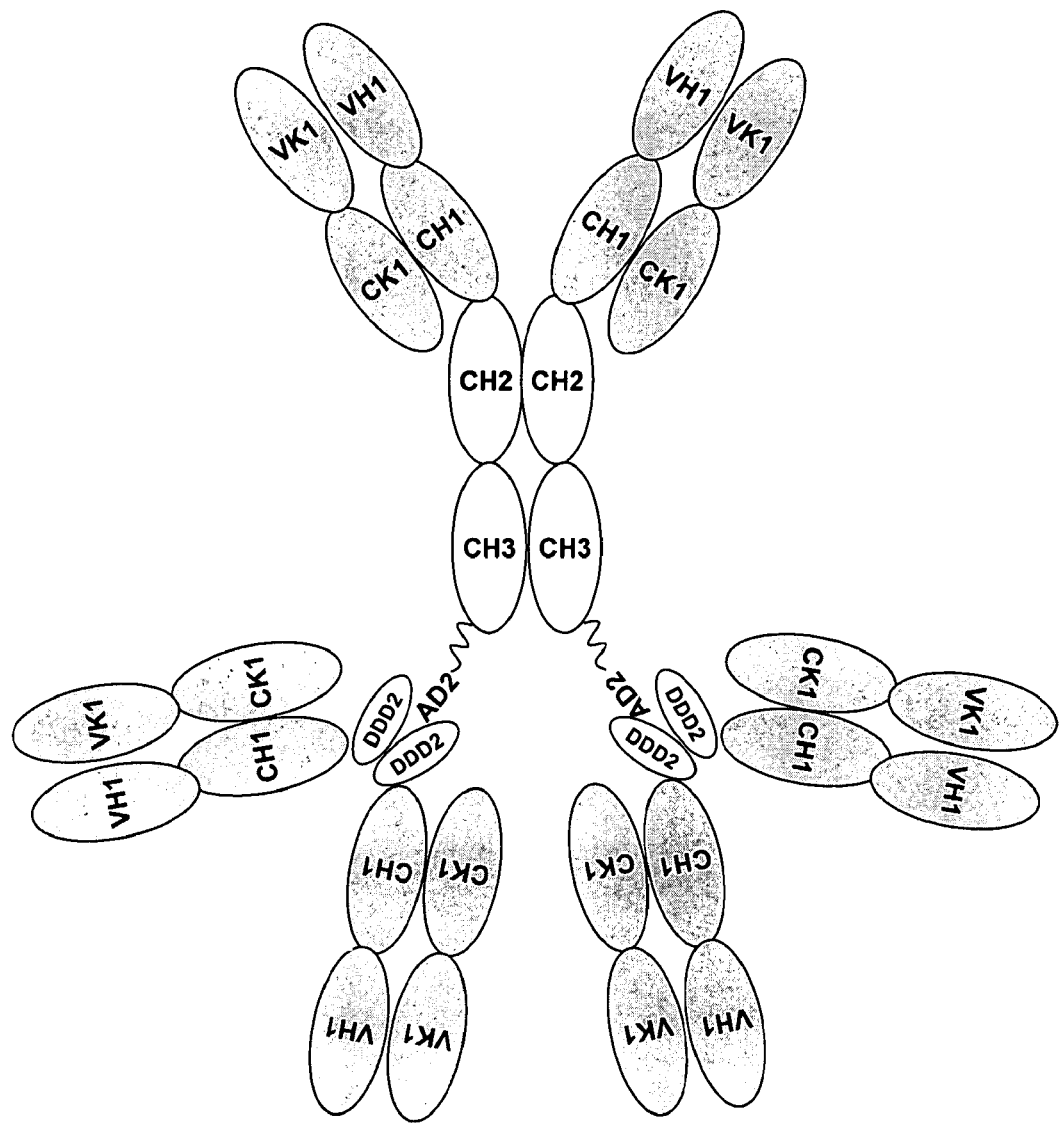
FIG. 10 is a schematic representation of a monospecific HIDS (hexavalent IgG-based DNL structure) resulting from the combination of C-H-AD2-IgG and Fab-DDD2 modules.
Figure 11:
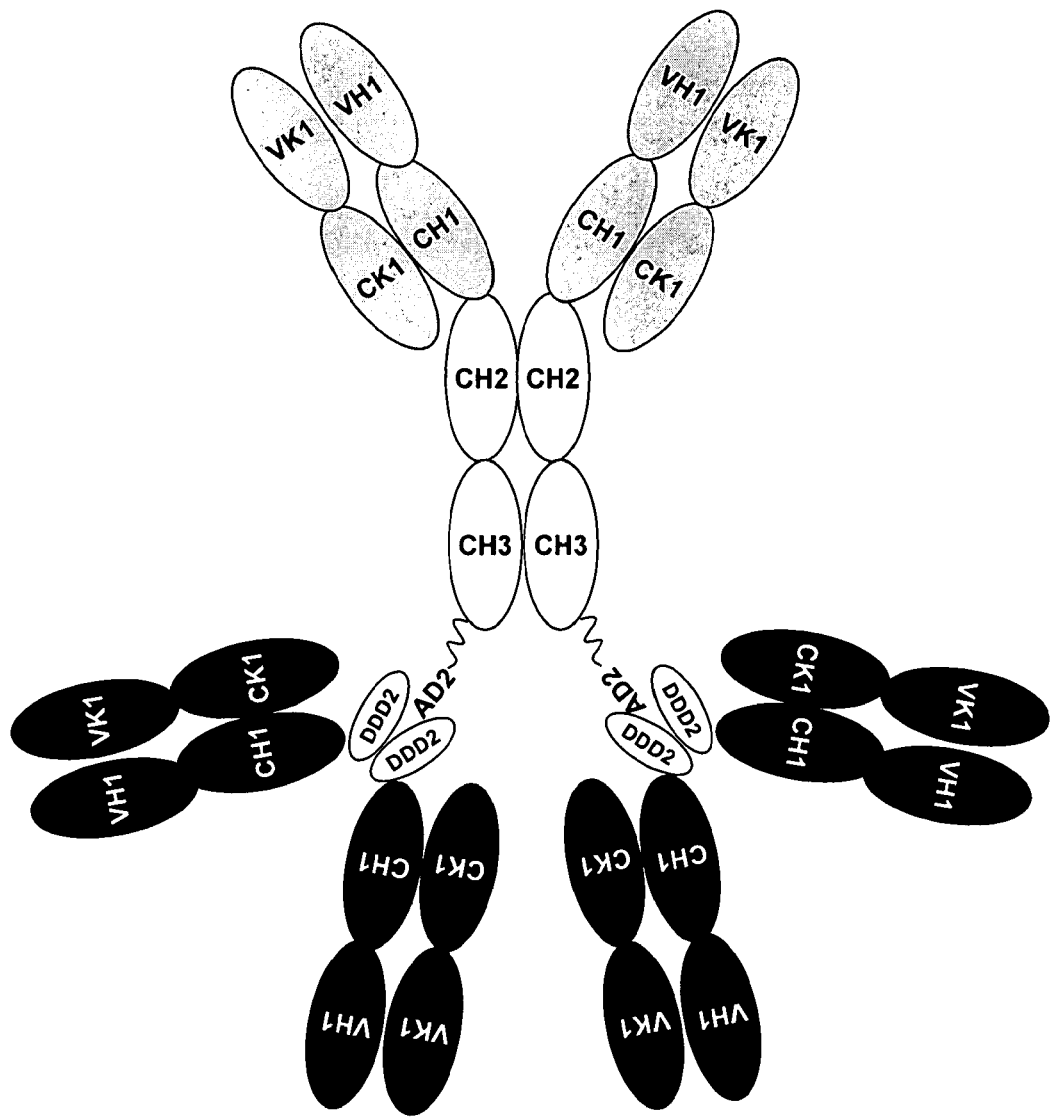
FIG. 11 is a schematic representation of a bispecific HIDS resulting from the combination of C-H-AD2-IgG and Fab-DDD2 modules.

C-H-AD2-IgG modules have an AD2 peptide fused to the carboxyl terminus (C) of the heavy (H) chain of IgG via a 9 amino acid residue peptide linker (FIG. 9A). The DNA coding sequences for the linker peptide (GSGGGGSGG, SEQ ID NO:29) followed by the AD2 peptide (CGQIEYLAKQIVDNAIQQAGC, SEQ ID NO:4) are coupled to the 3' end of the CH3 (heavy chain constant domain 3) coding sequence by standard recombinant DNA methodologies, resulting in a contiguous open reading frame. When the heavy chain-AD2 polypeptide is co-expressed with a light chain polypeptide, an IgG molecule is formed possessing two AD2 peptides (FIG. 9B), which can therefore bind two Fab-DDD2 dimers. The C-H-AD2-IgG module can be combined with any Fab-DDD2 module to generate a wide variety of hexavalent structures composed of an Fc fragment and six Fab fragments. If the C-H-AD2-IgG module and the Fab-DDD2 module are derived from the same parental monoclonal antibody (MAb) the resulting HIDS is monospecific with 6 binding arms to the same antigen (FIG. 10). If the modules are instead derived from two different MAbs then the resulting HIDS are bispecific, with two binding arms for the specificity of the C-H-AD2-IgG module and 4 binding arms for the specificity of the Fab-DDD2 module (FIG. 11).

Figure 12:
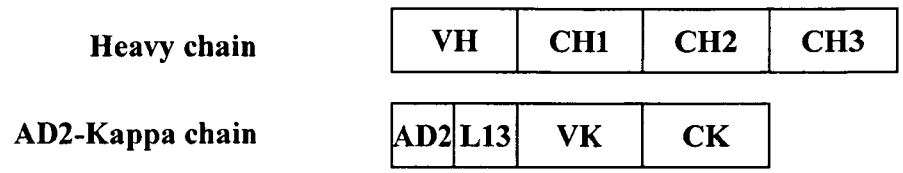
FIG. 12 is a sketch of N-K-AD2-IgG. (A) Arrangement of cDNA/polypeptide sequences for heavy chain and AD2-light chain. (B) Schematic representation of a N-K-AD2-IgG.
Figure 12:
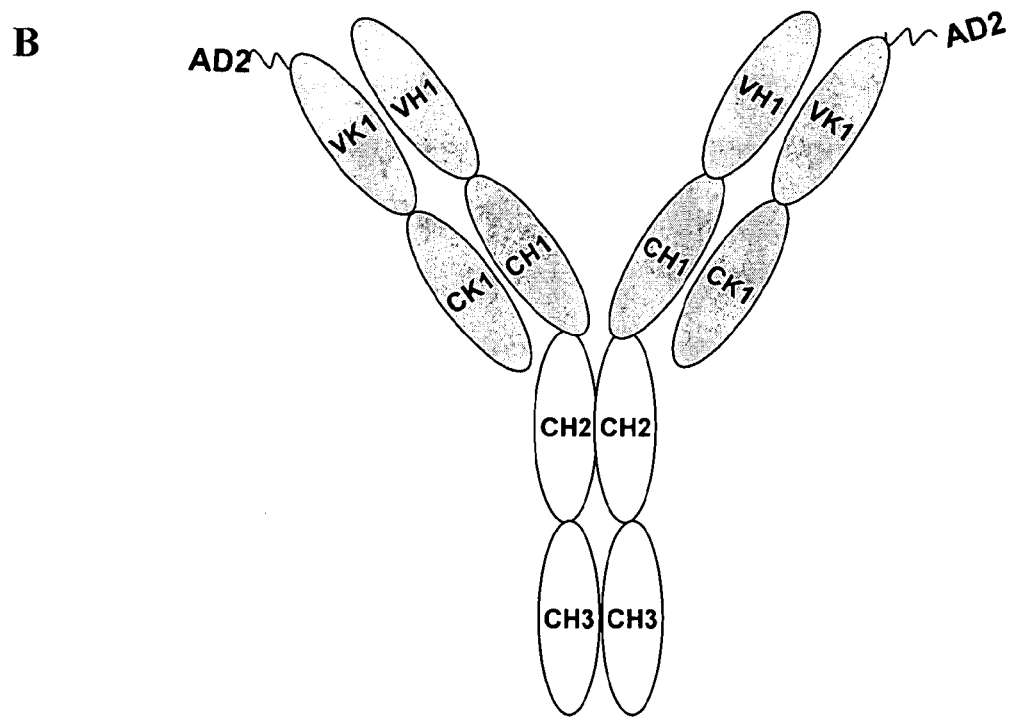
Figure 13:
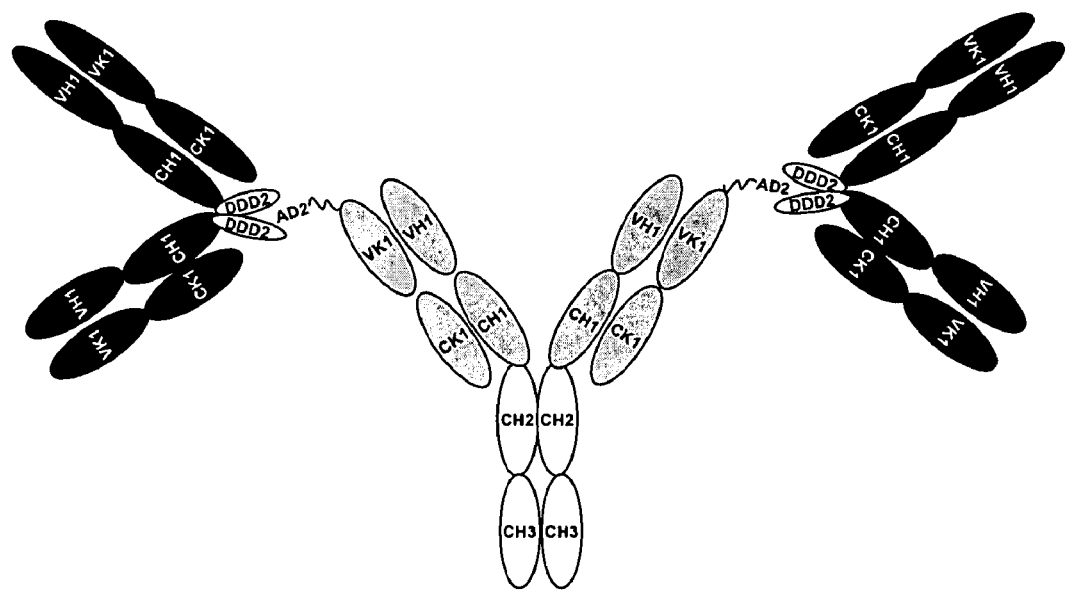
FIG. 13 is a schematic representation of a bispecific HIDS resulting from the combination of N-K-AD2-IgG and Fab-DDD2 modules.

N-L-AD2-IgG is an alternative type of IgG-AD2 module in which an AD2 peptide is fused to the amino terminus (N) of the light (L) chain of IgG via a 13 amino acid residue peptide linker (FIG. 12A). The L chain can be either Kappa (K) or Lambda (λ) and will also be represented as K in the text or Figures with the same meaning. The DNA coding sequences for the AD2 peptide (CGQIEYLAKQIVDNAIQQAGC, SEQ ID NO:4) followed by the linker peptide (GGGGSGGGSGGG, SEQ ID NO:30) are coupled to the 5' end of the coding sequence for the variable domain of the L chain (VL), resulting in a contiguous open reading frame. When the AD2-kappa chain polypeptide is co-expressed with a heavy chain polypeptide, an IgG molecule is formed possessing two AD2 peptides (FIG. 12B), which can therefore bind two Fab-DDD2 dimers. The N-L-AD2-IgG module can be combined with any Fab-DDD2 module to generate a wide variety of hexavalent structures composed of an Fc fragment and six Fab fragments arranged as shown in FIG. 13.

Example 24

Creation of C-H-AD2-IgG-pdHL2 Expression Vectors

The pdHL2 mammalian expression vector has been used to mediate the expression of many recombinant IgGs. A plasmid shuttle vector was produced to facilitate the conversion of any IgG-pdHL2 vector into a C-H-AD2-IgG-pdHL2 vector. The gene for the Fc (CH2 and CH3 domains) was amplified using the pdHL2 vector as a template and the oligonucleotides Fc BglII Left and Fc Bam-EcoRI Right as primers.

Fc BglII Left
(SEQ ID NO: 31)
5'-AGATCTGGCGCACCTGAACTCCTG-3'

Fc Bam-EcoRI Right
(SEQ ID NO: 32)
5'-GAATTCGGATCCTTTACCCGGAGACAGGGAGAG-3'

Figure 14:
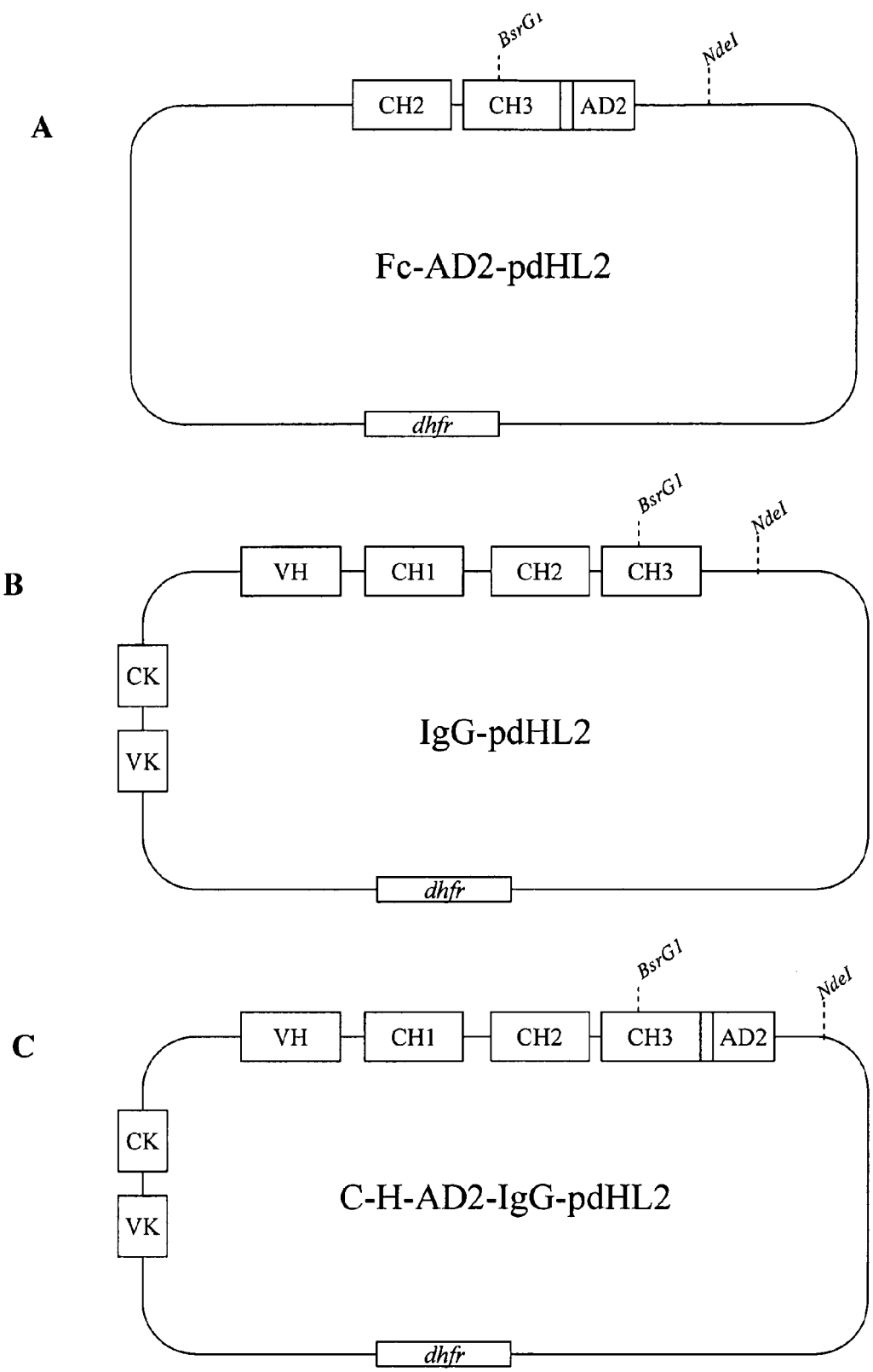
FIG. 14 shows sketches of (A) Fc-AD2-pdHL2 shuttle vector, (B) IgG-pdHL2 mammalian expression vector and (C) C-H-AD2-IgG-pdHL2 mammalian expression vector.

The amplimer was cloned in the pGemT PCR cloning vector. The Fc insert fragment was excised from pGemT with XbaI and BamHI restriction enzymes and ligated with AD2-pdHL2 vector that was prepared by digestion of h679-Fab-AD2-pdHL2 with XbaI and BamHI, to generate the shuttle vector Fc-AD2-pdHL2 (FIG. 14A).

To convert any IgG-pdHL2 expression vector (FIG. 14B) to a C-H-AD2-IgG-pdHL2 expression vector (FIG. 14C), an 861 bp BsrGI/NdeI restriction fragment is excised from the former and replaced with a 952 bp BsrGI/NdeI restriction fragment excised from the Fc-AD2-pdHL2 vector. BsrGI cuts in the CH3 domain and NdeI cuts downstream (3') of the expression cassette.

Example 25

Production of C-H-AD2-hLL2 IgG

Figure 15:
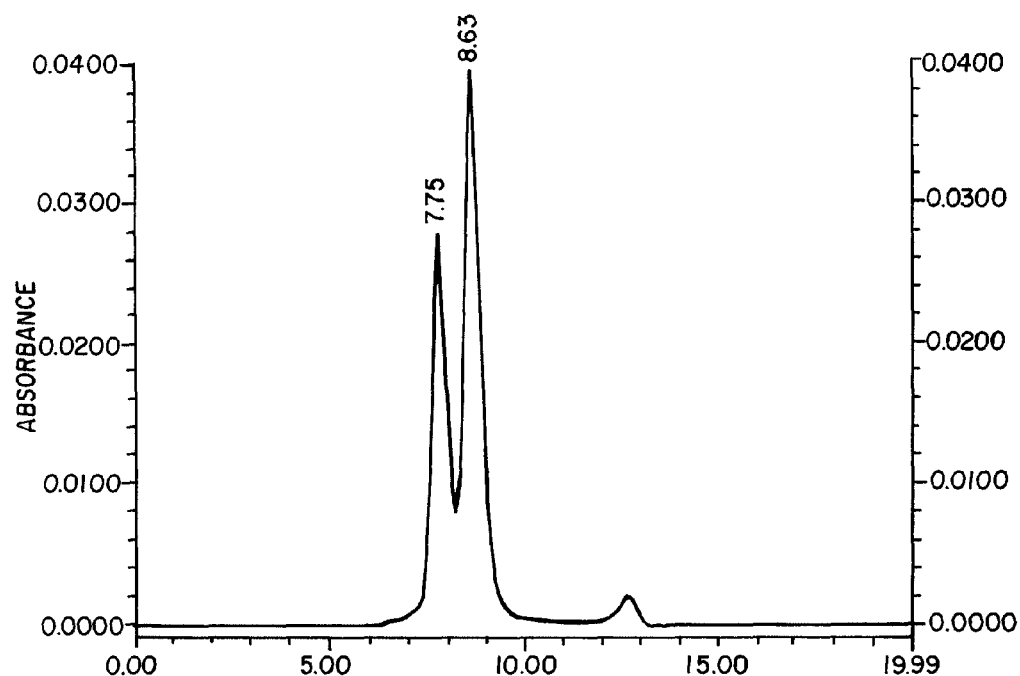
FIG. 15 shows SE-HPLC analysis of Protein A-purified C-H-AD2-hLL2-IgG. Peaks representing monomeric and dimeric forms are indicated.
Figure 16:
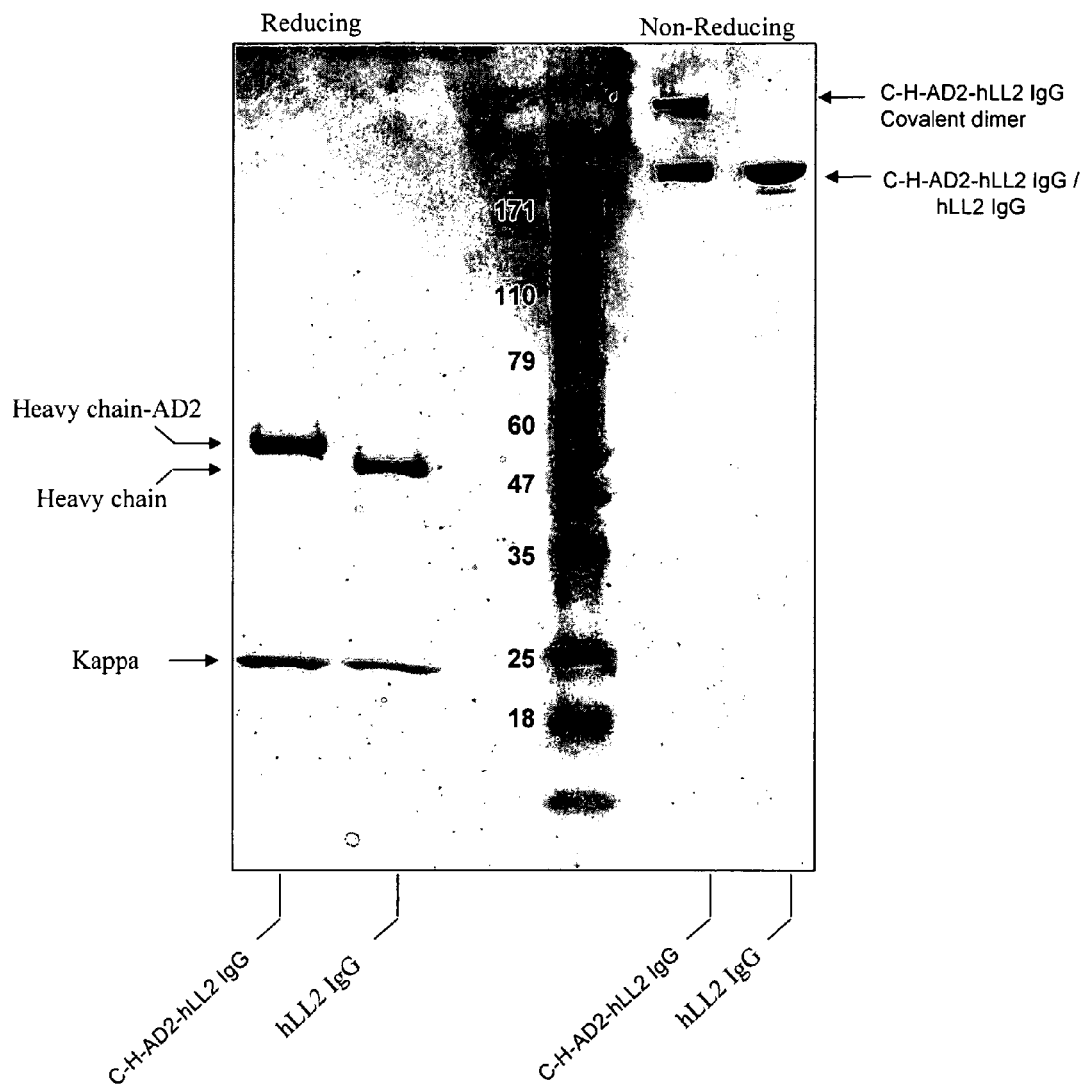
FIG. 16 shows SDS-PAGE analysis of Protein A-purified C-H-AD2-hLL2-IgG under reducing and non-reducing conditions. Bands representing heavy chain-AD2, heavy chain and kappa light chain are indicated for reduced lanes. Bands representing C-H-AD2-hLL2-IgG and the covalent dimer are indicated for non-reduced lanes. The positions of molecular weight markers are indicated.

Epratuzumab, or hLL2 IgG, is a humanized anti-human CD22 MAb. An expression vector for C-H-AD2-hLL2 IgG was generated from hLL2 IgG-pdHL2, as described in Example 24, and used to transfect Sp2/0 myeloma cells by electroporation. Following transfection, the cells were plated in 96-well plates and transgenic clones were selected in media containing methotrexate. Clones were screened for C-H-AD2-hLL2 IgG productivity by a sandwich ELISA using 96-well microtitre plates coated with an hLL2-specific anti-idiotype MAb and detection with peroxidase-conjugated anti-human IgG. Clones were expanded to roller bottles for protein production and C-H-AD2-hLL2 IgG was purified from the spent culture media in a single step using Protein-A affinity chromatography. SE-HPLC analysis resolves two protein peaks (FIG. 15). The retention time of the slower eluted peak (8.63 min) is similar to hLL2 IgG. The retention time of the faster eluted peak (7.75 min) is consistent with a ~300 kDa protein. It was later determined that this peak represents disulfide linked dimers of C-H-AD2-hLL2-IgG. This dimer is reduced to the monomeric form during the DNL reaction. SDS-PAGE analysis demonstrated that the purified C-H-AD2-hLL2-IgG consists of both monomeric and disulfide-linked dimeric forms of the module (FIG. 16). Protein bands representing these two forms are evident by SDS-PAGE under non-reducing conditions, while under reducing conditions all of the forms are reduced to two bands representing the constituent polypeptides (Heavy chain-AD2 and kappa chain). No other contaminating bands were detected.

Example 26

Production of C-H-AD2-hA20 IgG hA20 IgG is a humanized anti-human CD20 MAb. An expression vector for C—H-AD2-hA20 IgG was generated from hA20 IgG-pDHL2, as described in Example 24, and used to transfect Sp2/0 myeloma cells by electroporation. Following transfection, the cells were plated in 96-well plates and transgenic clones were selected in media containing methotrexate. Clones were screened for C-H-AD2-hA20 IgG productivity by a sandwich ELISA using 96-well microtitre plates coated with an hA20-specific anti-idiotype MAb and detection with peroxidase-conjugated anti-human IgG. Clones were expanded to roller bottles for protein production and C-H-AD2-hA20 IgG was purified from the spent culture media in a single step using Protein-A affinity chromatography. SE-HPLC and SDS-PAGE analyses gave very similar results to those obtained for C-H-AD2-hLL2 IgG in Example 25.

Example 27

Production of N-L-AD2-hA20 IgG

A 197 bp DNA duplex comprising the coding sequence for the light chain leader peptide, AD2, a 13-residue peptide linker and the first four residues of hA20 Vk (all in frame) was generated as follows. Two 100-mer synthetic oligonucleotides, which overlap by 35 base-pairs, were made fully duplex by primer extension using Taq polymerase.

```
LP-AD2-L13 Top
                                      (SEQ ID NO: 33)
CATCATGGGATGGAGCTGTATCATCCTCTTCTTGGTAGCAACAGCT
ACAGGTGTCCACTCCGACGGCTGTGGCCAGATCGAGTACCTGGCCA
AGCAGATC

LP-AD2-L13 Bottom
                                      (SEQ ID NO: 34)
CCGCCAGACCCGCCACCTCCGGACCCTCCGCCGCCGCAGCCGGCCT
GCTGGATGGCGTTGTCCACGATCTGCTTGGCCAGGTACTCGATCTG
GCCACAGC
```

The sequence was amplified by PCR, which appended XbaI and PvuII restriction sites to the 5' and 3' ends, respectively. The amplimer was cloned into pGemT.

```
LP-Left XbaI
                                      (SEQ ID NO: 35)
TCTAGACACAGGACCTCATCATGGGATGGAGCTGTA L13-VK Right PvuII
                                      (SEQ ID NO: 36)
CAGCTGGATGTCACCTCCGCCAGACCCGCCACCTCC
```

The 197 bp XbaI/PvuII fragment was excised from pGemT and ligated with the hA20 VK shuttle vector h2B8-Vk-pBR2, which was prepared by digestion with XbaI and PvuII. The new shuttle vector is AD2-K-hA20-pBR2. A 536 bp XbaI/BamHI restriction fragment was excised from AD2-K-hA20-pBR2 and ligated with hA20-IgG-pDHL2 vector that was prepared by digestion with XbaI and BamHI to generate the expression vector N-L-AD2-hA20-IgG-pdHL2.

N-L-AD2-hA20-IgG-pdHL2 was used to transfect Sp2/0 myeloma cells by electroporation. Following transfection, the cells were plated in 96-well plates and transgenic clones were selected in media containing methotrexate. Clones were screened for N-L-AD2-hA20 IgG productivity by a sandwich ELISA using 96-well microtitre plates coated with an hA20-specific anti-idiotype MAb and detection with peroxidase-conjugated anti-human IgG. Clones were expanded to roller bottles for protein production and N-L-AD2-hA20 IgG was purified from the spent culture media in a single step using Protein-A affinity chromatography.

Figure 17A:
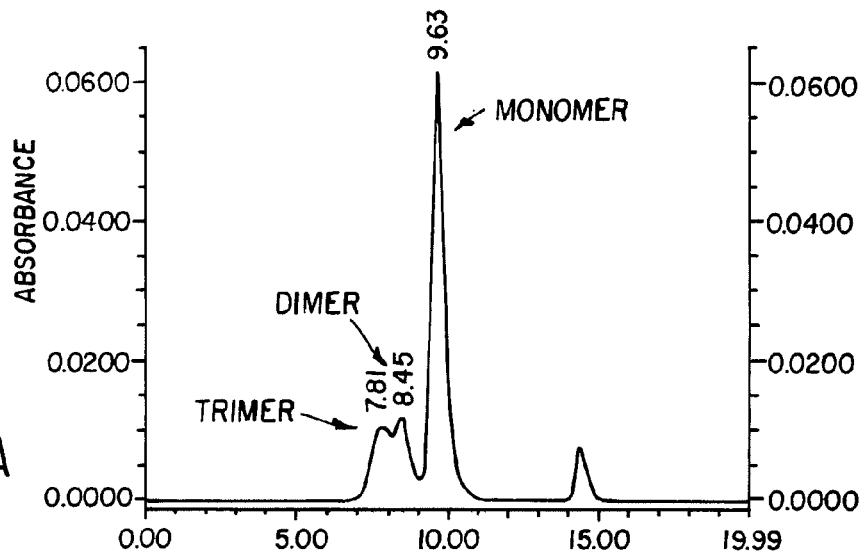
FIG. 17 shows SE-HPLC analysis of Protein A-purified N-K-AD2-hLL2-IgG. (A) Peaks representing monomeric, dimeric and trimeric forms are indicated with arrows. (B) Analysis following reduction with glutathione showing that the dimeric and trimeric forms are converted to the monomeric form.
Figure 17B:
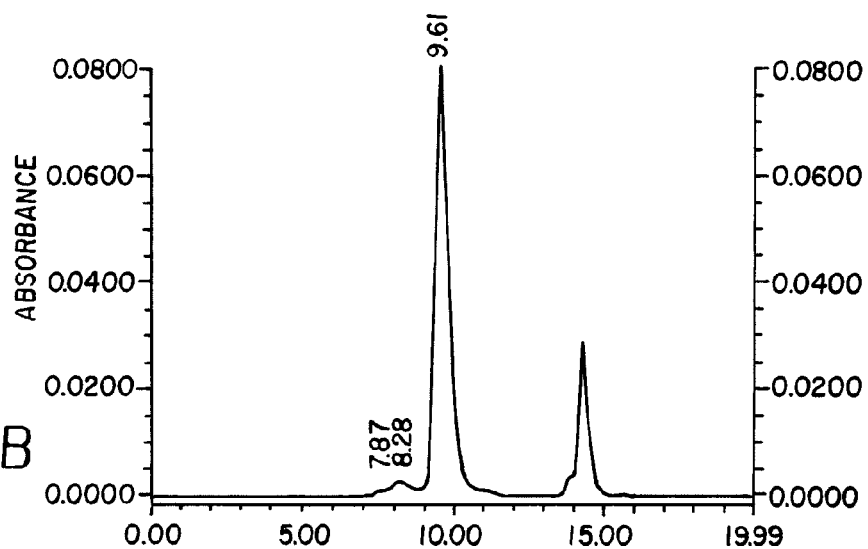
Figure 18:
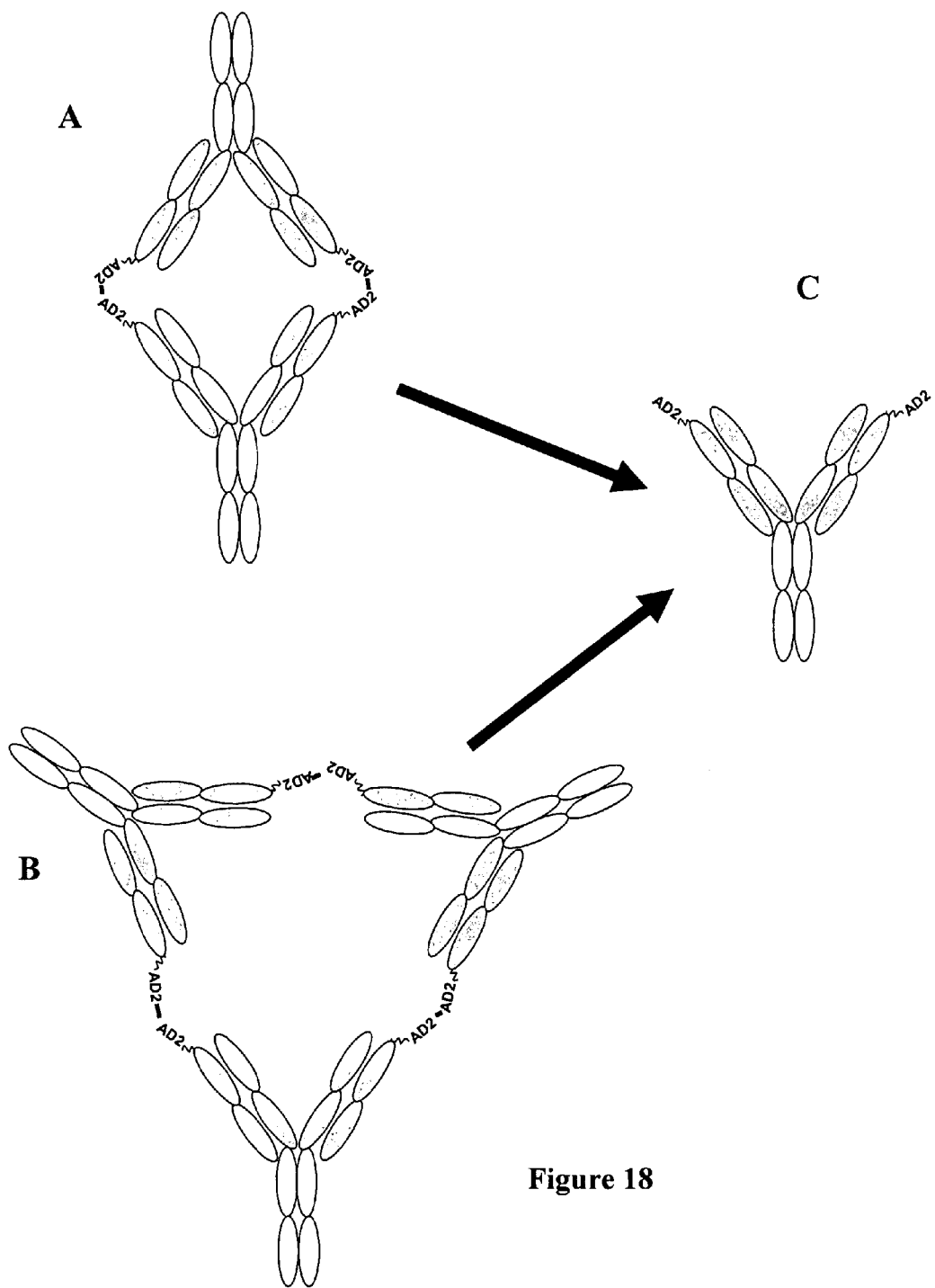
FIG. 18 shows sketches of postulated structures for (A) dimeric and (B) trimeric forms of N-K-AD2-hLL2-IgG, which are converted to (C) the monomeric form by mild reduction.

Size exclusion HPLC showed that the majority of the N-L-AD2-hA20 IgG in the prep is in a monomeric form with a retention time similar to IgG. Two additional peaks likely representing disulfide linked dimeric and trimeric forms and each accounting for approximately 15% of the total protein were also observed (FIG. 17A). Mild reduction of the prep, as is used in the DNL reaction, results in the conversion of the dimeric and trimeric forms to the monomeric form (FIG. 17B). Sketches of the putative structures for the three forms are provided in FIG. 18.

Example 28

Generation of Hex-hA20

The DNL method was used to create Hex-hA20, a monospecific anti-CD20 HIDS, by combining C-H-AD2-hA20 IgG (see Example 26) with hA20-Fab-DDD2. The Hex-hA20 structure contains six anti-CD20 Fab fragments and an Fc fragment (FIG. 10).

Hex-hA20 was made in four steps.

Step 1, Combination: A 210% molar equivalent of (hA20-Fab-DDD2)$_2$ was mixed with C-H-AD2-hA20 IgG. This molar ratio was used because two Fab-DDD2 dimers are coupled to each C-H-AD2-hA20 IgG molecule and an additional 10% excess of the former ensures that the coupling reaction is complete. The molecular weights of C-H-AD2-hA20 IgG and (hA20-Fab-DDD2)$_2$ are 168 kDa and 107 kDa, respectively. As an example, 134 mg of hA20-Fab-DDD2 would be mixed with 100 mg of C-H-AD2-hA20 IgG to achieve a 210% molar equivalent of the former. The mixture is typically made in phosphate buffered saline, pH 7.4 (PBS) with 1 mM EDTA.

Step 2, Mild Reduction: Reduced glutathione (GSH) was added to a final concentration of 1 mM and the solution is held at room temperature (16-25° C.) for 1-24 hours.

Step 3, Mild Oxidation: Following reduction, oxidized glutathione (GSSH) was added directly to the reaction mixture to a final concentration of 2 mM and the solution was held at room temperature for 1-24 hours.

Step 4, Isolation of the DNL product: Following oxidation, the reaction mixture was loaded directly onto a Protein-A affinity chromatography column. The column was washed with PBS and the Hex-hA20 was eluted with 0.1 M Glycine, pH 2.5. Since excess hA20-Fab-DDD2 was used in the reaction, there was no unconjugated C-H-AD2-hA20 IgG, or incomplete DNL structures containing only one (hA20-Fab-DDD2)$_2$ moiety. The unconjugated excess hA20-Fab-DDD2 does not bind to the affinity resin; therefore, the Protein A-purified material contains only the desirable product.

Figure 19:
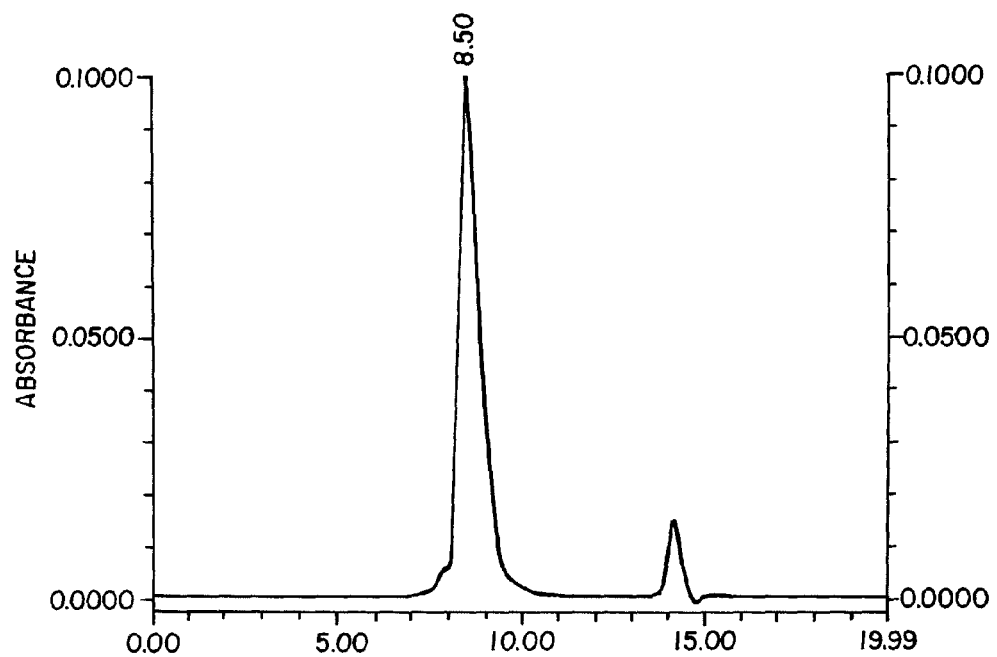
FIG. 19 shows SE-HPLC analysis of Protein A-purified Hex-hA20.
Figure 20:
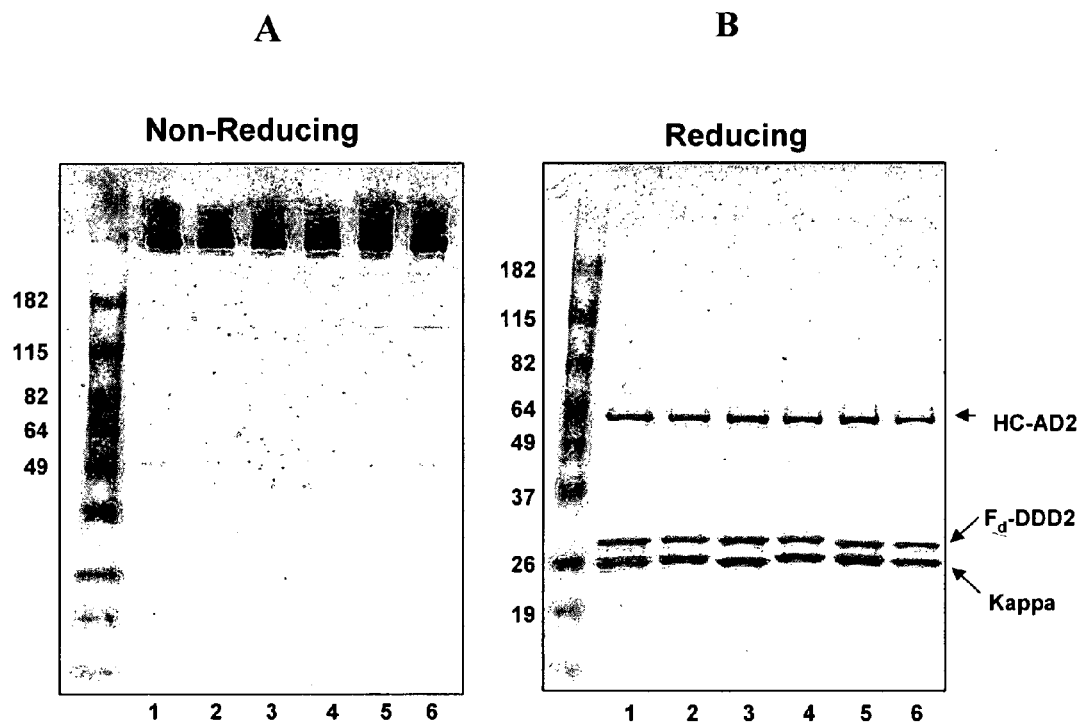
FIG. 20 shows SDS-PAGE analysis of six C-H-AD2-hLL2-IgG-based HIDS. (A) SDS-PAGE under non-reducing conditions. (B) SDS-PAGE under reducing conditions. Bands representing heavy chain-AD2, Fd-DDD2 and kappa light chain are indicated by arrows. The positions of molecular weight markers are indicated.

The calculated molecular weight from the deduced amino acid sequences of the constituent polypeptides is 386 kDa. Size exclusion HPLC analysis showed a single protein peak with a retention time consistent with a protein structure of 375-400 kDa (FIG. 19). SDS-PAGE analysis under non-reducing conditions shows a cluster of high molecular weight bands indicating a large covalent structure (FIG. 20A, lane 3). SDS-PAGE under reducing conditions (FIG. 20B, lane 3) shows the presence of only the three expected polypeptide chains: the AD2-fused heavy chain (HC-AD2), the DDD2-fused Fd chain (Fd-DDD2), and the kappa chains.

Example 29

Generation of Hex-hLL2

The DNL method was used to create a monospecific anti-CD22 HIDS (Hex-hLL2) by combining C-H-AD2-hLL2 IgG (see Example 25) with hLL2-Fab-DDD2. The DNL reaction was accomplished as described for Hex-hA20 in Example 28.

Figure 21:
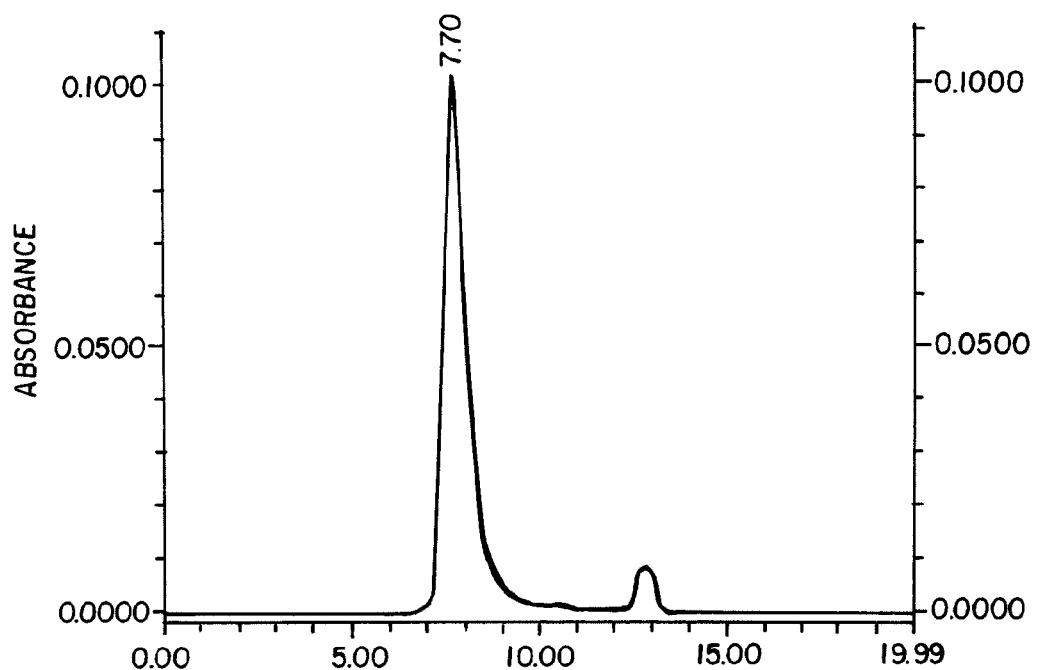
FIG. 21 shows SE-HPLC analysis of Protein A-purified Hex-hLL2.

The calculated molecular weight from the deduced amino acid sequences of the constituent polypeptides is 386 kDa. Size exclusion HPLC analysis showed a single protein peak with a retention time consistent with a protein structure of 375-400 kDa (FIG. 21). SDS-PAGE analysis under non-reducing conditions shows a cluster of high molecular weight bands indicating a large covalent structure (FIG. 20A, lane 4). SDS-PAGE under reducing conditions (FIG. 20B, lane 4) shows the presence of only the three expected polypeptide chains: HC-AD2, Fd-DDD2, and the kappa chain.

Example 30

Generation of DNL1 and DNL1C

The DNL method was used to create bispecific HIDS by combining C-H-AD2-hLL2 IgG (see Example 25) with either hA20-Fab-DDD2 to obtain DNL1 or hMN-14-DDD2 to obtain DNL1C. DNL1 has four binding arms for CD20 and two for CD22. As hMN-14 is a humanized MAb to carcinoembryonic antigen (CEA), DNL1C has four binding arms for CEA and two for CD22. The DNL reactions were accomplished as described for Hex-hA20 in Example 28.

Figure 22A:
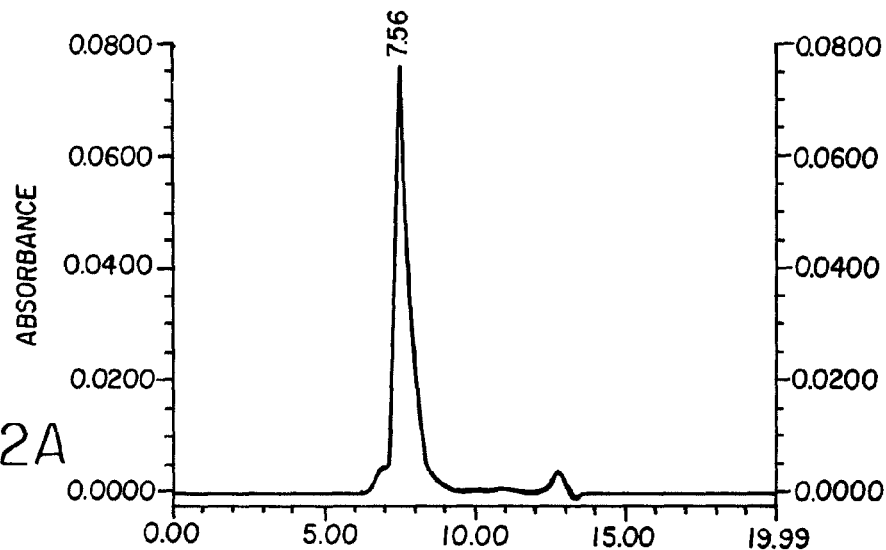
FIG. 22 shows SE-HPLC analysis of (A) DNL1 and (B) DNL1C.
Figure 22B:
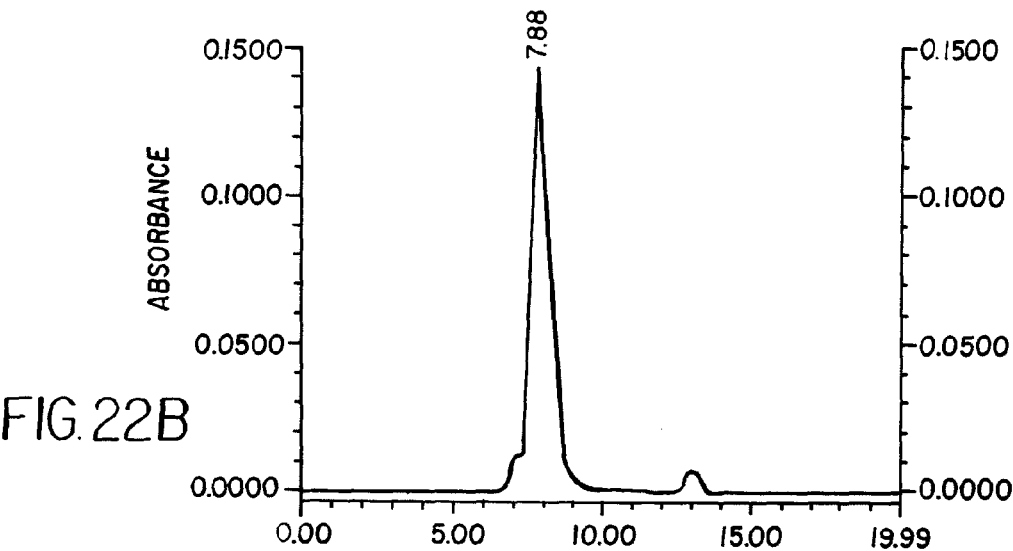

For both DNL1 and DNL1C, the calculated molecular weights from the deduced amino acid sequences of the constituent polypeptides are ~386 kDa. Size exclusion HPLC analysis showed a single protein peak with a retention time consistent with a protein structure of 375-400 kDa for each structure (DNL1 in FIG. 22A and DNL1C in FIG. 22B). SDS-PAGE analysis under non-reducing conditions shows a cluster of high molecular weight bands indicating a large covalent structure (FIG. 20A, lanes 1 & 5). SDS-PAGE under reducing conditions (FIG. 20B, lanes 1 & 5) shows that the large covalent structures are composed solely of the three expected polypeptides: HC-AD2, Fd-DDD2, and the kappa chain.

Example 31

Generation of DNL2 and DNL2C

The DNL method was used to create bispecific HIDS by combining C-H-AD2-hA20 IgG (see Example 26) with either hLL2-Fab-DDD2 to obtain DNL2 or hMN-14-DDD2 to obtain DNL2C. DNL2 has four binding arms for CD22 and two for CD20. DNL2C has four binding arms for CEA and two for CD20. The DNL reactions were accomplished as described for Hex-hA20 in Example 28.

Figure 23:
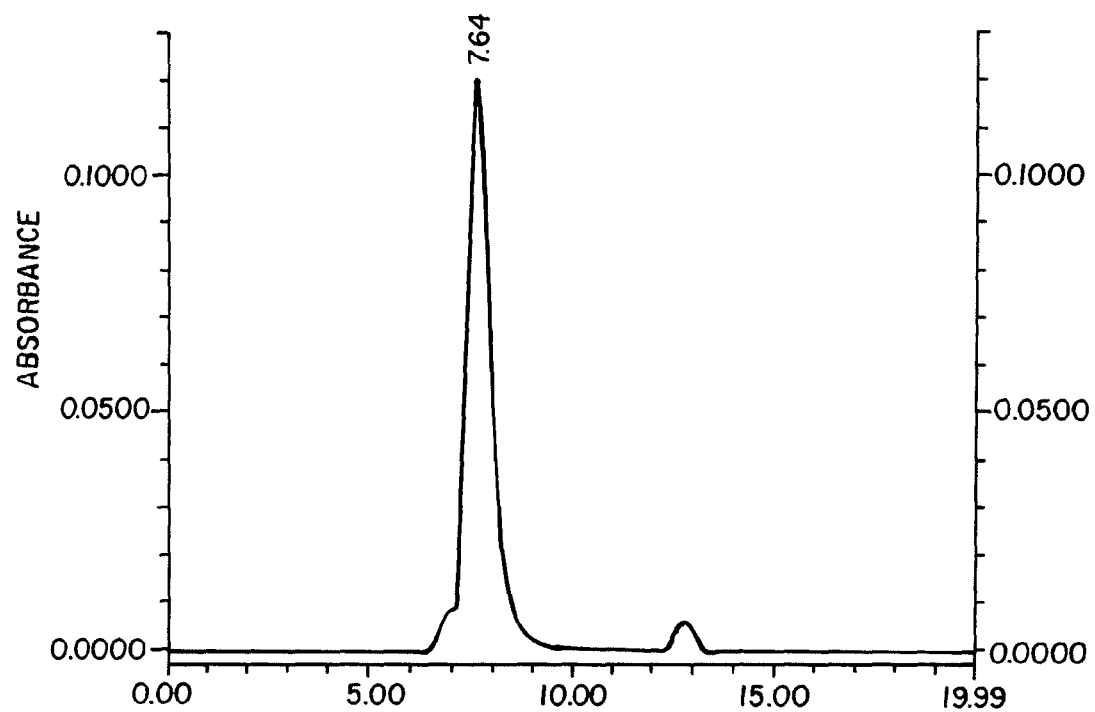
FIG. 23 shows SE-HPLC analysis of DNL2.

For both DNL2 and DNL2C, the calculated molecular weights from the deduced amino acid sequences of the constituent polypeptides are ~386 kDa. Size exclusion HPLC analysis showed a single protein peak with a retention time consistent with a protein structure of 375-400 kDa for each structure (FIG. 23). SDS-PAGE analysis under non-reducing conditions shows a cluster of high molecular weight bands indicating a large covalent structure (FIG. 20A, lanes 2 & 6). SDS-PAGE under reducing conditions (FIG. 20B, lanes 2 & 6) shows that the large covalent structures are composed solely of the three expected polypeptides: HC-AD2, Fd-DDD2, and the kappa chain.

Example 32

Generation of K-Hex-hA20

The DNL method was used to create a monospecific anti-CD20 HIDS (K-Hex-hA20) by combining N-L-AD2-hA20 IgG (see Example 27) with hA20-Fab-DDD2. The DNL reaction was accomplished as described for Hex-hA20 in Example 28.

Figure 24:
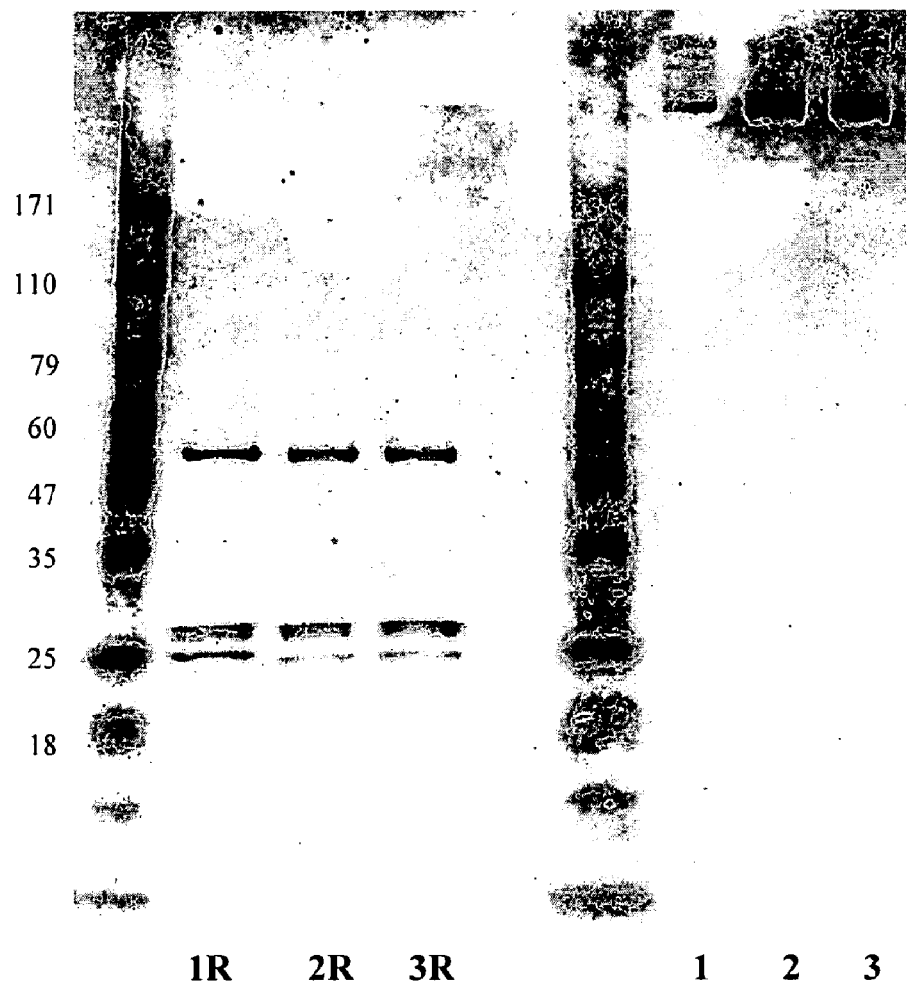
FIG. 24 shows SDS-PAGE analysis of DNL3 and K-Hex-hA20 under reducing and non-reducing conditions. Bands representing heavy chain, AD2-kappa chain, Fd-DDD2 and kappa light chain are shown in the reduced lanes. Bands representing DNL3 and K-Hex-hA20 are shown in the non-reduced lanes. The positions of molecular weight markers are indicated.

The calculated molecular weight from the deduced amino acid sequences of the constituent polypeptides is 386 kDa. SDS-PAGE analysis under non-reducing conditions shows a cluster of high molecular weight bands indicating a large covalent structure (FIG. 24, lanes 2 & 3). SDS-PAGE under reducing conditions (FIG. 24, lane 2R & 3R) shows that the large covalent structure is composed solely of the four expected polypeptides: Fd-DDD2, H-chain, kappa chain, and AD2-kappa.

Example 33

Generation of DNL3

A bispecific HIDS was generated by combining N-L-AD2-hA20 IgG (see Example 27) with hLL2-Fab-DDD2. The DNL reaction was accomplished as described for Hex-hA20 in Example 28.

Figure 25:
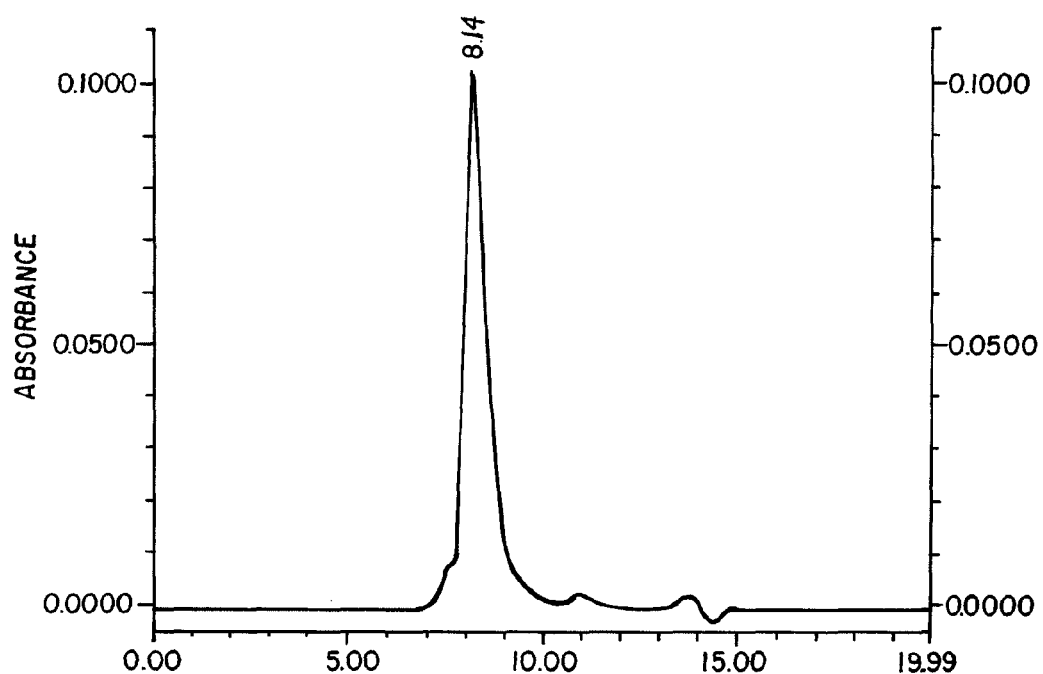
FIG. 25 shows SE-HPLC analysis of DNL3.

The calculated molecular weight from the deduced amino acid sequences of the constituent polypeptides is 386 kDa. Size exclusion HPLC analysis showed a single protein peak with a retention time consistent with a protein structure of 375-400 kDa (FIG. 25). SDS-PAGE analysis under non-reducing conditions shows a cluster of high molecular weight bands indicating a large covalent structure (FIG. 24, lane 1). SDS-PAGE under reducing conditions (FIG. 24, lane 1) shows that the large covalent structure is composed solely of the four expected polypeptides: Fd-DDD2, H-chain, kappa chain, and AD2-kappa.

Example 34

In Vitro Characterization of HIDS

Figure 26:
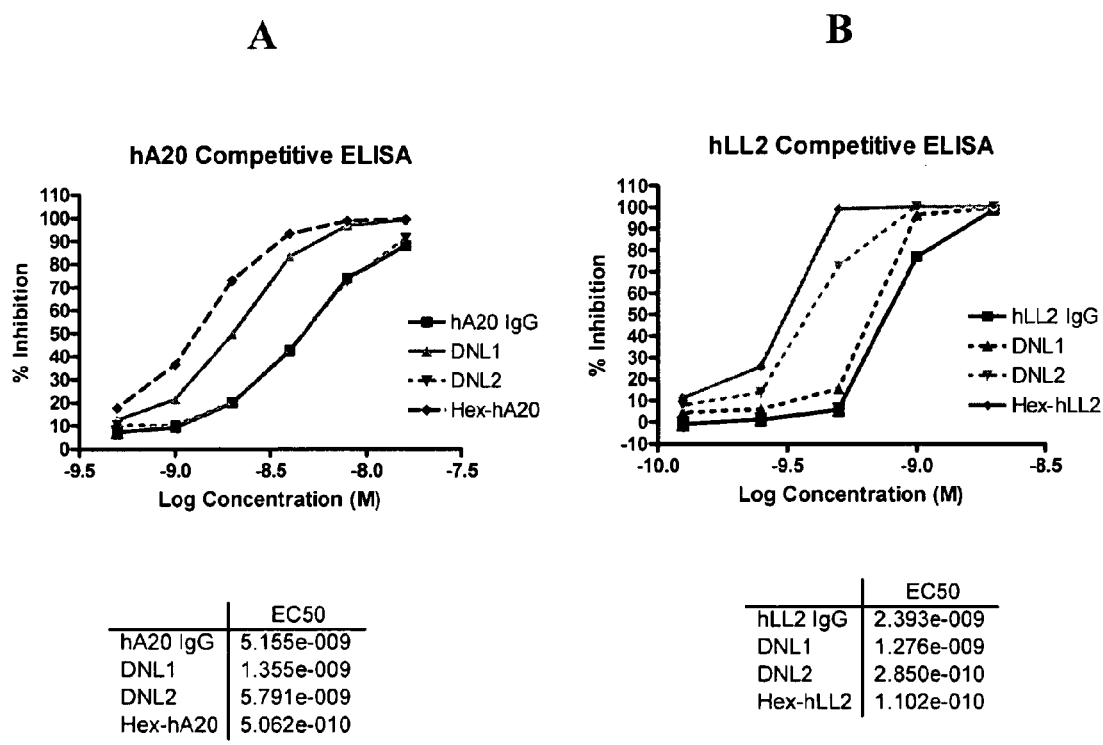
FIG. 26 shows the results of two competitive ELISA experiments to compare the relative hA20/hLL2 binding avidities of DNL1, DNL2 Hex-hA20 and Hex-hLL2 with the parental IgGs. Microtitre plates were coated with hA20 or hLL2 IgG at 5 µg/ml. Dilution series of the HIDS were mixed with anti-Ids specific to hA20 or hLL2 IgG, which was maintained at a constant concentration (2 nM). The level of binding of the anti-Ids to the coated wells was detected using peroxidase-conjugated-Goat anti-Rat IgG and OPD substrate solution. The results are plotted as % inhibition (of anti-Id binding to coated wells) vs. concentration of HIDS. $EC_{50}$ (the effective concentration resulting in 50% inhibition) values were durived using Prism software. The HIDS were used to compete for binding to (A) WI2 (hA20 Rat anti-Id) in hA20-coated wells or (B) WN (hLL2 Rat anti-Id) in hLL2-coated wells.
Figure 27:
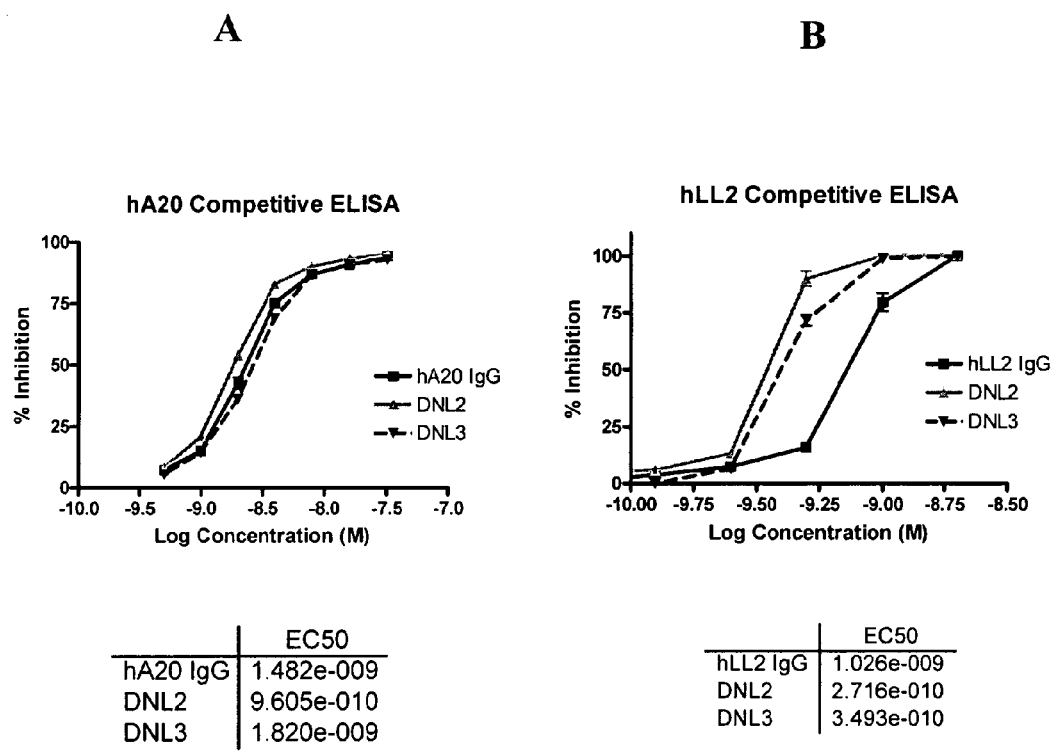
FIG. 27 shows the results of two competitive ELISA experiments to compare the relative hA20/hLL2 binding avidities of DNL2 and DNL3. Experiments were carried out as described for FIG. 26. DNL2, DNL3 and the parental IgGs were used to compete for binding to (A) WI2 (hA20 Rat anti-Id) in hA20-coated wells or (B) WN (hLL2 Rat anti-Id) in hLL2-coated wells.

As shown in FIGS. 26 and 27, the HIDS generated as described in Examples 28-33 retain the binding properties of their parental Fab/IgGs. Competitive ELISAs were used to investigate the binding avidities of the various HIDS using either a rat anti-idiotype MAb to hA20 (WR2) to assess the binding activity of the hA20 components or a rat anti-idiotype MAb to hLL2 (WN) to assess the binding activity of the hLL2 components. To assess hA20 binding, ELISA plates were coated with hA20 IgG and the HIDS were allowed to compete with the immobilized IgG for WR2 binding. To assess hLL2 binding, plates were coated with hLL2 IgG and the HIDS were allowed to compete with the immobilized IgG for WN binding. The relative amount of anti-Id bound to the immobilized IgG was detected using peroxidase-conjugated anti-Rat IgG.

The relative CD20 binding avidities are shown in FIG. 26A. DNL2, which has two CD20 binding groups, showed a similar binding avidity to hA20 IgG, which also has two CD20-binding arms. DNL1, which has four CD20-binding groups, had a stronger (~4-fold) relative avidity than DNL2 or hA20 IgG. Hex-hA20, which has six CD20-binding groups, had an even stronger (~10-fold) relative avidity than hA20 IgG.

Similar findings are shown for CD22 binding in FIG. 26B. DNL1, which has two CD20 binding groups, showed a similar binding avidity to hLL2 IgG, which also has two CD22-binding arms. DNL2, which has four CD22-binding groups, had a stronger (>5-fold) relative avidity than DNL1 or hLL2 IgG. Hex-hLL2, which has six CD22-binding groups, had an even stronger (>10-fold) relative avidity than hLL2 IgG.

As both DNL2 and DNL3 contain two hA20 Fabs and four hLL2 Fabs, they show similar strength in binding to the same anti-id antibody (FIG. 27).

Figure 28:
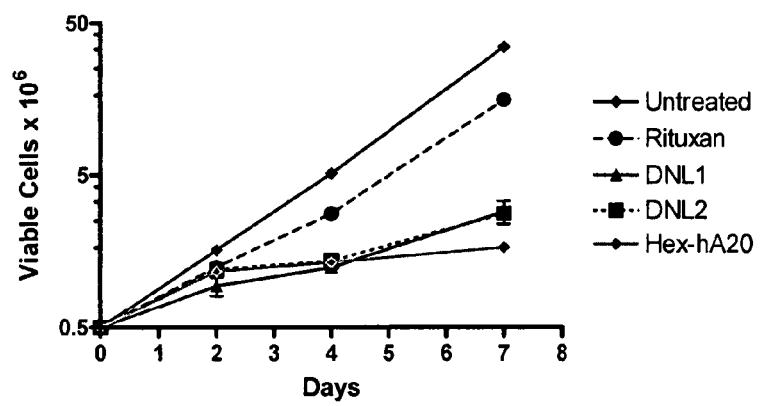
FIG. 28 shows the result of cell counting assays following treatment of Daudi lymphoma cells with DNL1, DNL2, Hex-hA20 or rituximab. Tissue culture flasks were inoculated with $1\times10^5$ Daudi cells/ml in RPMI 1640 media supplemented with one of the HIDS or rituximab at varying concentrations. Viable cells were counted daily using a Guava PCA. (A) Comparison growth curves following treatments at 10 nM concentrations. (B) Comparison of growth curves at selected concentrations.
Figure 28:
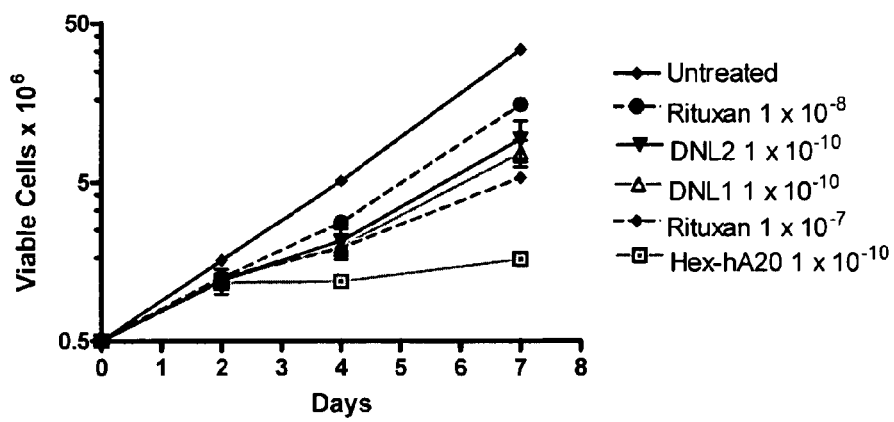
Figure 29:
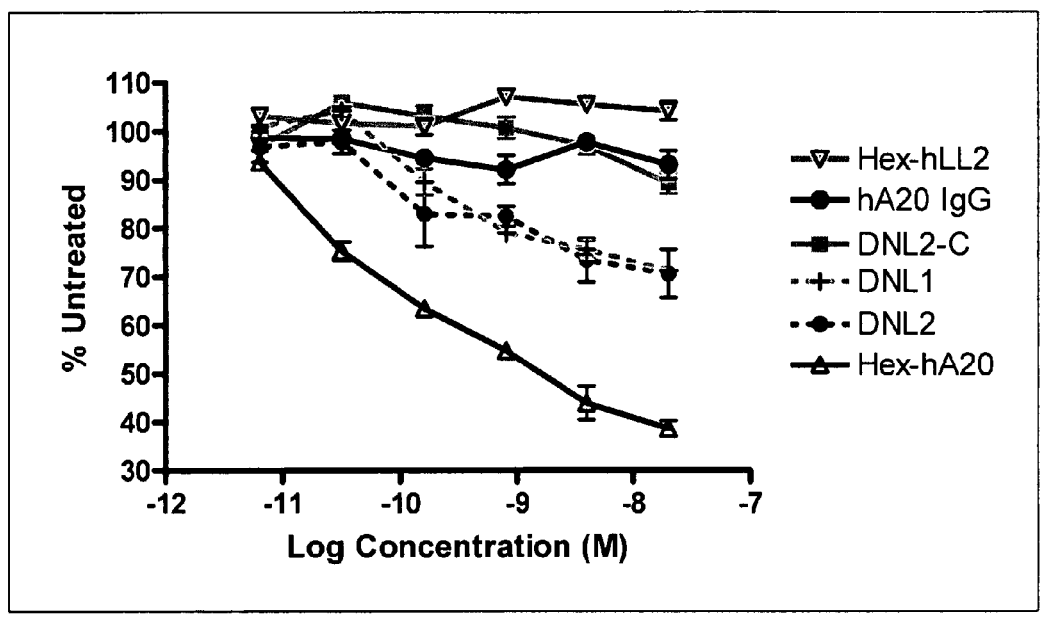
FIG. 29 shows the results of a dose-response experiment for treatment of Daudi cells with various HIDS. Cells were plated in 96-well plates at 5,000 cells/well in RPMI 1640 media. Five-fold serial dilutions were performed in triplicate from concentrations of $2\times10^{-8}$ down to $6.4\times10^{-12}$ M. The plates were incubated for four days, after which MTS reagent was added and the incubation was continued for an additional four hours before reading the plates at 490 nm. The results are given as percent of the $OD_{490}$ for untreated wells vs. the log of the molar concentration of HIDS. $EC_{40}$ (the effective concentration resulting in 40% growth inhibition) values were measured for each dose-response curve.

Some of the HIDS were shown to have potent anti-proliferative activity on lymphoma cell lines. DNL1, DNL2 and Hex-hA20 inhibited cell growth of Daudi Burkitt Lymphoma cells in vitro (FIG. 28). Treatment of the cells with 10 nM concentrations was substantially more effective for the HIDS compared to rituximab (FIG. 28A). Using a cell counting assay, the potency of DNL1 and DNL2 was estimated to be more than 100-fold greater than that of rituximab, while the Hex-hA20 was shown to be even more potent (FIG. 28B). This was confirmed with an MTS proliferation assay in which dose-response curves were generated for Daudi cells treated with a range of concentrations of the HIDS (FIG. 29). Compared to rituximab, the bispecific HIDS (DNL1 and DNL2) and Hex-hA20 were >100-fold and >10000-fold more potent, respectively.

Example 35

In Vivo Anti-Tumor Activity of HIDS

Figure 30:
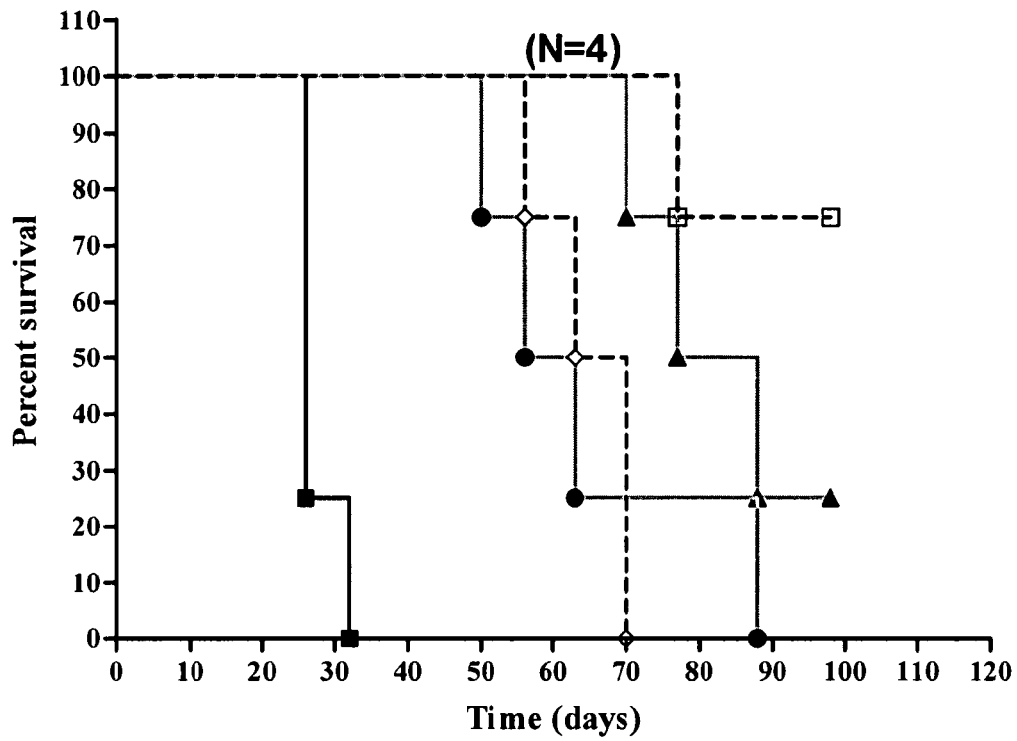
FIG. 30 shows the results of an in vivo therapy experiment where mice bearing human Burkitt Lymphoma (Daudi) were treated with DNL2 or Hex-hA20. Mice (4/group) were inoculated i.v. with $1.5\times10^7$ Daudi cells (day 0). On days 1, 4 and 7, mice were administered either 4 µg or 20 µg of DNL2 or Hex-hA20 intraperitoneally (i.p.). Mice were sacrificed if they developed either hind-limb paralysis or lost >20% body weight. The results are plotted as % survival vs. time (days). Median survival and long term survivors are shown.

The HIDS were shown to have therapeutic efficacy in vivo using a human Burkitt Lymphoma model in mice (FIG. 30). Low doses (12 µg) of DNL2 and Hex-hA20 more than doubled the survival times of tumor bearing mice. Treatment with higher doses (60 µg) resulted in long-term survivors.

Example 36

Comparative Effects of HIDS and Parent IgG on Lymphoma Cell Lines

Figure 31:
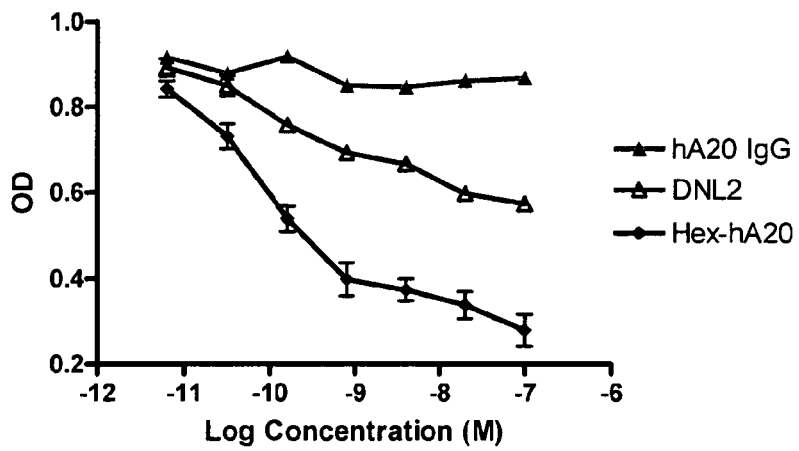
FIG. 31 shows the relative dose-response curves generated using an MTS proliferation assay for Daudi cells, Raji cells and Ramos cells treated with a bispecific HID (DNL2-four hLL2 Fab fragments tethered to an hA20 IgG) and a monospecific HID (Hex-hA20), compared with an hA20 IgG control. In Daudi cells (top panel), DNL2 showed >100-fold and Hex-hA20 showed >10,000 fold more potent antiproliferative activity than hA20 IgG. In Raji cells (middle panel), Hex-hA20 displayed potent anti-proliferative activity, while DNL2 showed only minimal activity, compared to hA20 IgG. In Ramos cells (bottom panel), both DNLs and Hex-hA20 displayed potent anti-proliferative activity compared to hA20 IgG.
Figure 31:
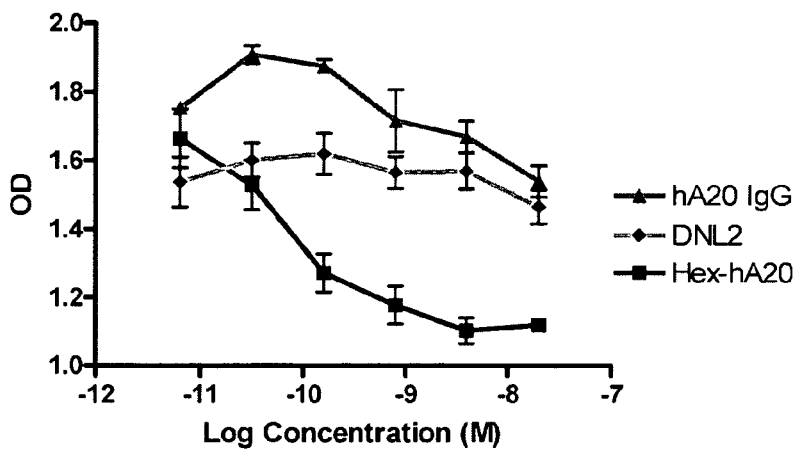
Figure 31:
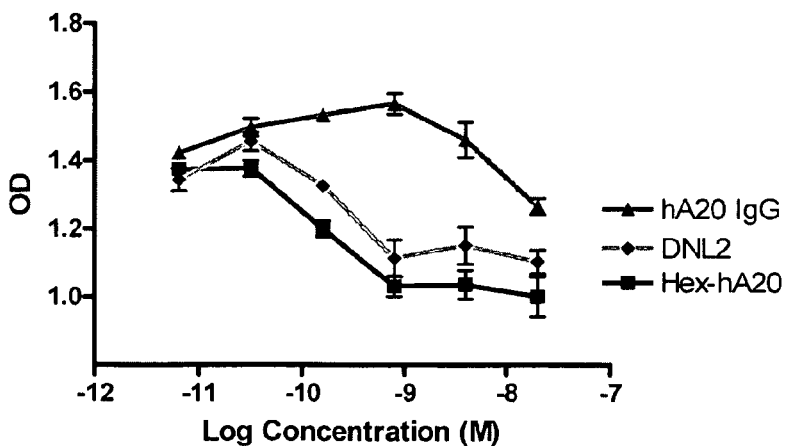

Dose-response curves for HIDS (DNL1, DNL2, Hex-hA20) versus a parent IgG (hA20 IgG) were compared for three different lymphoma cell lines (FIG. 31), using an MTS proliferation assay. In Daudi lymphoma cells (FIG. 31, top panel), the bispecific structures DNL1 (not shown) and DNL2 showed >100-fold more potent anti-proliferative activity and Hex-hA20 showed >10,000-fold more potent activity than the parent hA20 IgG. Hex-hLL2 and the control structures (DNL1-C and DNL2-C) had very little anti-proliferative activity in this assay (not shown).

In Raji lymphoma cells (FIG. 31, middle panel), Hex-hA20 displayed potent anti-proliferative activity, but DNL2 showed only minimal activity compared with hA20 IgG. In Ramos lymphoma cells (FIG. 31, bottom panel), both DNL2 and Hex-hA20 displayed potent anti-proliferative activity, compared with hA20 IgG. These results show that the increased potency of HIDS relative to the parent IgGs is not limited to particular cell lines, but rather is a general phenomenon for cells displaying the appropriate targets.

Example 37

Effects of Cross-Linking on Efficacy of HIDS and Parent IgGs

Figure 32:
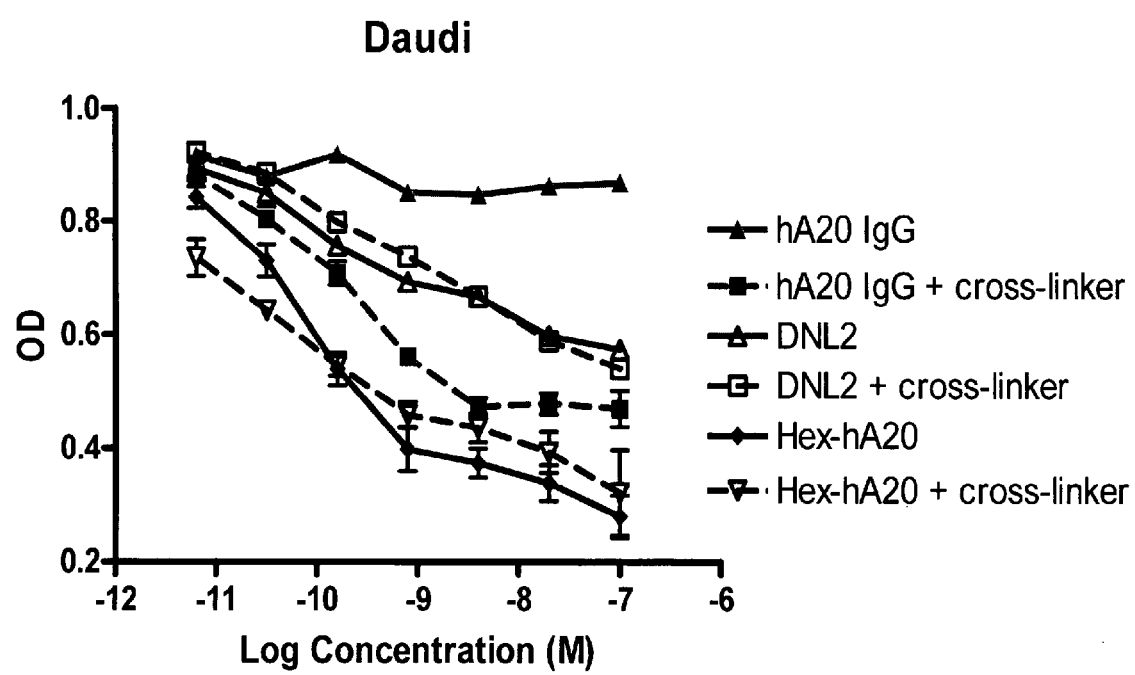
FIG. 32 shows the effects of cross-linking on the anti-proliferative activity of hA20 IgG, DNL2 and Hex-hA20. As shown in the Figure, cross-linking potentiated the anti-proliferative activity of hA20 IgG, but resulted in no enhancement of the activities of DNL2 or Hex-hA20.

Cross-linking of anti-CD20 monoclonal antibodies has been shown to enhance their efficacy in vitro. FIG. 32 shows the effects of cross-linking on the relative efficacies of HIDS versus parent IgG, using an MTS assay. As shown in FIG. 32, this effect was replicated in Daudi lymphoma cells treated with hA20 IgG cross-linked with goat anti-human IgG Fc-specific cross-linker, compared with non-cross-linked hA20 IgG. However, no enhancement of anti-proliferative activity was observed with DNL2 or Hex-hA20 in the presence of cross-linker. As discussed below, it is possible that the Fc portion of the HIDS becomes inaccessible when four additional Fab groups are tethered to its carboxyl termini.

Example 38

Stability in Serum

Figure 33:
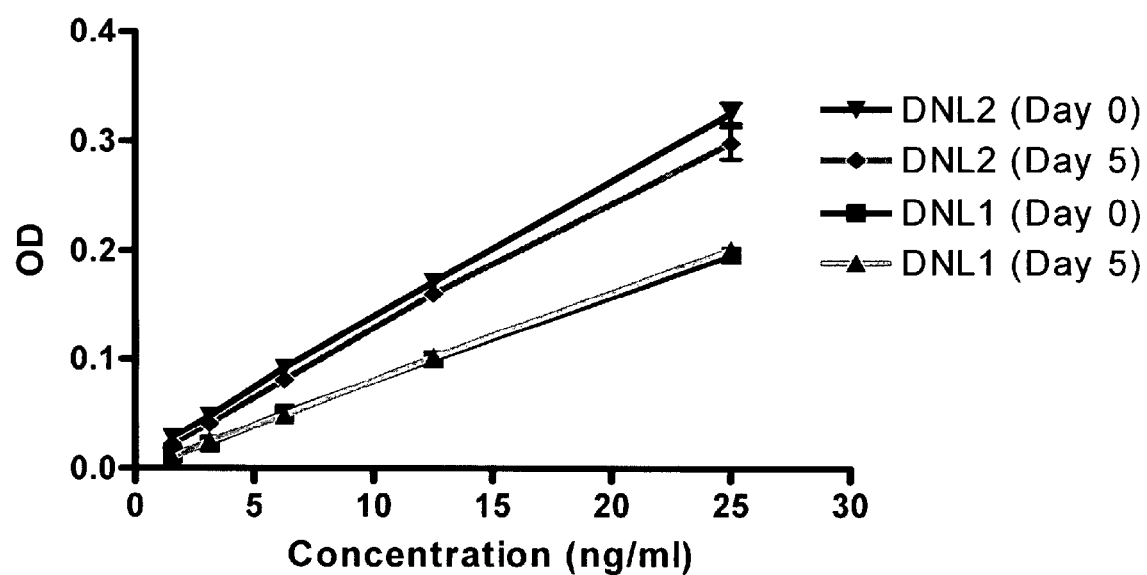
FIG. 33 shows the stability of DNL1 and DNL2 in human serum, as determined using a bispecific ELISA assay. The protein structures were incubated at 10 µg/ml in fresh pooled human sera at 37° C. and 5% $CO_2$ for five days. For day 0 samples, aliquots were frozen in liquid nitrogen immediately after dilution in serum. ELISA plates were coated with an anti-Id to hA20 IgG and bispecific binding was detected with an anti-Id to hLL2 IgG. Both DNL1 and DNL2 were highly stable in serum and maintained complete bispecific binding activity.

FIG. 33 shows the stability of DNL1 and DNL2 in human serum, as determined using a bispecific ELISA assay. The protein structures were incubated at 10 µg/ml in fresh pooled human sera at 37° C. and 5% $CO_2$ for five days. For day 0 samples, aliquots were frozen in liquid nitrogen immediately after dilution in serum. ELISA plates were coated with an anti-Id to hA20 IgG and bispecific binding was detected with an anti-Id to hLL2 IgG. Both DNL1 and DNL2 were highly stable in serum and maintained complete bispecific binding activity.

Example 39

CDC and ADCC Activity

Figure 34:
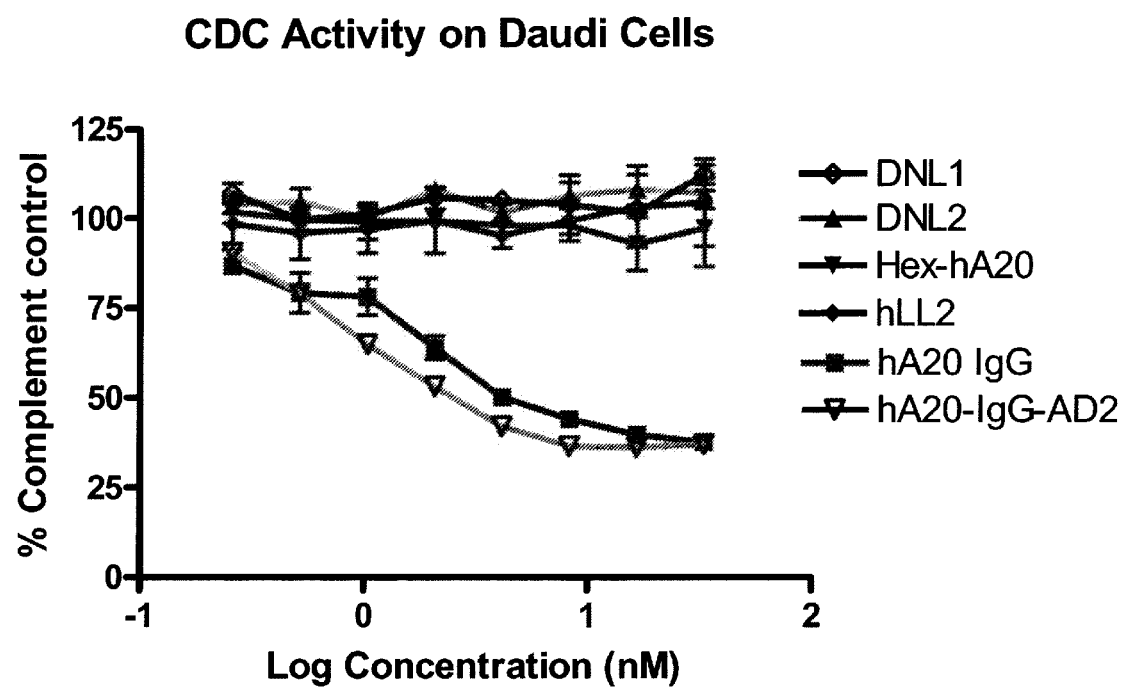
FIG. 34 illustrates the complement-dependent cytotoxicity (CDC) or lack thereof by DNL1, DNL2, Hex-hA20, hLL2, hA20-IgG and hA20-IgG-AD2. Surprisingly, although hA20 IgG and hA20-IgG-AD2 exhibited potent CDC activity on Daudi cells in an in vitro assay, none of the hexavalent DNL structures exhibited CDC activity in this assay. Both DNL2 and Hex-ha20 comprise hA20-IgG-AD2, which showed CDC activity similar to hA20 IgG.

In vivo, anti-CD20 monoclonal antibodies such as rituximab and hA20 can utilize complement-dependent cytotoxicity (CDC), antibody-dependent cellular cytotoxicity (ADCC) and signal transduction induced growth inhibition/apoptosis for tumor cell killing. The hexavalent DNL structures (DNL1, DNL2, Hex-hA20) were tested for CDC activity using Daudi cells in an in vitro assay. Surprisingly, none of the hexavalent structures that bind CD20 exhibited CDC activity (FIG. 34). The parent hA20 IgG exhibited potent CDC activity (FIG. 34), while as expected the hLL2 antibody against CD22 showed no activity. The lack of effect of DNL2 and Hex-hA20 was of interest, since they comprise hA20-IgG-Ad2, which showed similar positive CDC activity to hA20 IgG (FIG. 34).

Figure 35:
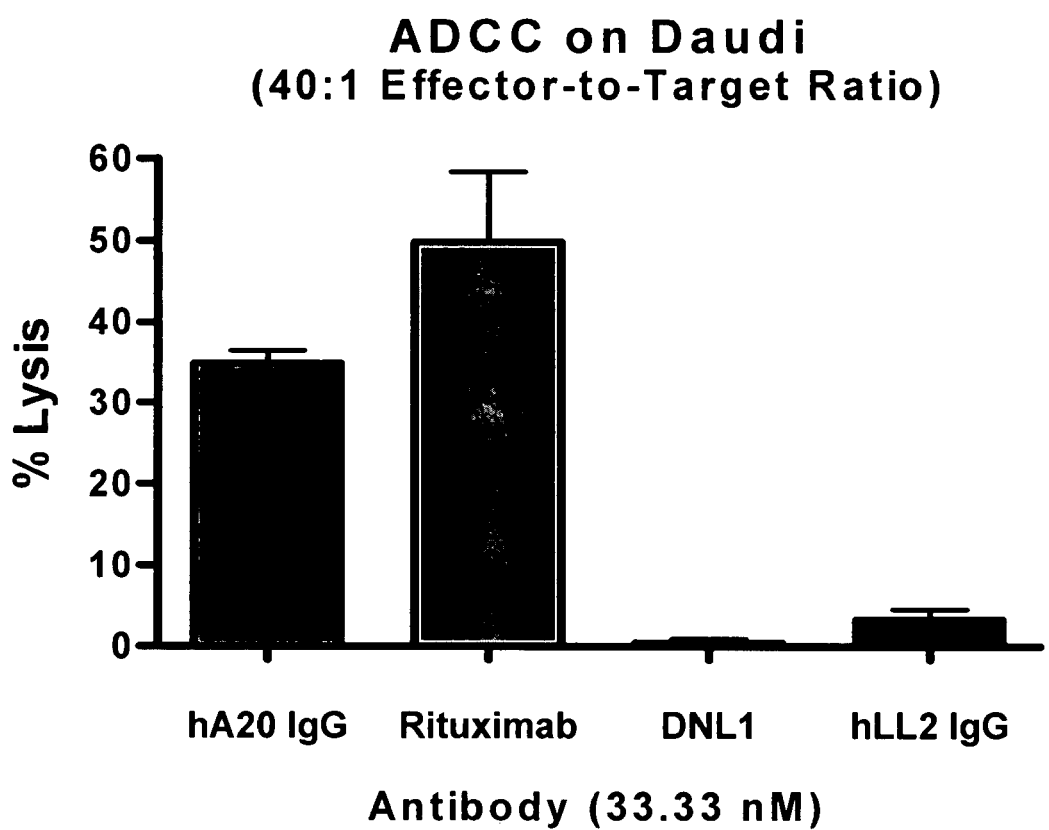
FIG. 35 shows the antibody-dependent cellular cytotoxicity (ADCC) of DNL1, compared with hA20 IgG, Rituximab and hLL2 IgG, assayed with freshly isolated peripheral blood mononuclear cells. Both rituximab and hA20 IgG had potent ADCC activity, while DNL1 did not exhibit any detectable ADCC.

DNL1 was assayed for ADCC activity using freshly isolated peripheral blood mononuclear cells (FIG. 35). Both rituximab and hA20 IgG showed potent activity on Daudi cells (FIG. 35), while DNL1 did not exhibit any detectable ADCC activity.

These data suggest that the Fc region may become inaccessible for effector functions (CDC and ADCC) when four additional Fab groups are tethered to its carboxyl termini. Therefore, the hexavalent DNL structures appear to rely only on signal transduction induced growth inhibition/apoptosis for in vivo anti-tumor activity.

TABLE 1

Tumor Uptake and Tissue Clearance of $^{125}$I-TF2 in LS 174T Tumor-Bearing Nude Mice

| Tissue | % ID/g ± SD | | | | | | |
|---|---|---|---|---|---|---|---|
| | 0.5 h | 2 h | 4 h | 16 h | 24 h | 48 h | 72 h |
| LS 174T | 4.43 ± 1.13 | 9.19 ± 1.18 | 10.33 ± 2.05 | 5.32 ± 1.09 | 5.37 ± 0.72 | 1.69 ± 0.60 | 1.00 ± 0.13 |
| Liver | 11.71 ± 2.22 | 8.39 ± 0.86 | 4.24 ± 0.11 | 0.32 ± 0.02 | 0.26 ± 0.03 | 0.15 ± 0.02 | 0.12 ± 0.01 |
| Spleen | 22.04 ± 6.02 | 24.87 ± 8.22 | 15.39 ± 1.35 | 0.73 ± 0.14 | 0.45 ± 0.06 | 0.25 ± 0.08 | 0.21 ± 0.03 |
| Kidney | 13.45 ± 0.64 | 6.31 ± 0.48 | 3.88 ± 0.24 | 0.31 ± 0.04 | 0.24 ± 0.03 | 0.14 ± 0.02 | 0.11 ± 0.01 |
| Lungs | 9.02 ± 1.38 | 4.99 ± 0.62 | 3.91 ± 0.08 | 0.33 ± 0.06 | 0.23 ± 0.04 | 0.09 ± 0.00 | 0.06 ± 0.01 |
| Blood | 36.17 ± 3.49 | 15.51 ± 2.43 | 9.06 ± 0.93 | 0.68 ± 0.07 | 0.43 ± 0.05 | 0.16 ± 0.04 | 0.11 ± 0.03 |
| Stomach | 3.03 ± 0.45 | 26.00 ± 5.55 | 50.79 ± 10.83 | 0.85 ± 0.10 | 1.08 ± 0.38 | 0.23 ± 0.06 | 0.20 ± 0.03 |
| Sm. Int. | 2.21 ± 0.17 | 3.09 ± 0.50 | 2.08 ± 0.11 | 0.19 ± 0.03 | 0.18 ± 0.04 | 0.06 ± 0.01 | 0.05 ± 0.01 |
| Lg. Int. | 0.83 ± 0.03 | 1.38 ± 0.12 | 1.62 ± 0.07 | 0.21 ± 0.04 | 0.25 ± 0.05 | 0.07 ± 0.01 | 0.09 ± 0.03 |
| Tail | 3.83 ± 0.16 | 3.64 ± 0.95 | 2.79 ± 0.38 | 0.19 ± 0.02 | 0.18 ± 0.05 | 0.09 ± 0.02 | 0.06 ± 0.01 |
| Tumor wt (g) | 0.154 ± 0.040 | 0.098 ± 0.055 | 0.114 ± 0.061 | 0.175 ± 0.061 | 0.159 ± 0.014 | 0.240 ± .150 | 0.468 ± 0.220 |

TABLE 2

Blood pharmacokinetics of TF2 in LS174T tumor bearing mice

| $t_{1/2}\alpha$ (h) | $t_{1/2}\beta$ (h) | Cmax (ng) | CL (ng/h * ng) |
|---|---|---|---|
| 0.58 ± 0.08 | 3.47 ± 0.36 | 31,186 ± 995 | 0.51 ± 0.02 |

TABLE 3

Tumor Uptake and Tissue Clearance of TF2 in LS 174T Tumor-Bearing Nude Mice

| | % ID/g ± SD | | | |
|---|---|---|---|---|
| | Time post-TF2 | | | |
| | 16.5 h | 17 h | 20 h | 40 h |
| | Time post-IMP245 | | | |
| | 0.5 h | 1 h | 4 h | 24 h |
| LS 174T | 6.7 ± 1.6 | 9.0 ± 4.9 | 6.5 ± 1.5 | 3.5 ± 0.8 |
| Liver | 0.29 ± 0.03 | 0.35 ± 0.05 | 0.27 ± 0.02 | 0.14 ± 0.02 |
| Spleen | 0.49 ± 0.12 | 0.53 ± 0.10 | 0.46 ± 0.08 | 0.22 ± 0.06 |
| Kidney | 0.48 ± 0.11 | 0.45 ± 0.14 | 0.29 ± 0.06 | 0.14 ± 0.01 |
| Lungs | 0.31 ± 0.04 | 0.37 ± 0.09 | 0.24 ± 0.06 | 0.12 ± 0.03 |
| Blood | 0.53 ± 0.05 | 0.61 ± 0.16 | 0.44 ± 0.11 | 0.20 ± 0.04 |
| Stomach | 1.05 ± 0.13 | 1.78 ± 0.64 | 0.88 ± 0.47 | 0.50 ± 0.40 |
| Sm. Int. | 0.20 ± 0.02 | 0.27 ± 0.09 | 0.13 ± 0.03 | 0.08 ± 0.03 |
| Lg. Int. | 0.30 ± 0.10 | 0.47 ± 0.17 | 0.20 ± 0.06 | 0.10 ± 0.05 |
| Tail | 0.41 ± 0.13 | 0.26 ± 0.06 | 0.22 ± 0.15 | 0.09 ± 0.01 |
| Tumor wt (g) | 0.279 ± 0.142 | 0.222 ± 0.113 | 0.362 ± 0.232 | 0.356 ± 0.152 |

TABLE 4

Tumor Uptake and Tissue Clearance of $^{99m}$Tc-IMP-245 pretargeted with TF2 in LS 174T Tumor-Bearing Nude Mice

| | % ID/g ± SD | | | |
|---|---|---|---|---|
| | Time post-TF2 | | | |
| | 16.5 h | 17 h | 20 h | 40 h |
| | Time post-IMP245 | | | |
| | 0.5 h | 1 h | 4 h | 24 h |
| LS 174T | 21.8 ± 3.0 | 30.1 ± 13.7 | 25.0 ± 3.7 | 16.3 ± 2.9 |
| Liver | 0.64 ± 0.07 | 0.41 ± 0.06 | 0.23 ± 0.06 | 0.14 ± 0.02 |
| Spleen | 0.59 ± 0.07 | 0.30 ± 0.06 | 0.16 ± 0.08 | 0.09 ± 0.02 |
| Kidney | 8.7 ± 1.4 | 5.0 ± 0.4 | 2.4 ± 0.4 | 1.2 ± 0.2 |
| Lungs | 1.6 ± 0.2 | 0.69 ± 0.16 | 0.24 ± 0.05 | 0.10 ± 0.03 |
| Blood | 1.7 ± 0.2 | 0.50 ± 0.12 | 0.11 ± 0.02 | 0.04 ± 0.01 |
| Stomach | 0.37 ± 0.09 | 0.87 ± 1.28 | 0.09 ± 0.08 | 0.16 ± 0.09 |
| Sm. Int. | 0.79 ± 0.04 | 1.08 ± 0.22 | 0.25 ± 0.12 | 0.15 ± 0.06 |

TABLE 4-continued

Tumor Uptake and Tissue Clearance of $^{99m}$Tc-IMP-245 pretargeted with TF2 in LS 174T Tumor-Bearing Nude Mice

| | % ID/g ± SD Time post-TF2 | | | |
|---|---|---|---|---|
| | 16.5 h | 17 h | 20 h | 40 h |
| | Time post-IMP245 | | | |
| | 0.5 h | 1 h | 4 h | 24 h |
| Lg. Int. | 0.30 ± 0.09 | 0.13 ± 0.03 | 1.9 ± 2.0 | 0.40 ± 0.28 |
| Tail | 2.1 ± 0.4 | 0.94 ± 0.45 | 0.45 ± 0.49 | 0.06 ± 0.02 |
| Tumor wt (g) | 0.279 ± 0.142 | 0.222 ± 0.113 | 0.362 ± 0.232 | 0.356 ± 0.152 |

TABLE 5

T/NT ratio for the pretargeted $^{99m}$Tc-peptide (IMP-245) using TF2.

| | Time post - IMP245 | | | |
|---|---|---|---|---|
| | 0.5 h | 1 h | 4 h | 24 h |
| Liver | 34 ± 4 | 83 ± 10 | 116 ± 32 | 115 ± 21 |
| Spleen | 37 ± 4 | 109 ± 21 | 170 ± 54 | 177 ± 30 |
| Kidney | 3 ± 0.4 | 7 ± 2 | 11 ± 2 | 14 ± 3 |
| Lungs | 14 ± 2 | 47 ± 4 | 106 ± 26 | 162 ± 24 |
| Blood | 13 ± 2 | 66 ± 5 | 237 ± 36 | 395 ± 26 |
| Stomach | 63 ± 25 | 169 ± 116 | 456 ± 271 | 135 ± 91 |
| Sm. Int. | 28 ± 3 | 35 ± 5 | 114 ± 47 | 125 ± 46 |
| Lg. Int. | 75 ± 17 | 241 ± 31 | 22 ± 14 | 57 ± 34 |
| Tail | 11 ± 3 | 37 ± 8 | 164 ± 135 | 293 ± 80 |

TABLE 6

Examples of Complexes Comprised of Two Types of Antigen-Binding Subunits

| Target of A | Target of B | A | B | Application |
|---|---|---|---|---|
| CEA | HSG | hMN-14 | h679 | pRAIT; cancer imaging/therapy |
| CEA | In-DTPA | hMN-14 | h734 | pRAIT/cancer imaging/therapy |
| ED-B fibronectin | HSG | L19 | h679 | pRAIT/cancer imaging/therapy |
| ED-B fibronectin | In-DTPA | L19 | h734 | pRAIT/cancer imaging/therapy |
| CD20 | CD22 | hA20 | hLL2 | Lymphoma and autoimmune disease (AID) therapies |
| CD22 | CD20 | hLL2 | hA20 | Lymphoma/AID therapies |
| CD19 | CD20 | | | Lymphoma/AID therapies |
| EGFR | IGFR1 | | | Solid tumor therapy |
| VEGFR1/Flt-1 | VEGFR2/KDR | | | Blocking VEGF/PlGF binding; solid tumor and angiogenesis therapies |
| VEGFR3/Flt-4 | VEGFR2/KDR | | | Blocking angiogenesis and solid tumor therapies |
| CD19 | CD3/TCR | | | Lymphoma/AID therapies |
| CD19 | CD16/FcγRIIIa | | | Lymphoma/AID therapies |
| CD19 | CD64/FcγRI | | | Lymphoma/AID therapies |
| HER2/neu | CD89/FcαRI | | | Breast cancer therapy |
| HER2/neu | CD16 | | | Breast cancer therapy |
| HER2/neu | CD64 | | | Breast cancer therapy |
| HER2/neu | CD3 | | | breast cancer therapy |
| CD30 | CD64 | | | Lymphoma therapy |
| CD33 | CD64 | | | Acute myeloid leukemia (AML) therapy |
| EGFR | CD2 | | | Solid tumor therapy |
| EGFR | CD64 | | | Solid tumor therapy |
| EGFR | CD16 | | | Solid tumor therapy |
| EGFR | CD89 | | | Solid tumor therapy |
| PfMSP-1 | CD3 | | | Malaria therapy |
| HN | CD3 | HN1,4 c | OKT3 | Tumor vaccine enhancer |
| HN | CD28 | HN1,4 c | 15E8 | Tumor vaccine enhancer |
| EpCAM/17-1A | CD3 | | | Solid tumor therapy |
| IL-2R/Tac | CD3 | | | Lymphoma/AID therapies |
| CA19-9 | CD16 | | | Solid tumor therapy |
| MUC1 | CD64 | | | Solid tumor therapy |
| HLA class II | CD64 | | L243 | Cancer therapy |
| $G_{D2}$ | CD64 | | | Neuroblastoma therapy |
| G250 | CD89 | | | Renal cell carcinoma therapy |
| TAG-72 | CD89 | | hCC49 | Solid tumor therapy |
| EpCAM | Adenovirus fiber knob | | | Retargeting viral vector-solid tumor therapy |

TABLE 6-continued

Examples of Complexes Comprised of Two Types of Antigen-Binding Subunits

| Target of A | Target of B | A | B | Application |
|---|---|---|---|---|
| PSMA | Adenovirus fiber knob | | | Prostate cancer therapy |
| CEA | Adenovirus fiber knob | | S11 | CEA-positive cancer therapy |
| HMWMAA | Adenovirus fiber knob | | | Melanoma therapy |
| G250 | Adenovirus fiber knob | | | Renal cell carcinoma therapy |
| CD40 | Adenovirus fiber knob | | S11 | Immune disease and cancer therapies |
| M13 coat protein | Alkaline phosphatase | | | Viral detection |
| GpIIb/IIIa | tPA | 7E3 | P4B6 | Enhancing thrombolysis |

TABLE 7

Examples of Complexes Comprised of One Type of Antigen-Binding and One Type of Effector Subunit

| Target of A | A | B | Application |
|---|---|---|---|
| CD74 | hLL1 | Rap (N69Q) | CD74+ Cancer/AID therapies |
| CD22 | hLL2 | Rap (N69Q) | Lymphoma and autoimmune disease (AID) therapies |
| MUC1 | hPAM4 | Rap (N69Q) | Pancreatic cancer therapy |
| EGP-1 | hRS7 | Rap (N69Q) | Solid cancer therapy |
| IGF1R | hR1 | Rap (N69Q) | Solid tumor therapy |
| CD22 | HLL2/RFB4 | PE38 | Lymphoma therapy |
| CD30 | | PE38 | Lymphoma therapy |
| CD25/Tac | | PE38 | Lymphoma therapy |
| Le$^Y$ | | PE38 | Solid tumor therapy |
| Mesothelin | | PE38 | Solid tumor therapy |
| Erb-B2 | | PE38 | Breast cancer |
| EpCAM | | PE38 | Solid tumor therapy |
| CD25 | | dgA | Lymphoma therapy |
| CD30 | | dgA | Lymphoma therapy |
| CD19 | | dgA | Lymphoma therapy |
| CD22 | | dgA | Lymphoma therapy |
| CD3 | | DT390 | Graft-versus host disease |
| CD25 | | PLC | Lymphoma therapy |
| Gp240 | | Gelonin | Melanoma therapy |
| X | Anti-X | Straptavidin | ELISA |
| X | Anti-X | HRP | ELISA |
| X | Anti-X | AP | ELISA |
| X | Anti-X | GFP | Reporter protein |
| GpIIb/IIIa | 7E3 | tPA | Enhancing thrombolysis |
| X | Anti-X | Cytokine | Retargeting a cytokine |
| X | Anti-X | Growth factor | Retargeting a growth factor |
| X | Anti-X | Soluble receptor component | Retargeting a receptor |
| X | Anti-X | Carboxypeptidase G2 (CPG2) | Prodrug therapy |
| X | Anti-X | penicillinamidase | Prodrug therapy |
| X | Anti-X | β-lactamase | Prodrug therapy |
| X | Anti-X | Cytosine deaminase | Prodrug therapy |
| X | Anti-X | Nitroreductase | Prodrug therapy |
| p97 | L49 | E. coli beta-galactosidase | Prodrug therapy |
| X | Anti-X | Human carboxyesterase 2 | Solid cancer therapy |

TABLE 8

Examples of Complexes with Two Different Types of Effector Subunits

| Target of A | Target of B | A | B | Application |
|---|---|---|---|---|
| IL-4R | — | IL-4 | PE38 | Solid tumor therapy |
| — | IL-4R | PE38 | IL-4 | Solid tumor therapy |
| IL-4 | IL-13 | sIL-4R | sIL-13R | Asthma, allergy therapy |
| IL-13 | IL-4 | sIL-13R | sIL-4R | Asthma, allergy therapy |
| VEGFR-2 | — | VEGF$_{121}$ | Shiga-like toxin | Cancer therapy |
| VEGFR-2 | | VEGF$_{121}$ | Diptheria toxin | Cancer therapy |
| ED-B fibronectin | | | ILGF-1 | Cancer therapy |

TABLE 9

Examples of Complexes With One Type of Antigen-Binding Subunit

| Target of A | A | Application |
|---|---|---|
| X | Anti-X | Treating or detecting a disease bearing the X marker |
| CD14 | Anti-CD14 | Treating septic shock |
| CD111/nectin-1 | Anti-CD111 | Treating herpesvirus infection |
| Folate receptor α | | Treating filovirus infection (e.g. Ebola and Marburg viruses) |
| Gp120 | | Treating HIV-1/AIDS |
| IL-6 | | Treating myeloma, arthritis and other autoimmune disease |
| IL-5 | | Treating asthma |
| IL-8 | | Treating general infection |
| CD154 | | Treating lupus, transplant rejection, AID |
| IgE | | Treating asthma |
| LFA-1 | | Treating transplant rejection |
| β-tryptase | | Treating allergy, inflammation |
| CD105/endoglin | | Anti-angiogenesis |
| GpIIb/IIa | 7E3 | Thrombolysis |
| TNFα | (Humira) | AID therapy |
| TNFα | (remicade) | AID therapy |
| IgE | (Xolair) | Asthma therapy |
| RSV F-protein | (Synagis) | RSV therapy |
| A1B1 of CEA | hMN-15 | Inhibiting adhesion/invasion/metastasis of solid cancers |
| N domain of CEA | hMN-15 | Inhibiting adhesion/invasion/metastasis of solid cancers |

TABLE 10

Examples of Complexes with One Type of Effector Subunit

| Target of A | A | Application |
|---|---|---|
| Cytokine receptor | Cytokine | Enhancing cytokine function |
| Growth factor receptor | Growth factor | Enhancing growth factor function |
| Membrane bound receptor | Soluble receptor components | Enhancing the capacity and avidity of a soluble receptor component |
| Blood clot | tPA | Enhancing the efficacy of tPA |
| TPO receptor | TPO | Enhancing the efficacy of Thrombopoietin |
| EPO receptor | EPO | Enhancing the efficacy of rHuEPO |
| TNFα | sTNFα-R | Enhancing the efficacy of Enbrel |

What is claimed is:

1. A method of treating B-cell leukemia or B-cell lymphoma comprising administering to a subject with cancer a hexavalent stably tethered structure comprising:
   (i) an IgG antibody that binds to a tumor-associated antigen (TAA), wherein the IgG antibody attached to two AD moieties selected from the group of SEQ ID NO: 3 and 4; and (ii) four antigen-binding antibody fragments of the same or different IgG with each fragment attached to a DDD moiety selected from the group consisting of SEQ ID NO: 1 and SEQ ID NO: 2; the AD moieties bound to the DDD moieties.

2. The method of claim 1, wherein the antigen-binding antibody fragment binds to the same TAA as the IgG.

3. The method of claim 1, wherein the antigen-binding antibody fragment binds to a different TAA from the IgG.

4. The method of claim 1, wherein the AD moieties are covalently attached to the DDD moieties by a disulfide bond.

5. The method of claim 1, wherein the IgG antibody and the antigen-binding antibody fragment are selected from the group consisting of LL1 (anti-CD74), LL2 (anti-CD22), RFB4 (anti-CD22), A20 (anti-CD20), L243 (anti-HLA class II), CC49 (anti-TAG-72), MN-14 (anti-CEA), MN-15 (anti-CEA), 679 (anti-HSG), 734 (anti-In-DTPA), L19 (anti-ED-B fibronectin), R1 (anti-IGF-1R), PAM4 (anti-MUC1), RS7 (anti-EGP-1), adalimumab, infliximab, omalizumab and palivizumab.

6. The method of claim 1, wherein the IgG antibody and the antigen-binding antibody fragment are chimeric, humanized or human.

7. The method of claim 1, wherein the IgG antibody and the antibody fragment are not conjugated to any therapeutic agent.

8. The method of claim 7, further comprising administering at least one therapeutic agent to the subject.

9. The method of claim 8, wherein the therapeutic agent is selected from the group consisting of a chemotherapeutic agent, a cytokine, a chemokine, an anti-angiogenic agent, an apoptotic agent, a drug, a prodrug, a toxin, an enzyme, a radioisotope, an immunomodulator, an antibiotic, and a hormone.

10. The method of claim 1, wherein at least one therapeutic agent is attached to the hexavalent stably tethered structure.

11. The method of claim 10, wherein the therapeutic agent is selected from the group consisting of a chemotherapeutic agent, a cytokine, a chemokine, an anti-angiogenic agent, an apoptotic agent, a drug, a prodrug, a toxin, an enzyme, a radioisotope, an immunomodulator, an antibiotic, and a hormone.

12. The method of claim 1, wherein the cancer is selected from the group consisting of acute lymphoblastic leukemia, acute myelogenous leukemia, chronic lymphocytic leukemia, chronic myelogenous leukemia, Hodgkin's lymphoma, non-Hodgkin's lymphoma, and multiple myeloma.

13. The method of claim 1, further comprising administering a chemotherapeutic agent, a cytokine, radiation therapy, immunotherapy, radioimmunotherapy, localized hyperthermia, laser irradiation, an anti-angiogenic agent or surgical excision in combination with the stably tethered structure.

14. The method of claim 1, wherein the stably tethered structure comprises a combination of IgG antibody and antigen-binding antibody fragment selected from the group consisting of anti-CD74 X anti-CD20, anti-CD74 X anti-CD22, anti-CD22 X anti-CD20, anti-CD20 X anti-HLA-DR, anti-CD19 X anti-CD20, anti-CD20 X anti-CD80, anti-CD2 X anti-CD25, anti-CD8 X anti-CD25, anti-CD2 X anti-CD147, anti-CEACAM5 X anti-CD3, anti-CEACAM6 X anti-CD3, anti-EGFR X anti-CD3, anti-HER2/neu X anti-CD3, anti-CD20 X anti-CD3, anti-CD74 X anti-CD3 and anti-CCD22 X anti-CD3.

15. The method of claim 9, wherein the therapeutic agent is selected from the group consisting of an anthracycline, an epipodophyllotoxin, a taxane, an antimetabolite, an alkylating agent, an antibiotic, a COX-2 inhibitor, an antimitotic, an antiangiogenic agent, a proapoptotic agent, doxorubicin, methotrexate, CPT-11, 5-fluorouracil, bleomycin, busulfan, carboplatin, chlorambucil, cisplatin (CDDP), cyclophosphamide, dactinomycin, daunorubicin, an estrogen receptor binding agent, etoposide (VP16), farnesyl-protein transferase inhibitor, gemcitabine, ifosfamide, mechlorethamine, melphalan, mitomycin, navelbine, nitrosourea, plicamycin, procarbazine, raloxifene, tamoxifen, paclitaxel, temazolomide, transplatinum, vinblastine, vincristine, a camptothecan, a nitrogen mustard, an alkyl sulfonate, a triazene, a folic acid analog, a pyrimidine analog, a purine analog, a platinum coordination complex and a hormone.

16. The method of claim 9, wherein the radioisotope is selected from the group consisting of $^{212}$Pb, $^{212}$Bi, $^{213}$Bi, $^{211}$At, $^{223}$Ra, $^{225}$Ac, $^{32}$P, $^{33}$P, $^{47}$Sc, $^{67}$Cu, $^{67}$Ga, $^{89}$Sr, $^{90}$Y, $^{111}$Ag, $^{125}$I, $^{131}$I, $^{142}$Pr, $^{153}$Sm, $^{161}$Tb, $^{166}$Ho, $^{166}$Dy, $^{177}$L, $^{186}$Re, $^{188}$Re, $^{189}$Re, $^{111}$In, $^{191}$Os, $^{193m}$Pt, $^{195m}$Pt and $^{195m}$Hg.

17. The method of claim 9, wherein the anti-angiogenic agent is selected from the group consisting of angiostatin, baculostatin, canstatin, maspin, an anti-VEGF antibody, an anti-P1GF peptide, an anti-P1GF antibody, an anti-Flk-1 antibody, an anti-Flt-1 antibody an anti-Flt-1 peptide, a laminin peptide, a fibronectin peptide, a plasminogen activator inhibitor, a tissue metalloproteinase inhibitor, interleukin-12, IP-10, Gro-β, thrombospondin, 2-methoxyoestradiol, proliferin-related protein, carboxyamidotriazole, CM101, Marimastat, pentosan polysulphate, angiopoietin-2, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 and minocycline.

18. The method of claim 9, wherein the immunomodulator is selected from the group consisting of a cytokine, a stem cell growth factor, a lymphotoxin, a hematopoietic factor, an interleukin, a colony-stimulating factor, interferon-α, interferon-β, interferon-γ, S1 factor and TNF-alpha.

19. The method of claim 18, wherein the cytokine is selected from the group consisting of human growth hormone, N-methionyl human growth hormone, bovine growth hormone; parathyroid hormone; thyroxine; insulin; proinsulin; relaxin; prorelaxin; follicle stimulating hormone (FSH), thyroid stimulating hormone (TSH), luteinizing hormone (LH); hepatic growth factor; prostaglandin, fibroblast growth factor; prolactin; placental lactogen, OB protein; tumor necrosis factor-α, tumor necrosis factor-β; mullerian-inhibiting substance; mouse gonadotropin-associated peptide; inhibin; activin; vascular endothelial growth factor; integrin; thrombopoietin (TPO); NGF-β; platelet-growth factor; TGF-α, TGF-β; erythropoietin (EPO); macrophage-CSF (M-CSF); granulocyte-macrophage-CSF (GM-CSF); granulocyte-CSF (G-CSF); IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, LIF, FLT-3, angiostatin, thrombospondin, endostatin, and LT.

20. A method of killing cancer cells comprising exposing the cancer cells to a hexavalent stably tethered structure comprising:
(i) an IgG antibody that binds to a tumor-associated antigen (TAA), wherein the IgG antibody attached to two AD moieties selected from the group of SEQ ID NO: 3 and 4; and (ii) four antigen-binding antibody fragments of the same or different IgG with each fragment attached to a DDD moiety selected from the group consisting of SEQ ID NO: 1 and SEQ ID NO: 2; the AD moieties bound to the DDD moieties.

21. The method of claim 20, wherein the antigen-binding antibody fragment binds to the same TAA as the IgG.

22. The method of claim 20, wherein the antigen-binding antibody fragment binds to a different TAA from the IgG.

23. The method of claim 20, wherein the AD moieties are covalently attached to the DDD moieties by a disulfide bond.

24. The method of claim 20, wherein the IgG antibody and the antigen-binding antibody fragment are selected from the group consisting of LL1 (anti-CD74), LL2 (anti-CD22), R1-B4 (anti-CD22), A20 (anti-CD20), L243 (anti-HLA class II), CC49 (anti-TAG-72), MN-14 (anti-CEA), MN-15 (anti-CEA), 679 (anti-HSG), 734 (anti-hi-DTPA), L19 (anti-ED-B fibronectin), R1 (anti-IGF-1R), PAM4 (anti-MUC1), RS7 (anti-EGP-1), adalimumab, infliximab, omalizumab and palivizumab.

25. The method of claim 20, wherein the stably tethered construct is more effective to kill cancer cells than the parent IgG antibody.

* * * * *

SEQUENCE LISTING

```
<160> NUMBER OF SEQ ID NOS: 38

<210> SEQ ID NO 1
<211> LENGTH: 44
<212> TYPE: PRT
<213> ORGANISM: human

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial
<220> FEATURE:
<223> OTHER INFORMATION: synthetic peptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial
<220> FEATURE:
<223> OTHER INFORMATION: synthetic peptide
```

```
<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Artificial
<220> FEATURE:
<223> OTHER INFORMATION: synthetic peptide

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 5
<211> LENGTH: 20
<212> TYPE: DNA
<213> ORGANISM: Artificial
<220> FEATURE:
<223> OTHER INFORMATION: synthetic oligonucleotide

<400> SEQUENCE: 5
gaacctcgcg gacagttaag                                              20

<210> SEQ ID NO 6
<211> LENGTH: 53
<212> TYPE: DNA
<213> ORGANISM: Artificial
<220> FEATURE:
<223> OTHER INFORMATION: synthetic oligonucleotide

<400> SEQUENCE: 6
ggatcctccg ccgccgcagc tcttaggttt cttgtccacc ttggtgttgc tgg         53

<210> SEQ ID NO 7
<211> LENGTH: 55
<212> TYPE: PRT
<213> ORGANISM: Artificial
<220> FEATURE:
<223> OTHER INFORMATION: synthetic peptide

<400> SEQUENCE: 7

Gly Ser Gly Gly Gly Gly Ser Gly Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 8
<211> LENGTH: 92
<212> TYPE: DNA
<213> ORGANISM: Artificial
<220> FEATURE:
<223> OTHER INFORMATION: synthetic oligonucleotide
```

-continued

<210> SEQ ID NO 8
... (continued)

<400> SEQUENCE: 8
gtggcgggtc tggcggaggt ggcagccaca tccagatccc gccggggctc acggagctgc    60
tgcagggcta cacggtggag gtgctgcgac ag                                  92

<210> SEQ ID NO 9
<211> LENGTH: 92
<212> TYPE: DNA
<213> ORGANISM: Artificial
<220> FEATURE:
<223> OTHER INFORMATION: synthetic oligonucleotide

<400> SEQUENCE: 9
gcgcgagctt ctctcaggcg ggtgaagtac tccactgcga attcgacgag gtcaggcggc    60
tgctgtcgca gcacctccac cgtgtagccc tg                                  92

<210> SEQ ID NO 10
<211> LENGTH: 30
<212> TYPE: DNA
<213> ORGANISM: Artificial
<220> FEATURE:
<223> OTHER INFORMATION: synthetic oligonucleotide

<400> SEQUENCE: 10
ggatccggag gtggcgggtc tggcggaggt                                     30

<210> SEQ ID NO 11
<211> LENGTH: 30
<212> TYPE: DNA
<213> ORGANISM: Artificial
<220> FEATURE:
<223> OTHER INFORMATION: synthetic oligonucleotide

<400> SEQUENCE: 11
cggccgtcaa gcgcgagctt ctctcaggcg                                     30

<210> SEQ ID NO 12
<211> LENGTH: 29
<212> TYPE: PRT
<213> ORGANISM: Artificial
<220> FEATURE:
<223> OTHER INFORMATION: synthetic peptide

<400> SEQUENCE: 12

Gly Ser Gly Gly Gly Gly Ser Gly Gly Gly Gly Ser Gln Ile Glu Tyr
 1               5                  10                  15

Leu Ala Lys Gln Ile Val Asp Asn Ala Ile Gln Gln Ala
            20                  25

<210> SEQ ID NO 13
<211> LENGTH: 96
<212> TYPE: DNA
<213> ORGANISM: Artificial
<220> FEATURE:
<223> OTHER INFORMATION: synthetic oligonucleotide

<400> SEQUENCE: 13
ggatccggag gtggcgggtc tggcggaggt ggcagccaga tcgagtacct ggccaagcag    60
atcgtggaca acgccatcca gcaggcctga cggccg                              96

<210> SEQ ID NO 14
<211> LENGTH: 96
<212> TYPE: DNA

<213> ORGANISM: Artificial
<220> FEATURE:
<223> OTHER INFORMATION: synthetic oligonucleotide

<400> SEQUENCE: 14
cggccgtcag gcctgctgga tggcgttgtc cacgatctgc ttggccaggt actcgatctg      60
gctgccacct ccgccagacc cgccacctcc ggatcc      96

<210> SEQ ID NO 15
<211> LENGTH: 30
<212> TYPE: DNA
<213> ORGANISM: Artificial
<220> FEATURE:
<223> OTHER INFORMATION: synthetic oligonucleotide

<400> SEQUENCE: 15
ggatccggag gtggcgggtc tggcggaggt      30

<210> SEQ ID NO 16
<211> LENGTH: 22
<212> TYPE: DNA
<213> ORGANISM: Artificial
<220> FEATURE:
<223> OTHER INFORMATION: synthetic oligonucleotide

<400> SEQUENCE: 16
cggccgtcag gcctgctgga tg      22

<210> SEQ ID NO 17
<211> LENGTH: 28
<212> TYPE: DNA
<213> ORGANISM: Artificial
<220> FEATURE:
<223> OTHER INFORMATION: synthetic oligonucleotide

<400> SEQUENCE: 17
ccatgggcag ccacatccag atcccgcc      28

<210> SEQ ID NO 18
<211> LENGTH: 55
<212> TYPE: DNA
<213> ORGANISM: Artificial
<220> FEATURE:
<223> OTHER INFORMATION: synthetic oligonucleotide

<400> SEQUENCE: 18
ggatccgcca cctccagatc ctccgccgcc agcgcgagct tctctcaggc gggtg      55

<210> SEQ ID NO 19
<211> LENGTH: 44
<212> TYPE: DNA
<213> ORGANISM: Artificial
<220> FEATURE:
<223> OTHER INFORMATION: synthetic oligonucleotide

<400> SEQUENCE: 19
ggatccggcg gaggtggctc tgaggtccaa ctggtggaga gcgg      44

<210> SEQ ID NO 20
<211> LENGTH: 30
<212> TYPE: DNA
<213> ORGANISM: Artificial
<220> FEATURE:
<223> OTHER INFORMATION: synthetic oligonucleotide -continued

```
<400> SEQUENCE: 20
cggccgtcag cagctcttag gtttcttgtc                                             30

<210> SEQ ID NO 21
<211> LENGTH: 42
<212> TYPE: PRT
<213> ORGANISM: Artificial
<220> FEATURE:
<223> OTHER INFORMATION: synthetic peptide

<400> SEQUENCE: 21
```

Lys Gln Ile Glu Tyr Leu Ala Lys Gln Ile Val Asp Asn Ala Ile Gln
1               5                   10                  15

Gln Ala Lys Gly Cys Cys Gly Lys Ala Gln Gln Ile Ala Asn Asp Val
            20                  25                  30

Ile Gln Lys Ala Leu Tyr Glu Ile Gln Lys
        35                  40

```
<210> SEQ ID NO 22
<211> LENGTH: 48
<212> TYPE: DNA
<213> ORGANISM: Artificial
<220> FEATURE:
<223> OTHER INFORMATION: synthetic oligonucleotide

<400> SEQUENCE: 22
catgtgcggc cacatccaga tcccgccggg gctcacggag ctgctgca                         48

<210> SEQ ID NO 23
<211> LENGTH: 40
<212> TYPE: DNA
<213> ORGANISM: Artificial
<220> FEATURE:
<223> OTHER INFORMATION: synthetic oligonucleotide

<400> SEQUENCE: 23
gcagctccgt gagccccggc gggatctgga tgtggccgca                                  40

<210> SEQ ID NO 24
<211> LENGTH: 73
<212> TYPE: DNA
<213> ORGANISM: Artificial
<220> FEATURE:
<223> OTHER INFORMATION: synthetic oligonucleotide

<400> SEQUENCE: 24
gatccggagg tggcgggtct ggcggaggtt gcggccacat ccagatcccg ccggggctca           60
cggagctgct gca                                                              73

<210> SEQ ID NO 25
<211> LENGTH: 65
<212> TYPE: DNA
<213> ORGANISM: Artificial
<220> FEATURE:
<223> OTHER INFORMATION: synthetic oligonucleotide

<400> SEQUENCE: 25
gcagctccgt gagccccggc gggatctgga tgtggccgca acctccgcca gacccgccac           60
ctccg                                                                       65

<210> SEQ ID NO 26
<211> LENGTH: 93
<212> TYPE: DNA
<213> ORGANISM: Artificial
```

-continued

```
<220> FEATURE:
<223> OTHER INFORMATION: synthetic oligonucleotide

<400> SEQUENCE: 26
gatccggagg tggcgggtct ggcggatgtg gccagatcga gtacctggcc aagcagatcg    60
tggacaacgc catccagcag gccggctgct gaa                                 93

<210> SEQ ID NO 27
<211> LENGTH: 89
<212> TYPE: DNA
<213> ORGANISM: Artificial
<220> FEATURE:
<223> OTHER INFORMATION: synthetic oligonucleotide

<400> SEQUENCE: 27
ttcagcagcc ggcctgctgg atggcgttgt ccacgatctg cttggccagg tactcgatct    60
ggccacatcc gccagacccg ccacctccg                                      89

<210> SEQ ID NO 28
<211> LENGTH: 31
<212> TYPE: PRT
<213> ORGANISM: Artificial
<220> FEATURE:
<223> OTHER INFORMATION: synthetic peptide

<400> SEQUENCE: 28

Gly Glu Tyr Phe Thr Leu Gln Ile Arg Gly Arg Glu Arg Phe Glu Met
1               5                   10                  15

Phe Arg Glu Leu Asn Glu Ala Leu Glu Leu Lys Asp Ala Gln Ala
            20                  25                  30

<210> SEQ ID NO 29
<211> LENGTH: 9
<212> TYPE: PRT
<213> ORGANISM: Artificial
<220> FEATURE:
<223> OTHER INFORMATION: synthetic peptide

<400> SEQUENCE: 29

Gly Ser Gly Gly Gly Gly Ser Gly Gly
1               5

<210> SEQ ID NO 30
<211> LENGTH: 12
<212> TYPE: PRT
<213> ORGANISM: Artificial
<220> FEATURE:
<223> OTHER INFORMATION: synthetic peptide

<400> SEQUENCE: 30

Gly Gly Gly Gly Ser Gly Gly Gly Ser Gly Gly Gly
1               5                   10

<210> SEQ ID NO 31
<211> LENGTH: 24
<212> TYPE: DNA
<213> ORGANISM: Artificial
<220> FEATURE:
<223> OTHER INFORMATION: synthetic oligonucleotide

<400> SEQUENCE: 31
agatctggcg cacctgaact cctg                                           24

<210> SEQ ID NO 32
<211> LENGTH: 33
```

```
<212> TYPE: DNA
<213> ORGANISM: Artificial
<220> FEATURE:
<223> OTHER INFORMATION: synthetic oligonucleotide

<400> SEQUENCE: 32
gaattcggat cctttacccg gagacaggga gag                                    33

<210> SEQ ID NO 33
<211> LENGTH: 100
<212> TYPE: DNA
<213> ORGANISM: Artificial
<220> FEATURE:
<223> OTHER INFORMATION: synthetic oligonucleotide

<400> SEQUENCE: 33
catcatggga tggagctgta tcatcctctt cttggtagca acagctacag gtgtccactc       60
cgacggctgt ggccagatcg agtacctggc caagcagatc                            100

<210> SEQ ID NO 34
<211> LENGTH: 100
<212> TYPE: DNA
<213> ORGANISM: Artificial
<220> FEATURE:
<223> OTHER INFORMATION: synthetic oligonucleotide

<400> SEQUENCE: 34
ccgccagacc cgccacctcc ggaccctccg ccgccgcagc cggcctgctg gatggcgttg       60
tccacgatct gcttggccag gtactcgatc tggccacagc                            100

<210> SEQ ID NO 35
<211> LENGTH: 36
<212> TYPE: DNA
<213> ORGANISM: Artificial
<220> FEATURE:
<223> OTHER INFORMATION: synthetic oligonucleotide

<400> SEQUENCE: 35
tctagacaca ggacctcatc atgggatgga gctgta                                 36

<210> SEQ ID NO 36
<211> LENGTH: 36
<212> TYPE: DNA
<213> ORGANISM: Artificial
<220> FEATURE:
<223> OTHER INFORMATION: synthetic oligonucleotide

<400> SEQUENCE: 36
cagctggatg tcacctccgc cagacccgcc acctcc                                 36

<210> SEQ ID NO 37
<211> LENGTH: 21
<212> TYPE: PRT
<213> ORGANISM: Artificial
<220> FEATURE:
<223> OTHER INFORMATION: synthetic peptide

<400> SEQUENCE: 37

Lys Gln Ile Glu Tyr Leu Ala Lys Gln Ile Val Asp Asn Ala Ile Gln
1               5                   10                  15

Gln Ala Lys Gly Cys
            20

<210> SEQ ID NO 38
<211> LENGTH: 10
```

```
<212> TYPE: PRT
<213> ORGANISM: Artificial
<220> FEATURE:
<223> OTHER INFORMATION: synthetic peptide

<400> SEQUENCE: 38

Gly Gly Gly Gly Ser Gly Gly Gly Cys Gly
1               5                   10
```